US012667558B2

(12) United States Patent
Holmes et al.

(10) Patent No.: US 12,667,558 B2
(45) **Date of Patent: *Jun. 30, 2026**

(54) TREATMENT OF HUMAN CORONAVIRUS INFECTIONS USING ALPHA-GLUCOSIDASE GLYCOPROTEIN PROCESSING INHIBITORS

(71) Applicant: FLORIDA STATE UNIVERSITY RESEARCH FOUNDATION, INC., Tallahassee, FL (US)

(72) Inventors: Eric Holmes, Tallahassee, FL (US); Gary Ostrander, Tallahassee, FL (US); Geoffrey Stuart Dow, Washington, DC (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 850 days.

This patent is subject to a terminal disclaimer.

(21) Appl. No.: 17/664,693

(22) Filed: May 24, 2022

(65) Prior Publication Data

US 2022/0339140 A1 Oct. 27, 2022

Related U.S. Application Data

(63) Continuation of application No. 17/180,140, filed on Feb. 19, 2021, now Pat. No. 11,369,592.

(60) Provisional application No. 62/979,855, filed on Feb. 21, 2020.

(51) Int. Cl.

| | |
|---|---|
| ***A61K 31/437*** | (2006.01) |
| ***G01N 33/53*** | (2006.01) |
| ***G01N 33/68*** | (2006.01) |

(52) U.S. Cl.

CPC ....... *A61K 31/437* (2013.01); *G01N 33/5308* (2013.01); *G01N 33/6803* (2013.01); *G01N 2800/26* (2013.01)

(58) Field of Classification Search

CPC ..... A61P 31/14; A61K 31/437; A61K 31/445; A61K 45/06

See application file for complete search history.

(56) References Cited

U.S. PATENT DOCUMENTS

| | | | |
|---|---|---|---|
| 4,065,562 | A | 12/1977 | Katsuya et al. |
| 4,182,767 | A | 1/1980 | Murai et al. |
| 4,278,683 | A | 7/1981 | Stoltefuss et al. |
| 4,533,668 | A | 8/1985 | Matsumura et al. |
| 4,639,436 | A | 1/1987 | Junge et al. |
| 5,004,746 | A | 4/1991 | Liu et al. |
| 5,017,563 | A | 5/1991 | Liu et al. |
| 5,043,273 | A | 8/1991 | Scudder et al. |
| 2017/0312257 | A1 | 11/2017 | Holmes et al. |

FOREIGN PATENT DOCUMENTS

| | | |
|---|---|---|
| WO | WO 2006/077427 | 7/2006 |
| WO | WO 2014/143907 | 9/2014 |
| WO | WO 2018/017426 | 1/2018 |

OTHER PUBLICATIONS

Stella (J. Pharmaceutical Sciences, 2010, 99(12), pp. 4755-4765) (Year: 2010).*
Wikipedia, 2025 (Year: 2025).*
WebMD, 2022 (Year: 2022).*
NIAID (National Institute of Allergy and Infectious Diseases), 2009 (Year: 2009).*
ECDPC, 2025 (Year: 2025).*
Alabama public health, 2024 (Year: 2024).*
Wolff, Burger's Medicinal Chemistry and Drug Discovery, 5th Edition, vol. I Principles and Practice, pp. 975-977, 1995 (Year: 1995).*
Bundgaard (Design of Prodrugs, 1985, chapter 1) (Year: 1985).*
Silverman (Prodrugs and Drug Delivery Systems, The Organic Chemistry of Drug Design and Drug Action, pp. 352-399, 1992) (Year: 1992).*
Office Action from European Office for application 21757552.1 mailed Mar. 14, 2025.
Roujian Lu et al., "Genomic characterisation and epidemiology of 2019 novel coronavirus: implications for virus origins and receptor binding", The Lancet, vol. 395, Issue 10224, 2020, pp. 565-574, ISSN 0140-6736, https://doi.org/10.1016/S0140-6736(20)30251-8. (https://www.sciencedirect.com/science/article/pii/S0140673620302518).
M. Fukushi et al: "Monitoring of S Protein Maturation in the Endoplasmic Reticulum by Calnexin Is Important for the Infectivity of Severe Acute Respiratory Syndrome Coronavirus", Journal of Virology, vol. 86, No. 21,Aug. 22, 2012 (Aug. 22, 2012), pp. 11745-11753, XP055764376,US ISSN: 0022-538X, DOI: 10.1128/JVI.01250-12.
Pi-Hui Liang et al: "Novel Five-Membered Iminocyclitol Derivatives as Selective and Potent Glycosidase Inhibitors: New Structures for Antivirals and Osteoarthritis", Chembiochem, John Wiley & Sons, Inc, Hoboken, USA, vol. 7, No. 1, Jan. 5, 2006 (Jan. 5, 2006), pp. 165-173, XP072146894, ISSN: 1439-4227, DOI: 10.1002/CBIC.200500321.

(Continued)

*Primary Examiner* — Umamaheswari Ramachandran
(74) *Attorney, Agent, or Firm* — Thomas | Horstemeyer, LLP

(57) ABSTRACT

The present invention concerns the use of an alpha-glucosidase glycoprotein processing inhibitor for the treatment or prevention of human coronavirus infections, such as SARS-CoV-2 or SARS-CoV-2 variant infections. Aspects of the invention include methods for treating or preventing coronavirus infection, or a symptom thereof, by administering an alpha-glucosidase glycoprotein processing inhibitor, such as castanospermine, or a pharmaceutically acceptable salt, derivative, or prodrug thereof, to a human subject; methods for inhibiting human coronavirus infection in a human cell in vitro or in vivo; pharmaceutical compositions; packaged dosage formulations; and kits for treating or preventing human coronavirus infection.

14 Claims, 6 Drawing Sheets

Specification includes a Sequence Listing.

(56) References Cited

OTHER PUBLICATIONS

Extended European Search Report for European Patent Application No. 21757552.1-1112 / 4106752 PCT/US202107017 mailed Feb. 19, 2024.

Aguilar-Moncayo, M. et al. "Glycosidase inhibition by ring-modified castanospermine analogues: tackling enzyme selectivity by inhibitor tailoring" *Org. Biomol. Chem.*, 2009, 7:2738-2747.

Balogh Sivars, K. et al. "A 3D human airway model enables prediction of respiratory toxicity of inhaled drugs in vitro" *Toxicol Sci*. 2018, 162(1):301-308.

Boda, B. et al. "Antiviral drug screening by assessing epithelial functions and innate immune responses in human 3D airway epithelium model" *Antiviral Res.*, 2018, 156:72-79.

Brendel, E. and Wingender, W., "Clinical Pharmacology of Glucosidase Inhibitors" Chapter 21, pp. 611-632, In: Kuhlmann J., Puls W. (eds) Oral Antidiabetics. Handbook of Experimental Pharmacology, vol. 119. Springer, Berlin, Heidelberg, 1996.

Chang, J. et al. "Competitive inhibitor of cellular a-glucosidases protects mice from lethal dengue virus infection" *Antiviral Res.*, 2011, 92(2):369-371.

Chang, J. et al. "Imino sugar glucosidase inhibitors as broadly active anti-filovirus agents" *Emerging Microbes and Infections*, 2013, 2(11):e77 (7 pages).

Clarke, E.C. et al. "The iminosugars celgosivir, castanospermine and UV-4 inhibit SARS-CoV-2 replication" *Glycobiology*, May 2021 (Epub Sep. 2020), 31(4):378-384.

Constant, S. et al. "The Use of in vitro 3D Cell Models of Human Airway Epithelia (MucilAir™) in Inhalation Toxicity" Chapter 2, pp. 15-33, In: Cellular In Vitro Testing: Methods and Protocols (Ed. John Haycock et al.), Jenny Stanford Publishing, NY, 2013.

Courageot, M-P. et al. "Alpha-glucosidase inhibitors reduce dengue virus production by affecting the initial steps of virion morphogenesis in the endoplasmic reticulum" *Journal of Virology*, 2000, 74(1):564-572.

Durantel, D. "Celgosivir, an α-glucosidase I inhibitor for the potential treatment of hepatitis C virus infection" *Current Opinion in Investigational Drugs*, 2009, 10(8):860-870.

Elbein, A.D. "Glycosidase inhibitors as antiviral and/or antitumor agents," *Semin Cell Biol.*, 1991, 2(5):309-317, abstract.

Elbein, A.D. "Glycosidase inhibitors: inhibitors of N-linked oligosaccharide processing" *FASEB J*, 1991, 5(15):3055-3063.

Essaidi-Laziosi, M. et al. "Propagation of respiratory viruses in human airway epithelia reveals persistent virus-specific signatures" *J Allergy Clin Immunol.*, Jun. 2018 (Epub Aug. 2017), 141(6):2074-2084.

Gloster, T.M. and Davies, G.J. "Glycosidase inhibition: assessing mimicry of the transition state" *Org. Biomol. Chem.*, Jan. 2010 (Epub Nov. 2009), 8(2):305-320.

Hoffmann, W. et al. "Establishment of a Human 3D Tissue-Based Assay for Upper Respiratory Tract Absorption" *Applied In Vitro Toxicology*, 2018, 4(2):139-148.

Huang, S. and Caulfuty, M. "A novel in vitro cell model of the human airway epithelium" 3R-Info-Bulletin, No. 41, Oct. 2009 (2 pages).

Jacob, G.S. "Glycosylation inhibitors in biology and medicine" *Curr Opin Struct Biol.*, 1995, 5(5):605-611.

Junge, B. et al. "Chemistry and Structure-Activity Relationships of Glucosidase Inhibitors" Chapter 15, pp. 411-482, In: Kuhlmann J., Puls W. (eds) Oral Antidiabetics. Handbook of Experimental Pharmacology, vol. 119. Springer, Berlin, Heidelberg, 1996.

Kajimoto, T. and Node, M. "Inhibitors against glycosidases as medicines" *Curr Top Med Chem*, 2009, 9(1):13-33.

Kang, M.S. et al. "Castanospermine analogues: their inhibition of glycoprotein processing α-glucosidases from porcine kidney and B16F10 cells" *Glycobiology*, 1995, 5(1):147-152, abstract.

Kaushal, G.P. et al., "Selective inhibition of glycoprotein processing enzymes. Differential inhibition of glucosidases I and II in cell culture" *J Biol Chem.*, 1988, 263(33):17278-17283.

Krause, H.P. and Ahr, H.J. "Pharmacokinetics and Metabolism of Glucosidase Inhibitors" Chapter 19, pp. 541-555, In: Kuhlmann J., Puls W. (eds) Oral Antidiabetics. Handbook of Experimental Pharmacology, vol. 119. Springer, Berlin, Heidelberg, 1996.

Krishnan, M.N. and Garcia-Blanco, M.A. "Targeting host factors to treat West Nile and dengue viral infections" *Viruses*, 2014, 6:683-708.

Laine, R.A. "The case for re-examining glycosylation inhibitors, mimetics, primers and glycosylation decoys as antivirals and anti-inflammatoires in COVID19" Sep. 2020, 30(10):763-767.

Lu, Y. et al. "Loddigesiinols G-J: α-glucosidase inhibitors from Dendrobium loddigesii" *Molecules*, 2014, 19(6):8544-8555.

Mohana, S. et al. "Antiviral activities of sulfonium-ion glucosidase inhibitors and 5-thiomannosylamine disaccharide derivatives against dengue virus" *International Journal of Antimicrobial Agents*, 2012, 40(3):273-276.

Montefiori, D.C. et al. "Role of protein N-glycosylation in pathogenesis of human immunodeficiency virus type 1" *Proc Natl Acad Sci USA*, 1988, 85:9248-9252.

Pili, R. et al. "The alpha-glucosidase I inhibitor castanospermine alters endothelial cell glycosylation, prevents angiogenesis, and inhibits tumor growth" *Cancer Res.*, 1995, 55(13):2920-2926.

Ploschke, H.J. et al. "Analytical Methods of Determination of Glucosidase Inhibitors" Chapter 16, pp. 483-496, In: Kuhlmann J., Puls W. (eds) Oral Antidiabetics. Handbook of Experimental Pharmacology, vol. 119. Springer, Berlin, Heidelberg, 1996.

Puls, W. "General Pharmacology of Glucosidase Inhibitors" Chapter 18, pp. 535-539, In: Kuhlmann J., Puls W. (eds) Oral Antidiabetics. Handbook of Experimental Pharmacology, vol. 119, 1996.

Puls, W. "Pharmacology of Glucosidase Inhibitors" Chapter 17, pp. 497-534, In: Kuhlmann J., Puls W. (eds) Oral Antidiabetics. Handbook of Experimental Pharmacology, vol. 119, 1996.

Reus, A. et al. "Feasibility of a 3D human airway epithelial model to study respiratory absorption" *Toxicology In Vitro*, Mar. 2014 (Epub Nov. 2013), 28(2):258-264.

Richardson, P. et al. "Baricitinib as potential treatment for 2019-nCoV acute respiratory disease" Feb. 2020, 395(10223):e30-e31.

Saul, R. et al. "Castanospermine inhibits alpha-glucosidase activities and alters glycogen distribution in animals" *Proc Natl Acad Sci USA*, 1985, 82(1):93-97.

Sayce, A.C. et al. "Iminosugars Inhibit Dengue Virus Production via Inhibition of ER Alpha-Glucosidases—Not Glycolipid Processing Enzymes" *PLOS Neglected Tropical Diseases*, 2016, 10(3):e0004524 (22 pages).

Tapparel, C. et al. "Growth and characterization of different human rhinovirus C types in three-dimensional human airway epithelia reconstituted in vitro" *Virology*, 2013, 446(1-2):1-8.

Tyler, P. C. and Winchester, B.G. "Synthesis and Biological Activity of Castanospermine and Close Analogs" Chapter 7, pp. 125-156, In: Iminosugars as Glycosidase Inhibitors: Nojirimycin and Beyond (Ed. A. E. Stütz), Wiley-VCH Verlag GmbH & Co. KGaA, Weinheim, FRG, 1990.

Walker, B.D. et al. "Inhibition of human immunodeficiency virus syncytium formation and virus replication by castanospermine" *Proc Natl Acad Sci USA*, 1987, 84(22):8120-8124.

Wan, Y. et al. "Receptor Recognition by the Novel Coronavirus from Wuhan: an Analysis Based on Decade-Long Structural Studies of SARS Coronavirus" *Journal of Virology*, Apr. 2020 (Epub Jan. 2020), 94(7):e00127-20 (9 pages).

Wang, M. et al. "Remdesivir and chloroquine effectively inhibit the recently emerged novel coronavirus (2019-nCoV) in vitro" *Cell Research*, Mar. 2020 (Epub Feb. 2020), 30 (3):269-271.

Warfield, K.L. et al. "Inhibition of endoplasmic reticulum glucosidases is required for in vitro and in vivo dengue antiviral activity by the iminosugar UV-4" *Antiviral Research*, 2016, 129:93-98.

Winchester, B.G. et al. "The structural basis of the inhibition of human glycosidases by castanospermine analogues" *Biochem. J.*, 1990, 269:227-231.

Zhao, X. et al. "Inhibition of Endoplasmic Reticulum-Resident Glucosidases Impairs Severe Acute Respiratory Syndrome Coronavirus and Human Coronavirus NL63 Spike Protein-Mediated Entry by Altering the Glycan Processing of Angiotensin I-Converting Enzyme 2" *Antimicrob Agents Chemother*, 2015, 59:206-216.

(56) References Cited

OTHER PUBLICATIONS

Zhu, N. et al. "A Novel Coronavirus from Patients with Pneumonia in China, 2019" *N Engl J Med*, Feb. 2020 (Epub Jan. 24, 2020), 382(8):727-733.
Yang, Q. et al. "Inhibition of SARS-CoV-2 viral entry upon blocking N- and O-glycan elaboration" *eLife*, 2020, 9:e61552 (19 pages).
Watanabe, Y. et al. "Site-specific glycan analysis of the SARS-CoV-2 spike" *Science*, 2020, 369(6501):330-333.
NIAID, National Institute of Allergy and Infectious Diseases, "Understanding Microbes in Sickness and in Health" NIH Publication No. 06-4914, Jan. 2006, pp. 1-52 (Year: 2006).
Office Action from European Office for application 21757552.1 mailed Dec. 4, 2025.
Zaro Jennica L: "Lipid-Based Drug Carriers for Prodrugs to Enhance Drug Delivery", The AAPS Journal, Springer US, Boston, vol. 17, No. 1, Oct. 1, 2014 (Oct. 1, 2014), pp. 83-92, XP035420758, DOI: 10.1208/S12248-014-9670-Z [retrieved on Oct. 1, 2014].
Shashwat S. Banerjee et al: "Poly(ethylene glycol)-Prodrug Conjugates: Concept, Design, and Applications", Journal of Drug Delivery, vol. 22, No. 4, Jan. 1, 2012 (Jan. 1, 2012), pp. 1-17, XP055079947, ISSN: 2090-3014, DOI: 10.1155/2012/103973.

* cited by examiner

TREATMENT OF HUMAN CORONAVIRUS INFECTIONS USING ALPHA-GLUCOSIDASE GLYCOPROTEIN PROCESSING INHIBITORS

CROSS-REFERENCE TO RELATED APPLICATIONS

The present application is a continuation of U.S. application Ser. No. 17/180,140, filed Feb. 19, 2021, which claims the benefit of U.S. Provisional Application Ser. No. 62/979,855, filed Feb. 21, 2020, which is hereby incorporated by reference herein in its entirety, including any figures, tables, nucleic acid sequences, amino acid sequences, or drawings.

SEQUENCE LISTING

The Sequence Listing for this application is labeled "2TJ5788. txt" which was created on Jun. 24, 2022 and is 1021 BYTES. The entire contents of the sequence listing is incorporated herein by reference in its entirety.

BACKGROUND OF THE INVENTION

Coronaviruses are enveloped viruses of the family Coronaviridae, which are transmitted through the air and primarily infect the cells of the upper respiratory and gastrointestinal tract of mammals and birds. The name coronavirus is derived from the Latin "crown" or "halo", which refers to its characteristic morphology, which resembles a crown or solar corona when imaged using an electron microscope.

Coronaviruses cause illness in adults and children ranging from the common cold to more severe diseases. Common signs of infection include respiratory symptoms, fever, cough, shortness of breath, and breathing difficulties. In more severe cases, coronavirus infection can cause pneumonia, severe acute respiratory syndrome (SARS), kidney failure, and even death. The widely publicized human coronavirus discovered in 2003, SARS-CoV, causes both upper and lower respiratory tract infections.

Coronaviruses are zoonotic, meaning they are transmitted between animals and humans. Several known coronaviruses are circulating in animals that have not yet infected humans. A novel coronavirus (nCoV) is a new strain that has not been previously identified in humans. There are currently no vaccines or antiviral drugs to prevent or treat human coronavirus infections.

Following the outbreak of SARS in 2003, which had begun the prior year in Asia, and secondary cases elsewhere in the world, the World Health Organization (WHO) issued a press release stating that a novel coronavirus identified by a number of laboratories was the causative agent for SARS. The virus was officially named the SARS coronavirus (SARS-CoV).

In September 2012, a new type of coronavirus was identified, initially called Novel Coronavirus 2012, and now officially named Middle East respiratory syndrome coronavirus (MERS-CoV). After the Dutch Erasmus Medical Centre sequenced the virus, the virus was given the name Human Coronavirus-Erasmus Medical Centre (HCoV-EMC). The final name for the virus is Middle East respiratory syndrome coronavirus (MERS-CoV).

In May 2014, two United States cases of MERS-CoV infection were recorded, both occurring in healthcare workers who worked in Saudi Arabia and then traveled to the U.S. In May 2015, an outbreak of MERS-CoV occurred in the Republic of Korea, when a man who had traveled to the Middle East, visited hospitals in the Seoul area to treat his illness, causing one of the largest outbreaks of MERS-CoV outside the Middle East.

In December 2019, a pneumonia outbreak was reported in Wuhan, China, and was traced to a novel strain of coronavirus, which was given the interim name 2019-nCoV by the World Health Organization (WHO), later renamed SARS-CoV-2 by the International Committee on Taxonomy of Viruses (Zhu N. et al, "A Novel Coronavirus from Patients with Pneumonia in China, 2019", *N Engl J Med*, February 2020, 382(8):727-733, Epub 24 Jan. 2020). Coronavirus disease 2019 (COVID-19), formerly known as 2019-nCoV acute respiratory disease, is the infectious disease caused by SARS-CoV-2. SARS-CoV-2 has killed more people than 2003 SARS outbreak. Some researchers have suggested that the Huanan Seafood Market may not be the original source of viral transmission to humans.

A new virus variant has one or more genetic distinctions (e.g., mutations) that differentiate it from the wild-type or predominant virus variants already circulating among the general population, and several variants of SARS-CoV-2 have been reported in the United States and globally in 2020. Some of the SARS-CoV-2 variants that have emerged are particularly concerning, including at least B.1.1.7 identified in the United Kingdom, B.1.351 identified in South Africa, and P.1 identified in travelers from Brazil.

There remains a need for a safe and effective method of treating or preventing infections of coronavirus and associated symptoms, in particular those related to COVID-19, and its causative agent, SARS-CoV-2, and its variants.

BRIEF SUMMARY OF THE INVENTION

The present invention concerns the use of alpha-glucosidase glycoprotein processing inhibitors (also referred to herein as alpha-glucosidase inhibitors) for the treatment or prevention of human coronavirus infections, such as SARS-CoV-2 and its variants. In some embodiments, the alpha-glucosidase inhibitor comprises an alpha-glucosidase I inhibitor (sometimes referred to as a glucosidase I inhibitor), such as castanospermine or deoxynojirimycin.

One aspect of the invention is a method for the treatment or prevention of human coronavirus infection, comprising administering an alpha-glucosidase inhibitor to a human subject in need thereof. In some embodiments, the alpha-glucosidase inhibitor is a compound having the chemical structure shown in FIG. 1, FIG. 2, Formula (I), Formula (II), and/or Formula (III), or a pharmaceutically acceptable salt of any of the foregoing. The alpha-glucosidase inhibitor may be administered to the human subject as at least one initial (loading) dose. The method may include detecting the presence of the human coronavirus infection prior to administration of the alpha-glucosidase inhibitor. Any suitable method for diagnosis or testing of SARS-CoV-2 infection can be used, and such methods are well known in the art, including nucleic acid assays.

In some embodiments, the alpha-glucosidase inhibitor is administered to a human subject infected by a human coronavirus, such as SARS-CoV-2 or a variant thereof, as therapy. In some embodiments, the subject has the disease COVID-19.

In particular embodiments, the human subject is symptomatic for the coronavirus infection (e.g., SARS-CoV-2 infection) at the time of the administration. In other embodiments, the human subject has tested positive for the coronavirus infection at the time of the administration but is asymptomatic. In further embodiments, the method further comprises administering a second agent, such as a drug, to the human subject.

In other embodiments, the alpha-glucosidase inhibitor is administered to a human subject not infected by human coronavirus, such as SARS-CoV-2 or a variant thereof, as prophylaxis (to prevent or delay the onset of human coronavirus infection).

In particular embodiments, the human subject is asymptomatic for the coronavirus infection and/or has been diagnosed as corona virus negative (e.g., SARS-CoV-2 negative) at the time of the administration. In other particular embodiments, the human subject has been exposed to coronavirus (e.g., SARS-CoV-2) or has had close contact with someone infected with the coronavirus (e.g., SARS-CoV-2). In further embodiments, the method further comprises administering a second agent, such as a drug, to the human subject.

Another aspect of the invention concerns a method for inhibiting a human coronavirus infection, such as SARS-CoV-2, in a human cell, comprising contacting the cell in vitro or in vivo with an alpha-glucosidase inhibitor, such as castanospermine, or a pharmaceutically acceptable salt, derivative, or prodrug thereof, before or after the cell is infected. In some embodiments, the alpha-glucosidase inhibitor is a compound having the chemical structure shown in FIG. 1, FIG. 2, Formula (I), Formula (II), and/or Formula (III), or a pharmaceutically acceptable salt of any of the foregoing.

In some embodiments of the methods of the invention, the alpha-glucosidase inhibitor comprises castanospermine, acarbose, miglitol voglibose, emiglitate, kotalanol, or a derivative of any of the foregoing that retains alpha-glucosidase inhibitory activity. In some embodiments of the methods of the invention, the alpha-glucosidase inhibitor comprises castanospermine, or a derivative or prodrug of castanospermine, such as celgosivir (a derivative and prodrug).

In some embodiments of the methods of the invention, the human coronavirus is selected from among SARS-CoV-2, SARS-CoV, and MERS-CoV.

In some embodiments of the methods of the invention, the human coronavirus is a variant of SARS-CoV-2, such as the B.1.1.7 variant, B.1.351 variant, or P.1 variant.

In some embodiments of the methods of the invention, the human coronavirus is a common human coronavirus, such as type 229E, NL63, OC43, and HKU1.

For both methods of treatment and methods of prevention, in certain embodiments the at least one initial (loading) dose comprises about 40 to 600 mg of a compound of FIG. 1, FIG. 2, Formula (I), (II), and/or (III), or a pharmaceutically acceptable salt of any of the foregoing. In additional embodiments, each of the plurality of subsequent doses comprises about 25 to about 400 mg of a compound of FIG. 1, FIG. 2, Formula (I), (II), and/or (III), or a pharmaceutically acceptable salt of any of the foregoing.

In certain embodiments, the subsequent doses are administered at intervals of from about 6 to about 12 hours. In other embodiments, the subsequent doses are administered about every 6 hours, about every 8 hours, about every 12 hours, or about every 24 hours. In further embodiments, the subsequent doses are administered once, twice, three, four, or five times per day.

In certain embodiments, the total amount of a compound of FIG. 1, FIG. 2, Formula (I), (II), and/or (III) does not exceed 600 mg per day. In other embodiments the total amount of a single administration of a compound of FIG. 1, FIG. 2, Formula (I), (II), and/or (III) is 400 mg or less.

In additional embodiments, the subsequent doses are administered for about 1-10 days, about 1-15 days, about 1-20 days, about 1-25 days, about 30 days, about four weeks, about six weeks, about eight weeks, about three months, about four months, about five months, about six months, about seven months, about eight months, about nine months, about ten months, about eleven months, or about one year. In other embodiments, the subsequent doses are administered for about 3-10 days, 3-15 days, 5-20 days, 5-30 days, 10-40 days, or 10-50 days.

In the various embodiments, the human subject can be an adult or a child.

The compound of Formula (I) is represented by the following structure:

(I)

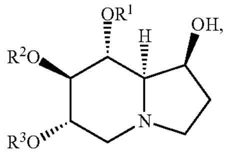

or a pharmaceutically acceptable salt thereof;

wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

In certain embodiments, the compound of Formula (I) is specifically the compound of Formula (II), below, or a pharmaceutically acceptable salt thereof:

(II)

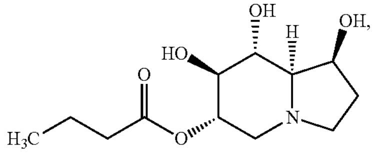

In preferred embodiments, the compound of Formula (I) is a prodrug of castanospermine, a natural product derived from the seeds of Castanospermum australe. Once administered compounds of Formula (I) are rapidly converted to castanospermine. Compounds of Formula (I) (e.g., celgosivir) are more rapidly and efficiently absorbed than castanospermine. Compounds of Formula (I) are also more readily absorbed into cells. As a result, compounds of Formula (I) may have higher 50% effective concentration (EC50) values and in vivo efficacy than castanospermine against SARS-CoV-2.

In certain embodiments, the at least one initial dose comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 27, at least 28, at least 29, or at least 30 doses. In other embodiments, the at least one initial dose comprising one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, at most 24, at most 25, at most 27, at most 28, at most 29, or at most 30 doses. In some embodiments, two or more initial doses are administered at intervals of from about 6 to about 12 hours. In other embodiments, two or more initial doses are administered about every 6 hours, about every 8 hours, about every 12 hours, or about every 24 hours. In further embodiments, two or more initial doses are administered once, twice, three, four, or five times per day.

In certain embodiments, the beginning of the administration of the subsequent doses is within a day of administration of the at least one initial dose. In further embodiments, the beginning of the administration of the subsequent doses is about 20 hours, about 15 hours, about 12 hours, about 8 hours, or about 6 hours after administration of the at last one initial dose.

In certain embodiments, at least one initial dose is the same as the subsequent doses, while in other embodiments the at least one initial dose differs from the subsequent doses. In particular embodiments, the at least one initial dose is higher than the subsequent doses. In further embodiments, the at least one initial dose is the same dosage amount throughout the method. In other embodiments, the at least one initial dose varies dosage amounts throughout the method. In further embodiments, the plurality of subsequent doses is the same dosage amount throughout the method. In other embodiments, the plurality of subsequent doses varies dosage amounts throughout the method.

In certain embodiments, for an adult subject, the initial dose can be between about 40 to about 600 mg. In other embodiments, the initial dose in an adult subject can be about 75-600 mg, 100-600 mg, 150-600 mg, about 200-500 mg, or about 250-400 mg. In further embodiments, the initial dose in an adult subject can be about 40 mg, about 60 mg, about 80 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, or about 600 mg. In a further embodiment, the initial dose in an adult subject is between about 550 to about 600 mg. In another embodiment, the initial dose in an adult subject is between about 500 to about 550 mg. In yet another embodiment, the initial dose in an adult subject is between about 450 to about 500 mg. In a further embodiment, the initial dose in an adult subject is between about 400 to about 450 mg. In another embodiment, the initial dose in an adult subject is between about 350 to about 400 mg. In further embodiment, the initial dose in an adult subject is between about 300 to about 350 mg. In yet another embodiment, the initial dose in an adult subject is between about 250 to about 300 mg. In further embodiment, the initial dose in an adult subject is between about 200 to about 250 mg. In another embodiment, the initial dose in an adult subject is between about 150 to about 200 mg. In another embodiment, the initial dose in an adult subject is between about 100 to about 150 mg. In further embodiments, the initial dose in an adult subject is between about 50 to about 100 mg.

The subsequent doses in an adult subject can be between about 40 to about 400 mg. In one embodiment, the subsequent dose in an adult subject is between about 250 to about 300 mg. In another embodiment the subsequent dose in an adult subject is between about 200 to about 250 mg. In yet another embodiment, the subsequent dose in an adult subject is between about 150 to about 200 mg. In a further embodiment, the subsequent dose in an adult subject is between about 100 to about 200 mg. In other embodiments, the subsequent dose in an adult subject is between about 40 to about 80 mg. In even further embodiments, the subsequent dose in an adult subject is between about 80 to about 100 mg. In an additional embodiment, the subsequent dose in an adult subject is between about 125 to about 175 mg. In yet another embodiment, the subsequent dose in an adult subject is about 150 mg. In another embodiment, the subsequent dose in an adult subject is about 100 mg.

For a child subject, the initial dose can be between about 15 to about 450 mg. In one embodiment, the initial dose in a child subject is between about 15 to about 25 mg. In another embodiment, the initial dose in a child subject is between about 25 to about 50 mg. In yet another embodiment, the initial dose in a child subject is between about 50 to about 75 mg. In still another embodiment, the initial dose in a child subject is between about 75 to about 100 mg. In further embodiment, the initial dose in a child subject is between about 100 to about 150 mg. In another embodiment, the initial dose in a child subject is between about 150 to about 200 mg. In yet another embodiment, the initial dose in a child subject is between about 200 to about 250 mg. In a further embodiment, the initial dose in a child subject is between about 250 to about 300 mg. In another embodiment, the initial dose in a child subject is between about 300 to about 350 mg. In yet another embodiment, the initial dose in a child subject is between about 350 to about 400 mg. In each instance, the dose can be administered as a single or split dose.

The subsequent doses in a child subject can be between about 15 to about 200 mg. In one embodiment, the subsequent dose in a child subject is between about 15 to about 25 mg. In another embodiment, the subsequent dose in a child subject is between about 25 to about 50 mg. In yet another embodiment, the subsequent dose in a child subject is between about 50 to about 75 mg. In still another embodiment, the subsequent dose in a child subject is between about 75 to about 100 mg. In further embodiment, the subsequent dose in a child subject is between about 100 to about 125 mg. In another embodiment, the subsequent dose in a child subject is between about 125 to about 150 mg. In yet another embodiment, the subsequent dose in a child subject is between about 150 to about 200 mg. In each instance, the dose can be administered as a single or split dose.

The compounds or pharmaceutical compositions of the present invention can be administered intravenously, orally, rectally or sublingually. In one embodiment, the route of administration is intravenous. In another embodiment, the route of administration is oral. In another embodiment, the route of administration is rectal. In yet another embodiment, the route of administration is sublingual.

The compounds or pharmaceutical compositions of the present invention can be administered as a single or as a divided dose. In some embodiments, the at least one initial dose can be single, divided, or a combination thereof. In some embodiments, the subsequent doses can be single, divided, or a combination thereof. For the subsequent doses in one embodiment, the human subject is administered a divided dose of from about 25 to about 400 mg of a compound of Formula (I), (II), and/or (III), or a pharmaceutical composition comprising a compound of Formula (I), (II), and/or (III), for between about 3 to about 30 days. In another embodiment, the human subject is administered the subsequent doses as a single dose of from about 25 to about 400 mg for between about 3 to about 40 days. In yet another embodiment, the human subject is administered the subsequent doses as a single dose of from about 25 to about 400 mg for between about 3 day to about 60 days. In a further embodiment, the human subject is administered the subsequent doses as a single dose of from about 25 to about 400 mg for between about 3 days to about 60 days. In other versions, the subsequent doses are administered no longer than about 10 days; in yet other versions no longer than about 20 days; in further versions no longer than about 50 days; other versions no longer than about 100 days; and in other versions no longer than about one year.

The invention also relates to methods of preventing a disease resulting from SARS-CoV-2 infection by achieving a steady state Cmin serum or plasma concentration of between about 0.05 and about 2.0 microgram/mL of castanospermine in an adult or child subject. In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In another aspect of the invention, viral load reduction of human subjects receiving the method of treatment is at least 50% greater than in persons not administered the compound or in placebo-administered groups. In one embodiment, the virological log reduction in human subjects receiving the method of treatment is at least 50% greater than in persons not administered the compound or in placebo-administered groups. In another embodiment, the virological log reduction in human subjects receiving the method of treatment is between about 60% to about 70% greater than in persons not administered the compound or in placebo-administered groups. In another embodiment, the virological log reduction in human subjects receiving the method of treatment is between about 70% to about 80% greater than in persons not administered the compound or in placebo-administered groups. In yet another embodiment, the virological log reduction in human subjects receiving the method of treatment is between about 80 to about 90% greater than in persons not administered the compound or in placebo-administered groups.

Another aspect of the invention concerns a composition comprising an alpha-glucosidase inhibitor for treatment of human coronavirus infection, such as such as SARS-CoV-2 infection. In some embodiments of the composition of the invention, the alpha-glucosidase inhibitor comprises castanospermine, acarbose, miglitol voglibose, emiglitate, kotalanol, or a derivative or prodrug of any of the foregoing that has alpha-glucosidase inhibitory activity. In some embodiments of the composition, the alpha-glucosidase inhibitor of the composition of the invention comprises castanospermine, or a derivative or prodrug of castanospermine, such as celgosivir (a derivative and prodrug). In some embodiments of the composition, the composition comprises a packaged dosage formulation or a kit for treatment or prevention of a human coronavirus infection.

Another aspect of the invention concerns kits comprising, in one or more containers, an alpha-glucosidase inhibitor of the present invention. A kit of the invention can also comprise one or more other compounds, biological molecules, or drugs. In one embodiment, the kit of the invention comprises an alpha-glucosidase inhibitor, and optionally comprises one or more of a drug or composition used in treating a viral infection (e.g., a human coronavirus infection, such as SARS-CoV-2).

DETAILED DESCRIPTION OF THE INVENTION

Figure 1:
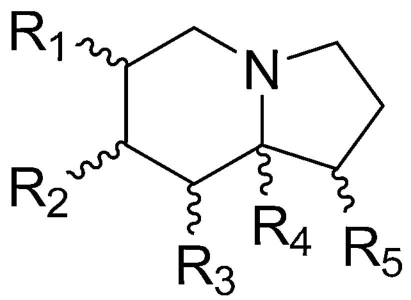
FIG. 1 shows a chemical structure illustrating an embodiment of alpha-glucosidase I inhibitors (also referred to as glucosidase I inhibitors). The structure of FIG. 1 encompasses castanospermine and some derivatives of castanospermine.

An aspect of the invention concerns a method for treatment or prevention of a human coronavirus infection, such as SARS-CoV-2, in a human subject, comprising administering to the human subject an effective amount of an alpha-glucosidase glycoprotein processing inhibitors (also referred to herein as alpha-glucosidase inhibitors), such as castanospermine, or a pharmaceutically acceptable salt, derivative, or prodrug thereof. The alpha-glucosidase inhibitor may be administered to the human subject before or after initiation of the coronavirus infection, thereby treating the coronavirus infection. In some embodiments, the subject has the disease COVID-19 at the time one or more alpha-glucosidase inhibitors is administered.

Castanospermine is an inhibitor of α- and β-glucosidases (Saul, R., Ghidoni, J. J., Molyneux, R. J., et al. (1985) *Proc Natl Acad Sci USA,* 82, 93-97). Glucosidases catalyze the cleavage of individual glucosyl residues from various glycoconjugates, including complex carbohydrates and glycoproteins. Glucose residues found on high mannose glycoprotein oligosaccharides must first be cleaved before they are further processed to yield complex type oligosaccharide structures. Inhibition of glycoprotein oligosaccharide processing can affect protein trafficking and cell functions that are dependent on glycosylation, including angiogenesis (Pili, R., Chang, J., Partis, R. A., et al. (1995) *Cancer Res.,* 55, 2920-2926). Castanospermine also interferes with viral replication and infection that is dependent on glucosidase activity (Montefiori, D. C., Robinson, W. E., and Mitchell, W. M. (1988) *Proc Natl Acad Sci USA,* 85, 9248-9252; Walker, B. D., Kowalski, M., Goh, W. C., et al. (1987) Proc Natl Acad Sci USA, 84, 8120-8124).

Another aspect of the invention concerns a method for inhibiting a human coronairus infection in a human cell, comprising contacting the cell in vitro or in vivo with an alpha-glucosidase inhibitor, such as castanospermine, or a pharmaceutically acceptable salt, derivative, or prodrug thereof, before or after the cell is infected.

The human corona virus may be any time or subgroup, including alpha, beta, gamma, and delta. In some embodiments of the aforementioned methods of the invention, the human coronavirus is selected from among SARS-CoV-2, SARS-CoV, and MERS-CoV. In some embodiments of the aforementioned methods of the invention, the human coronavirus is a common human coronavirus, such as type 229E, NL63, OC43, and HKU1.

Another aspect of the invention concerns a composition comprising an alpha-glucosidase inhibitor, such as castanospermine, or a pharmaceutically acceptable salt, derivative, or prodrug thereof.

In some embodiments of the aforementioned methods and composition of the invention, a derivative or prodrug of castanospermine having alpha-glucosidase inhibitory activity is used, such as the derivative celgosivir (6-O-butanoyl castanospermine). Celgosivir is also a prodrug of castanospermine.

Alpha-Glucosidase Glycoprotein Processing Inhibitors

Alpha-glucosidase hydrolyzes terminal non-reducing 1-4 linked alpha-glucose residues to release a single alpha-glucose molecule. Alpha-glucosidase is a carbohydrate-hydrolase that releases alpha-glucose as opposed to beta-glucose. Alpha-glucosidases include maltase, glucoinvertase, glucosidosucrase, maltase-glucoamylase, alpha-glucopyranosidase, glucosidoinvertase, alpha-D-glucosidase, alpha-glucoside hydrolase, alpha-1,4-glucosidase, and alpha-D-glucoside glucohydrolase.

Alpha-glucosidase glycoprotein processing inhibitors (also referred to herein as alpha-glucosidase inhibitors) include inhibitors of alpha-glucosidase production, inhibitors of glycoprotein processing, and inhibitors of alpha-glucosidase activity. Glycoprotein processing inhibitors interfere with the normal processing of N-linked glycoproteins by inhibiting glycosidases involved in these reactions. Compounds that inhibit alpha-glucosidase I and II prevent the removal of glucoses from high-mannose chains (see, for example, Kaushal G P et al., "Selective inhibition of glycoprotein processing enzymes. Differential inhibition of glucosidases I and II in cell culture," *J Biol Chem.,* 1988, 263(33):17278-17283; Albein A D, "Glycosidase inhibitors as antiviral and/or antitumor agents," *Semin Cell Biol.,* 1991, 2(5):309-317; and Albein A D, "Glycosidase inhibitors: inhibitors of N-linked oligosaccharide processing," *FASEB J,* 1991, 5(15):3055-3063; Jacob G S, "Glycosylation inhibitors in biology and medicine", *Curr Opin Struct Biol.,* 1995, 5(5):605-611; and Kajimoto T and Node M, "Inhibitors against glycosidases as medicines," *Curr Top Med Chem,* 2009, 9(1):13-33, each of which are incorporated by reference herein in their entirety).

Several alpha-glucosidases function in breaking down polysaccharides of glucose such as starch or glycogen. Because of this, inhibitors of these enzymes often have utility in the treatment of diabetes. Typically, the alpha-glucosidase inhibitors to be used in the various aspects of the invention (e.g., methods, compositions, packaged dosage formulations, and kits) are inhibitors of alpha-glucosidase I (also referred to as "glucosidase I"). This enzyme catalyzes the first steps in glycoprotein processing, wherein a (Glc)3 (Man)9(GlcNAc)2 structure is transferred enblock onto an Asn residue of a glycoprotein. Once attached, the first operation is to remove the Glc3 residues (later processing takes off many of the Man residues). As alpha-glucosidase I inhibitors, compounds such as castanospermine and deoxynojirimycin inhibit this reaction. Although the alpha-glucosidase inhibitors used in the various aspects of the invention may inhibit other glucosidase enzymes (in addition to alpha-glucosidase I), the inhibitors used will typically inhibit at least alpha-glucosidase I. In some embodiments of the methods and compositions of the invention, the alpha-glucosidase inhibitor selected only inhibits alpha-glucosidase I. In some embodiments of the methods and compositions of the invention, the alpha-glucosidase inhibitor selected inhibits alpha-glucosidase I and II.

Without being limited by theory of mechanism of action, the alpha-glucosidase inhibitor selected may inhibit glycoprotein processing of one or more human coronal glycoproteins, such as one or more of the spike (S) protein, nucleocapside (N) protein, membrane (M) protein, or envelope (E) protein, resulting in reduction or elimination of glucosidase-dependent replication of the coronavirus. In some embodiments, the alpha-glucosidase inhibitor inhibits processing of one or more surface glycoproteins of the coronavirus. In some embodiments, the alpha-glucosidase inhibitor inhibits processing of at least the S protein of the coronavirus.

Alpha-glucosidase inhibitors can inhibit the degradation and digestion of carbohydrate and thus limit an abrupt increase in postprandial blood glucose levels. The alpha-glucosidase inhibitors used in the various aspects of the invention may be any type of substance, such as a small molecule, polypeptide, nucleic acid, or extract. For example, a methanolic extract of *Centaurea calcitrapa* (Red start thistle) has been identified as having alpha-glucosidase activity (Kaskoos R (2013), *American Journal of Essential Oils and Natural Products*, vol. 1, no. 1, pp. 122-125). In some embodiments of the methods and compositions of the invention, the alpha-glucosidase inhibitor selected is one that acts as a competitive inhibitor of alpha-glucosidase.

In some embodiments of the methods and compositions of the invention, the alpha-glucosidase inhibitor is a saccharide that acts as competitive inhibitor of alpha-glucosidase. Nucleic acids that act as alpha-glucosidase inhibitors may act to inhibit the alpha-glucosidase, for example, by targeting and directly or indirectly interacting with the DNA or mRNA encoding alpha-glucosidase and therefore reducing alpha-glucosidase expression, or the nucleic acids may act through a polypeptide that is encoded by the nucleic acid molecule.

In some embodiments, the alpha-glucosidase inhibitor is an inhibitor of intestinal alpha-glucosidase of the intended subject. In some embodiments, the alpha-glucosidase inhibitor is an inhibitor of lysosomal alpha-glucosidase of the intended subject.

Inhibitors of alpha-glucosidase production include antisense molecules (e.g., antisense oligodeoxynucleotides (ODNs)) or small interfering RNA (siRNA) against the mRNA transcript for the alpha-glucosidase. Agents which decrease alpha-glucosidase bioavailability include neutralizing antibodies against alpha-glucosidase, soluble receptors or other proteins which can be engineered to bind alpha-glucosidase with higher affinity than its substrate in target tissues. Inhibitors of the alpha-glucosidase include neutralizing antibodies, inhibitory peptides or small molecule inhibitors which prevent alpha-glucosidase from binding to its substrate and/or otherwise carrying out its enzymatic activity in target tissues. In some embodiments, the alpha-glucosidase inhibitor comprises an antisense molecule, ribozyme, siRNA, or triplex forming nucleic acid.

Methods of measuring amounts of nucleic acids (e.g., RT-PCR) and protein (e.g., ELISA), and for screening for alpha-glucosidase enzyme activity, are known and can be used to identify agents that have alpha-glucosidase inhibitory activity (see Y.-M. Kim (2003), *Nutrition*, vol. 21, no. 6, pp. 756-761, and alpha-glucosidase assay kit (catalog no. KA 1608, Abnova; and catalog no. ab174093, Abcam)). Homology modeling of human alpha-glucosidase catalytic domains has been conducted and structure-activity-relationships have been studied (see, for example, Nakamura S. et al. (2012), *Open Journal of Medicinal Chemistry*, Vol. 2, pp. 50-60, which is incorporated herein by reference in its entirety).

In some embodiments of the methods and compositions of the invention, the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide. In some embodiments, the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin (DNJ) derivatives (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine or castanospermine derivatives), or polyhydroxypyrrolidine (e.g., monocyclic pyrrolidine derivative or bicyclic pyrrolidine derivative). In some embodiments, the alpha-glucosidase inhibitor is a higher N-alkyl derivative of DNJ, having an increased alkyl chain length of at least 5 carbon atoms to about 10 carbon atoms, relative to lower $C_1$-$C_4$ N-alkyl derivatives.

In some embodiments of the methods and compositions of the invention, the alpha-glucosidase inhibitor comprises a sulfonium ion (see, for example, Mohana S et al. (2012), *International Journal of Antimicrobial Agents*, vol. 40, no. 3, pp. 273-276, incorporated herein by reference in its entirety). In some embodiments, the alpha-glucosidase inhibitor comprises an imino sugar (e.g., DNJ, or a DNJ derivative with alkylation of the ring nitrogen (see, for example, Sayce A C et al. (2016), *PLOS Neglected Tropical Diseases*, vol. 10, issue 3, pp. 1-22; and Chang J et al. (2013), *Emerging Microbes and Infections*, e77); Chang J et al. (2011), *Antiviral Res.*, vol. 92, no. 2, pp. 369-3'71, which are each incorporated herein by reference in their entirety). Imino sugars are glucose mimetics with a nitrogen atom in place of a ring oxygen and are competitive inhibitors of ER-resident alpha-glucosidases I and II.

In some embodiments of the methods and compositions of the invention, the alpha-glucosidase inhibitor comprises castanospermine (CAS No. 79831-76-8; a.k.a. (1S,6S,7R,8aR)-Tetrahydroxyoctahydroindolizine), acarbose (CAS No. 56180-94-0; a.k.a. 4",6"-Dideoxy-4"-([1S]-[1,4,6/5]-4,5,6-trihydroxy-3-hydroxymethyl-2-yclohexenylamino)-maltotriose), miglitol (CAS No. 72432-03-2; a.k.a. (2R,3R,4R,5S)-1-(2-Hydroxyethyl)-2-(2-hydroxymethyl)-3,4,5-piperidinetriol), voglibose (CAS No. 83480-29-9; a.k.a. 3,4-Dideoxy-4-[[2-hydroxy-1-(hydroxymethyl)ethyl]amino]-2-C-(hydroxymethyl)-D-epi-inositol), emiglitate (CAS No. 80879-63-6; a.k.a. ethyl 4-[2-[(2R,3R,4R,5S)-3,4,5-trihydroxy-2-(hydroxymethyl)piperidin-1-yl]ethoxy] benzoate), kotalanol (CAS No. 214491-0-73; a.k.a. 1,4-Dideoxy-1,4-[(S)-[7-deoxy-5-O-sulfo-D-glycero-D-galacto-heptitol-7-yl]episulfoniumylidene]-D-arabinitol inner salt), salacinol (CAS No. 200399-47-9; a.k.a. 1,4-Dideoxy-1,4-[(S)-[(2S,3S)-2,4-dihydroxy-3-(sulfooxy) butyl]episulfoniumylidene]-D-arabinitol inner salt); N-nonyl-deoxynojirimycin (NN-DNJ; CAS No. 81117-35-3) or a derivative of any of the foregoing that retains α-glucosidase inhibitory activity.

Figure 3:
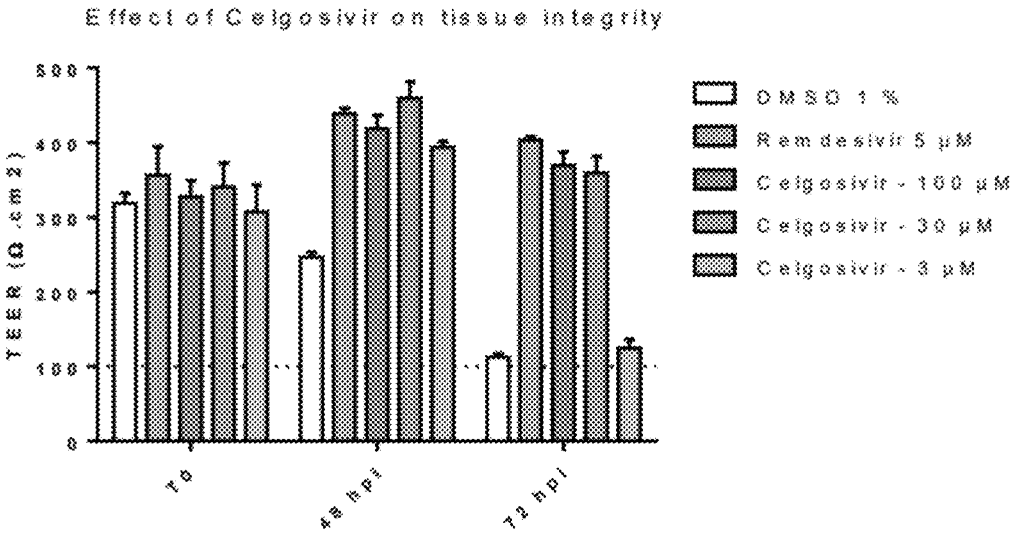
FIG. 3 shows effects of repeated (3 days) basolateral exposure to Celgosivir once a day on tissue integrity upon SARS-CoV-2 infection in MUCILAIR™-Pool (n=3 cultures). TEER was assessed before inoculation and 48, 72 hours post-inoculation. Threshold limit value is 100 Ω·cm$^2$. The initial TEER value in vehicle was in the normal range of MUCILAIR™ (200-600 Ohm·cm$^2$). SARS-CoV-2 infection reduced the TEER in vehicle at 48 and 72 hours, however epithelial barrier was not disrupted. In contrast, remdesivir treated cultures showed rather an increase of TEER values at 48 and 72 hours. SARS-CoV-2 induced decrease of TEER is prevented by 30 and 100 μM of Celgosivir.

Other alpha-glucosidase inhibitors that may be utilized include those disclosed in U.S. Pat. Nos. 4,065,562; 4,182,767; 4,278,683; 4,533,668; and 4,639,436; Mohana S et al. (2012), *International Journal of Antimicrobial Agents*, vol. 40, no. 3, pp. 273-276; Courageot M-P et al. (2000), *Journal of Virology*, vol. 74, no. 1, pp. 564-5'72; Warfield K L et al. (2016), *Antiviral Research*, vol. 129 pp. 93-98; Sayce A C et al. (2016), *PLOS Neglected Tropical Diseases*, vol. 10, issue 3, pp. 1-22; Krishnan M N and M A Garcia-Blanco, *Viruses* (2014), vol. 6, pp. 683-'708); Lu Y et al. (2014), *Molecules*, vol. 19, pp. 8544-8555, which are each incorporated reference in their entireties). Some general features of some representative classes of alpha-glucosidase inhibitors are shown and described in Gloster T M and G J Davies, *Org. Biomol. Chem.,* 2010, vol. 8, pp. 305-320, particularly FIG. 3, which is incorporated herein by reference in its entirety (FIG. 3 and the entire document).

Derivatives, Prodrugs, and Stereoisomers of Alpha-Glucosidase Glycoprotein Processing Inhibitors Derivatives of parent molecules that retain alpha-glucosidase inhibitory activity (the same activity, or different alpha-glucosidase activity in type or extent) are known and can be utilized (see, for example, Chapter 15, pp. 411-467, "Chemistry and Structure-Activity Relationships of Glucosidase Inhibitors", Jung B et al., in *Oral Antidiabetics*, Eds. Jochen Kuhlmann and Walter Puls, Springer-Verlag Berlin Heidelberg, 1996, which is incorporated herein by reference in its entirety). Analytical methods for detecting and identifying glucosidase inhibitors are known (see, for example, Chapter 16, pp. 483-494, "Analytical Methods of Determination of Glucosidase Inhibitors", Ploschke H J et al., in *Oral Antidiabetics,* 1996, which is incorporated herein by reference in its entirety). The pharmacology and metabolism of glucosidase inhibitors has been studied (see, for example, Chapter 17, pp. 497-525, "Pharmacology of Glucosidase Inhibitors", Puls W; and Chapter 18, pp. 535-538, "General Pharmacology of Glucosidase Inhibitors, Puls W; Chapter 19, pp. 541-554, "Pharmacokinetics and Metabolism of Glucosidase Inhibitors", Krause H P and H J Ahr; and Chapter 21, pp. 611-628, "Clinical Pharmacology of Glucosidase Inhibitors," Brendel E and W Wingender, in *Oral Antidiabetics,* 1996, which are each incorporated herein by reference in their entirety).

Derivatives of the alpha-glucosidase inhibitors exemplified herein can be synthesized by chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O(+)$, chlorination ($Cl_2$) bromination ($Br_2$), iodination ($I_2$), chlorohydrin formation ($Cl_2/H_2O$), bromohydrin formation ($Br_2/H_2O$), ether formation ($H^+$/ROH), oxymercuration ($Hg(OAc)_2/H_2O$), oxymercuration, ($Hg(OAc)_2$/ROH), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial, reduction ($Na/NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hoffmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $S_N2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+others), protection as silyl ethers, thiol formation ($S_N2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R-X plus catalyst), Friedel Crafts acylation (RCOX plus catalyst), iodination ($I_2$/catalyst), Side chain oxidation ($KMnO_4$), reduction of nitro groups, reduction of aromatic ketones, Side chain bromination, nucleophilic aromatic substitution ($S_NAr$), and aryne formation ($S_NAr$ via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation ($ROH/H^+$), acetal hydrolysis ($H_3O^+$), imine, formation ($RNH_2$), Enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles ($P_2O_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines ($LiAlH_4$), hydrolysis to carboxylic acids. Optionally, potential derivatives of alpha-glucosidase inhibitors exemplified herein, such as derivatives of castanospermine, can be tested for glycoprotein processing inhibition and/or anti-coronavirus virus activity using methods disclosed herein or using other methods known in the art.

By way of example only, castanospermine derivatives have been known for some time (Kang M S et al., "Castanospermine analogues: their inhibition of glycoprotein processing α-glucosidases from porcine kidney and B16F10 cells," *Glycobiology* (1995) 5 (1): 147-152; Winchester B G et at, "The structural basis of the inhibition of human glycosidases by castanospermine analogues," *Biochem. J.* (1990) 269, 227-231; Aguilar-Moncayo M et al., Glycosidase inhibition by ring-modified castanospermine analogues: tackling enzyme selectivity by inhibitor tailoring, *Org. Biomol. Chem.* (1999) 7:2738-47; Tyler P C and B G Winchester, Chapter 7, "Synthesis and Biological Activity of Castanospermine and Close Analogs", in Iminosugars as Glycosidase Inhibitors: Nojirimycin and Beyond, (ed A. E. Stütz), Wiley-VCH Verlag GmbH & Co. KGaA, Weinheim, FRG; U.S. Pat. No. 5,004,476 (Liu P S et al., "Antiretroviral castanospermine esters"); and U.S. Pat. No. 5,017,563 (Liu P S et al., "Castanospermine esters and glycosides"), which are each incorporated herein by reference in their entirety.

FIG. 1 shows a chemical structure illustrating an embodiment of alpha-glucosidase I inhibitors (also referred to as glucosidase I inhibitors), where $R_1$, $R_2$, $R_3$, $R_4$, and $R_5$, can be independently selected from the group consisting of: a H; F; Cl; Br; I; OH; CN; ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR_6$); and ester (—$COOR_7$ and —$OC(=O)R_7$);

where $R_6$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl; and where $R_7$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl.

The structure of FIG. 1 encompasses castanospermine and some derivatives of castanospermine. In one embodiment, the derivative of castanospermine in FIG. 1 is celgosivir (wherein $R_1$ would be ester (—$OC(=O)R_7$) with $R_7$ is n-propyl; R2, R3, and R5 is OH; and R4 is H).

Figure 2:
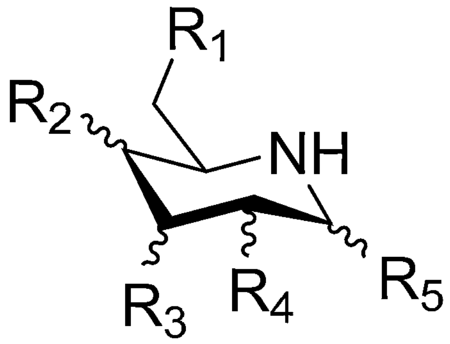
FIG. 2 shows a chemical structure illustrating an embodiment of alpha-glucosidase I inhibitors (also referred to as glucosidase I inhibitors). The structure of FIG. 2 encompasses nojirimycin and some derivatives of nojirimycin.

FIG. 2 shows a chemical structure illustrating an embodiment of alpha-glucosidase I inhibitors (also referred to as glucosidase I inhibitors), where $R_1$, $R_2$, $R_3$, $R_4$, and $R_5$, can be independently selected from the group consisting of: a H; F; Cl; Br; I; OH; CN; ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR_6$); and ester (—$COOR_7$ and —$OC(=O)R_7$);

where $R_6$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl; and where $R_7$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

The structure of FIG. 2 encompasses nojirimycin and some derivatives of nojirimycin. In one embodiment, the derivative of nojirimycin in FIG. 2 is 1-Deoxynojirimycin (DNJ) (wherein R1, R2, R3, and R4 are OH, and R5 is H).

Depending upon their molecular structure, the alpha-glucosidase inhibitors can be chiral and can accordingly occur in various enantiomeric forms. They can therefore exist in racemic or in optically active form.

Since the pharmaceutical activity of the racemates or stereoisomers of the alpha-glucosidase inhibitors may differ, it may be desirable to use the enantiomers. In these cases, the end product or even the intermediates can be separated into enantiomeric compounds by chemical or physical measures known to the person skilled in the art or even employed as such in the synthesis.

Any reference herein to a specific compound (e.g., castanospermine) should be understood as a reference to any enantiomer or mixture thereof. Any enantiomer may be substantially free of others, e.g., in an enantiomeric excess of at least 80%, preferably at least 90% and more preferably at least 95%. Similarly, any mixture of diastereomers may be substantially free of the other.

By way of example only, methods for synthesis of castanospermine enantiomers are known in the art (see, for example, Tiwari D K et al., "Divergent total synthesis of 1,6,8a-tri-epi-castanospermine and 1-deoxy-6,8a-di-epi-castanospermine from substituted azetidin-2-one (β-lactam), involving a cascade sequence of reactions as a key step", *Org Biomol Chem.* (2014) 12(37):7389-7396; Cesson J et al., "Asymmetric synthesis of (+)-castanospermine through enol ether metathesis-hydroboration/oxidation", Organic & Biological Chemistry, 2009, Issue 10; R C Bernotas and B. Ganem, "Total syntheses of (+)-castanospermine and (+)deoxynojirimycin," *Tetrahedron Lett* (1984) 25:165-168; Burgess K, "Synthetic approaches to stereoisomers and analogues of castanospermine," Tetrahedron, 48(20):4045-4066; and Burgess K et al., "A route to several stereoisomers of castanspermine, Journal of Organic Chemistry (1992), 57(4):1103-1109, each of which are incorporated herein by reference in their entirety).

Nucleic Acid and Polypeptide Inhibitors of Alpha-Glucosidase Glycoprotein Processing Nucleic acids useful in the invention include sequences encoding any protein that decreases synthesis or amounts of alpha-glucosidase, or that directly or indirectly contributes to a lack of alpha-glucosidase production or accumulation. Such sequences therefore include inhibitory nucleic acids such as antisense molecules and interfering RNA (e.g., siRNA, shRNA).

Additional nucleic acid sequences useful in the invention include sequences encoding proteins that directly or indirectly modulate expression or activity of any protein that participates in alpha-glucosidase accumulation. Particular examples include proteins that reduce expression or activity of alpha-glucosidase enzyme. Such sequences therefore include proteins that regulate transcription or translation of alpha-glucosidase enzyme. Accordingly, nucleic acids encoding such proteins or targeting such proteins for inhibition can also be used in accordance with the invention.

The terms "nucleic acid" and "polynucleotide" refer to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. A nucleic acid molecule may belong exclusively or in a mixture to any group of nucleotide-containing molecules, as exemplified by, but not limited to: RNA, DNA, cDNA, genomic nucleic acid, non-genomic nucleic acid, naturally occurring and non-naturally occurring nucleic acid and synthetic nucleic acid.

Nucleic acids can be of any length. Nucleic acid lengths useful in the invention typically range from about 20 nucleotides to 20 Kb, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length. Shorter polynucleotides are commonly referred to as "oligonucleotides" or "probes" of single- or double-stranded DNA. However, there is no upper limit to the length of such oligonucleotides.

Polynucleotides include L- or D-forms and mixtures thereof, which additionally may be modified to be resistant to degradation when administered to a subject. Particular examples include 5' and 3' linkages that are resistant to endonucleases and exonucleases present in various tissues or fluids of a subject.

Nucleic acids include antisense. As used herein, the term "antisense" refers to a polynucleotide or peptide nucleic acid capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA. For example, a single stranded nucleic acid can target an alpha-glucosidase transcript (e.g., mRNA). Antisense molecules are typically 100% complementary to the sense strand but can be "partially" complementary, in which only some of the nucleotides bind to the sense molecule (less than 100% complementary, e.g., 95%, 90%, 80%, 70% and sometimes less).

Triplex forming antisense can bind to double strand DNA thereby inhibiting transcription of the gene. Oligonucleotides derived from the transcription initiation site of the gene, e.g., between positions −10 and +10 from the start site, are a particular example.

Short interfering RNA (referred to as siRNA or RNAi) for inhibiting gene expression is known in the art (see, e.g., Kennerdell et al., *Cell* 95:1017 (1998); Fire et al., *Nature,* 391:806 (1998); WO 02/44321; WO 01/68836; WO 00/44895, WO 99/32619, WO 01/75164, WO 01/92513, WO 01/29058, WO 01/89304, WO 02/16620; and WO 02/29858). RNAi silencing can be induced by a nucleic acid encoding an RNA that forms a "hairpin" structure or by expressing RNA from each end of an encoding nucleic acid, making two RNA molecules that hybridize.

Ribozymes, which are enzymatic RNA molecules that catalyze the specific cleavage of RNA can be used to inhibit expression of the encoded protein. Ribozymes form sequence-specific hybrids with complementary target RNA, which is then cleaved. Specific examples include engineered hammerhead motif ribozyme molecules that can specifically and efficiently catalyze endonucleolytic cleavage of sequences encoding an alpha-glucosidase enzyme.

Ribozyme cleavage sites within a potential RNA target can be initially identified by scanning the target molecule for cleavage sites which include, for example, GUA, GUU, and GUC. Once identified, RNA sequences of between about 15 and 20 ribonucleotides corresponding to the region of the target containing the cleavage site are evaluated for secondary structural features which may render the oligonucleotide inoperable. The suitability of candidate target sequences may also be evaluated by testing accessibility to hybridization with complementary oligonucleotides using ribonuclease protection assays.

Antisense, ribozymes, RNAi and triplex forming nucleic acid are referred to collectively herein as "inhibitory nucleic acid" or "inhibitory polynucleotides." Such inhibitory nucleic acids can inhibit expression of an alpha-glucosidase enzyme.

Inhibitory polynucleotides do not require expression control elements to function in vivo. Such molecules can be absorbed by the cell or enter the cell via passive diffusion. Such molecules may also be introduced into a cell using a vector, such as a viral vector. Inhibitory polynucleotides may be encoded by a nucleic acid so that it is transcribed. Furthermore, such a nucleic acid encoding an inhibitory polynucleotide may be operatively linked to an expression control element for sustained or increased expression of the encoded antisense in cells or in vivo.

Inhibitory nucleic acid can be designed based on gene sequences available in the publicly available databases. For example, Genbank sequences for exemplary alpha-glucosidase enzymes are known in the art and can be used to design inhibitory nucleic acids.

Nucleic acids further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode amino acid sequences of alpha-glucosidase. Other examples are nucleic acids complementary to a sequence that encodes an amino acid sequence of an alpha-glucosidase enzyme.

Nucleic acid deletions (subsequences and fragments) can have from about 10 to 25, 25 to 50 or 50 to 100 nucleotides. Such nucleic acids are useful for expressing polypeptide subsequences, for genetic manipulation (as primers and templates for PCR amplification), and as probes to detect the presence or an amount of a sequence encoding a protein (e.g., via hybridization), in a cell, culture medium, biological sample (e.g., tissue, organ, blood or serum), or in a subject.

The term "hybridize" and grammatical variations thereof refers to the binding between nucleic acid sequences. Hybridizing sequences will generally have more than about 50% homology to a nucleic acid that encodes an amino acid sequence of a reference sequence. The hybridization region between hybridizing sequences can extend over at least about 10-15 nucleotides, 15-20 nucleotides, 20-30 nucleotides, 30-50 nucleotides, 50-100 nucleotides, or about 100 to 200 nucleotides or more.

Nucleic acids can be produced using various standard cloning and chemical synthesis techniques. Such techniques include, but are not limited to nucleic acid amplification, e.g. polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., microorganism, such as yeast or bacteria, a eukaryote such as an animal or mammalian cell or in a plant).

For expression or manipulation, nucleic acids can be incorporated into expression cassettes and vectors. Expression cassettes and vectors including a nucleic acid can be expressed when the nucleic acid is operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

Physical linkage is not required for the elements to be operably linked. For example, a minimal element can be linked to a nucleic acid encoding a glycogenic enzyme. A second element that controls expression of an operably linked nucleic acid encoding a protein that functions "in trans" to bind to the minimal element can influence expression of the glycogenic enzyme. Because the second element regulates expression of the glycogenic enzyme, the second element is operably linked to the nucleic acid encoding the glycogenic enzyme even though it is not physically linked.

The term "expression control element" refers to a nucleic acid that influences expression of an operably linked nucleic acid. Promoters and enhancers are particular non-limiting examples of expression control elements. A "promotor sequence" is a DNA regulatory region capable of initiating transcription of a downstream (3' direction) sequence. The promoter sequence includes nucleotides that facilitate transcription initiation. Enhancers also regulate gene expression, but can function at a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. Expression control elements that confer expression in response to a signal or stimuli, which either increases or decreases expression of the operably linked nucleic acid, are "regulatable." A regulatable element that increases expression of the operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, referred to as "tissue-specific expression control elements." Tissue-specific expression control elements are typically active in specific cell or tissue types because they are recognized by transcriptional activator proteins, or other regulators of transcription, that are active in the specific cell or tissue type as compared to other cell or tissue types.

For mammalian expression, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; the inducible mouse mammary tumor virus LTR) are used.

The invention methods, inter alia, therefore include introducing nucleic acid or protein into target cells, e.g., cells of a subject, for treatment or prevention of human coronavirus infection. Such cells are referred to as transformed cells. The term "transformed," when use in reference to a cell or organism, means a genetic change in a cell following incorporation of an exogenous molecule, for example, a protein or nucleic acid (e.g., a transgene) into the cell. Thus, a "transformed cell" is a cell into which, or a progeny of which an exogenous molecule has been introduced by the hand of man, for example, by recombinant DNA techniques. The nucleic acid or protein can be stably or transiently expressed in the transformed cell and progeny thereof. The transformed cell(s) can be propagated and the introduced protein expressed, or nucleic acid transcribed or encoded protein expressed. A progeny cell may not be identical to the parent cell, since there may be mutations that occur during replication.

Typically, cell transformation employs a "vector," which refers to a plasmid, virus, such as a viral vector, or other vehicle known in the art that can be manipulated by insertion or incorporation of a nucleic acid. For genetic manipulation "cloning vectors" can be employed, and to transcribe or translate the inserted polynucleotide "expression vectors" can be employed. Such vectors are useful for introducing nucleic acids, including nucleic acids that encode a glycogenic enzyme and nucleic acids that encode inhibitory nucleic acid, operably linked to an expression control element, and expressing the encoded protein or inhibitory nucleic acid (e.g., in solution or in solid phase), in cells or in a subject in vivo.

A vector generally contains an origin of replication for propagation in a cell. Control elements, including expression control elements as set forth herein, present within a vector, can be included to facilitate transcription and translation, as appropriate.

Vectors can include a selection marker. A "selection marker" is a gene that allows for the selection of cells containing the gene. "Positive selection" refers to a process in which cells that contain the selection marker survive upon exposure to the positive selection. Drug resistance is one example of a positive selection marker; cells containing the marker will survive in culture medium containing the selection drug, and cells lacking the marker will die. Selection markers include drug resistance genes such as neo, which confers resistance to G418; hygr, which confers resistance to hygromycin; and puro which confers resistance to puromycin. Other positive selection marker genes include genes that allow identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process in which cells containing a negative selection marker are killed upon exposure to an appropriate negative selection agent. For example, cells which contain the herpes simplex virus-thymidine kinase (HSV-tk) gene (Wigler et al., *Cell* 11:223 (1977)) are sensitive to the drug gancyclovir (GANC). Similarly, the gpt gene renders cells sensitive to 6-thioxanthine.

Viral vectors included are those based on retroviral, adeno-associated virus (AAV), adenovirus, reovirus, lentivirus, rotavirus genomes, simian virus 40 (SV40) or bovine papilloma virus (Cone et al., *Proc. Natl. Acad. Sci. USA* 81:6349 (1984); Eukaryotic Viral Vectors, Cold Spring Harbor Laboratory, Gluzman ed., 1982; Sarver et al., *Mol. Cell. Biol.* 1:486 (1981)). Adenovirus efficiently infects slowly replicating and/or terminally differentiated cells and can be used to target slowly replicating and/or terminally differentiated cells. Additional viral vectors useful for expression include parvovirus, Norwalk virus, coronaviruses, paramyxo- and rhabdoviruses, togavirus (e.g., sindbis virus and semliki forest virus) and vesicular stomatitis virus (VSV).

Mammalian expression vectors include those designed for in vivo and ex vivo expression, such as AAV (U.S. Pat. No. 5,604,090). AAV vectors have previously been shown to provide expression in humans at levels sufficient for therapeutic benefit (Kay et al., *Nat. Genet.* 24:257 (2000); Nakai et al., *Blood* 91:4600 (1998)). Adenoviral vectors (U.S. Pat. Nos. 5,700,470, 5,731,172 and 5,928,944), herpes simplex virus vectors (U.S. Pat. No. 5,501,979) retroviral (e.g., lentivirus vectors are useful for infecting dividing as well as non-dividing cells and foamy viruses) vectors (U.S. Pat. Nos. 5,624,820, 5,693,508, 5,665,577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed (U.S. Pat. Nos. 5,821,235, 5,786,340 and 6,110,456).

A viral particle or vesicle containing the viral or mammalian vector can be designed to be targeted to particular cell types (e.g., undesirably proliferating cells) by inclusion of a protein on the surface that binds to a target cell ligand or receptor. Alternatively, a cell type-specific promoters and/or enhancer can be included in the vector in order to express the nucleic acid in target cells. Thus, the viral vector itself, or a protein on the viral surface can be made to target cells for transformation in vitro, ex vivo or in vivo.

Introduction of compositions (e.g., alpha-glucosidase inhibitory compounds, proteins, and nucleic acids) into target cells can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly(methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (see, e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127).

Polymeric substances, microcapsules and colloidal dispersion systems such as liposomes are collectively referred to herein as "vesicles." Accordingly, viral and non-viral vector means of delivery into cells or tissue, in vitro, in vivo and ex vivo are included.

The terms "protein," "polypeptide" and "peptide" are used interchangeably herein to refer to two or more covalently linked amino acids, or "residues," through an amide bond or equivalent. Polypeptides are not limited by length and the amino acids may be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in Chemistry and Biochemistry of Amino Acids, Peptides and Proteins, Vol. 7, pp 267-357 (1983), "Peptide and Backbone Modifications," Marcel Decker, NY).

The term "isolated," when used as a modifier of a composition, means that the compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane. The term "isolated" does not exclude alternative physical forms, such as polypeptide multimers, post-translational modifications (e.g., phosphorylation, glycosylation) or derivatized forms.

An "isolated" composition can also be "substantially pure" when free of most or all of the materials with which it typically associates with in nature. Thus, an isolated molecule that also is substantially pure does not include polypeptides or polynucleotides present among millions of other sequences, such as antibodies of an antibody library or nucleic acids in a genomic or cDNA library, for example. A "substantially pure" molecule can be combined with one or more other molecules. Thus, the term "substantially pure" does not exclude combinations of compositions.

Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (nucleic acid and peptide).

Nucleic acids, proteins, agents and other compositions useful in accordance with the invention include modified forms as set forth herein, provided that the modified form retains, at least a part of, a function or activity of the unmodified or reference nucleic acid, protein, agent or composition. For example, a nucleic acid encoding a modified protein that inhibits alpha-glucosidase activity can retain sufficient alpha-glucosidase inhibitory activity (the modified protein can be used alone or in combination with another agent that inhibits alpha-glucosidase activity), but have increased or decreased activity relative to a reference unmodified alpha-glucosidase inhibitor.

Thus, the invention further employs proteins, nucleic acids, compounds, agents and other compositions having modifications of the exemplary proteins, nucleic acids, compounds, agents and compositions. As used herein, the term "modify" and grammatical variations thereof, when used in reference to a composition such as a protein, nucleic acid, agent, or other composition means that the modified composition deviates from a reference composition. Such modified proteins, nucleic acids, agents and other compositions may have greater or less activity than a reference unmodified protein, nucleic acid, agent or composition.

Polypeptide modifications include amino acid substitutions, additions and deletions, which are also referred to as "variants" in this context. Polypeptide modifications also include one or more D-amino acids substituted for L-amino acids (and mixtures thereof), structural and functional analogues, for example, peptidomimetics having synthetic or non-natural amino acids or amino acid analogues and derivatized forms.

Polypeptide modifications further include fusion (chimeric) polypeptide sequences, which is an amino acid sequence having one or more molecules not normally present in a reference native (wild type) sequence covalently attached to the sequence, for example, one or more amino acids. Modifications include cyclic structures such as an end-to-end amide bond between the amino and carboxy-terminus of the molecule or intra- or inter-molecular disulfide bond. Polypeptides including antibodies may be modified in vitro or in vivo, e.g., post-translationally modified to include, for example, sugar residues, phosphate groups, ubiquitin, fatty acids or lipids.

A "conservative substitution" is the replacement of one amino acid by a biologically, chemically or structurally similar residue. Biologically similar means that the substitution is compatible with biological activity, e.g., enzyme activity or alpha-glucosidase inhibitory activity. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

The term "identical" or "identity" means that two or more referenced entities are the same. Thus, where two protein sequences are identical, they have the same amino acid sequence. An "area of identity" refers to a portion of two or more referenced entities that are the same. Thus, where two protein sequences are identical over one or more sequence regions they share amino acid identity in that region. The term "substantial identity" means that the molecules are structurally identical or have at least partial function of one or more of the functions (e.g., a biological function) of the reference molecule. Polypeptides having substantial identity include amino acid sequences with 50%, 60%, 70%, 75%, 80%, 85%, 90%, 95%, 96%, 97%, 98%, or more identity to a reference polypeptide, provided that modified polypeptide has at least partial activity, e.g., inhibits alpha-glucosidase production, accumulation or activity.

As used herein, the term "subsequence" or "fragment" means a portion of the full length molecule. A protein subsequence has one or more fewer amino acids than a full length comparison sequence (e.g., one or more internal or terminal amino acid deletions from either amino or carboxy-termini). A nucleic acid subsequence has at least one less nucleotide than a full length comparison nucleic acid sequence. Subsequences therefore can be any length up to the full length molecule.

Modified forms further include derivatized sequences, for example, amino acids in which free amino groups form amine hydrochlorides, p-toluene sulfonyl groups, carbobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Modifications can be produced using any of a variety of methods well known in the art (e.g., PCR based site-directed, deletion and insertion mutagenesis, chemical modification and mutagenesis, cross-linking, etc.).

Polypeptide sequences can be made using recombinant DNA technology of polypeptide encoding nucleic acids via cell expression or in vitro translation, or chemical synthesis of polypeptide chains using methods known in the art. Polypeptide sequences can also be produced by a chemical synthesizer (see, e.g., Applied Biosystems, Foster City, Calif.).

Compositions and Treatment

The alpha-glucosidase inhibitors of the present invention can be formulated into pharmaceutically acceptable salt forms or hydrate forms. Pharmaceutically acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically acceptable base addition salts include sodium, potassium, calcium, ammonium, and magnesium salts. Pharmaceutically acceptable salts of the polypeptides of the invention can be prepared using conventional techniques.

Administration of one or more glucosidase inhibitors can be carried out in the form of an oral tablet, capsule, or liquid formulation containing a therapeutically effective amount of the active ingredient (alpha-glucosidase inhibitor). Administration is not limited to oral delivery and includes intravascular (e.g., intravenous), intramuscular, or another means known in the pharmaceutical art for administration of active pharmaceutical ingredients.

The bioavailability of alpha-glucosidases varies. For example, castanospermine is a relatively polar molecule with potentially low oral bioavailability. The invention contemplates the optional use of methods to increase oral bioavailability of the alpha-glucosidase through use of a variety of permeability enhancers known in the art or prodrugs capable of decreasing the molecule's polarity to stimulate absorption. For example, the prodrug celgosivir (6-O-butanoyl castanospermine) readily crosses cell membranes and is rapidly converted by endogenous esterases to castanospermine (Kang (1996) *Glycobiology,* 6, 206-216). On those inhibitors with a free hydroxyl group on the molecule, phosphorylation of the hydroxyl group is one method that may be utilized to produce a prodrug. The alpha-glucosidase inhibitors, including prodrugs, and methods for their production are described in U.S. Pat. No. 5,043,273 (Scudder P R et al.) and incorporated herein by reference in their entirety.

Therapeutic or prophylactic application of the alpha-glucosidase inhibitors, and compositions containing them, can be accomplished by any suitable therapeutic or prophylactic method and technique presently or prospectively known to those skilled in the art. The alpha-glucosidase inhibitors can be administered by any suitable route known in the art including, for example, oral, intramuscular, intraspinal, intracranial, nasal, rectal, parenteral, subcutaneous, or intravascular (e.g., intravenous) routes of administration. Administration of the alpha-glucosidase inhibitors of the invention can be continuous or at distinct intervals as can be readily determined by a person skilled in the art.

In some embodiments, an amount of alpha-glucosidase inhibitor (e.g., 100 mg-1,000 mg) is to be administered 1, 2, 3, 4, or times per day, for 1, 2, 3, 4, 5, 6, 7, or more days. Treatment can continue as needed, e.g., for several weeks. Optionally, the treatment regimen can include a loading dose, with one or more daily maintenance doses. For example, in some embodiments, an initial loading dose in the range of 100 mg to 1,000 is administered, followed by a maintenance dose in the range of 100 mg to 1,000 mg every 12 hours for 1, 2, 3, 4, 5, 6, or 7, or more days. In some embodiments, an initial loading dose in the range of 200 mg to 600 mg is administered, followed by a maintenance dose in the range of 100 mg to 300 mg every 12 hours for a total of 9 doses.

Alpha-glucosidase inhibitors and compositions comprising them can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive inhibitor is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject inhibitors include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the inhibitors can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the inhibitor based on the weight of the total composition including carrier or diluent.

The alpha-glucosidase inhibitors of the subject invention can also be administered utilizing liposome technology, slow release capsules, implantable pumps, and biodegradable containers. These delivery methods can, advantageously, provide a uniform dosage over an extended period of time.

The alpha-glucosidase inhibitors can also be modified by the addition of chemical groups, such as PEG (polyethylene glycol). PEGylated polypeptides typically generate less of an immunogenic response and exhibit extended half-lives in vivo in comparison to polypeptides that are not PEGylated when administered in vivo. Methods for PEGylating proteins and polypeptides known in the art (see, for example, U.S. Pat. No. 4,179,337). The subject polypeptides and polynucleotides can also be modified to improve cell membrane permeability. In one embodiment, cell membrane permeability can be improved by attaching a lipophilic moiety, such as a steroid, to the inhibitor. Other groups known in the art can be linked to the alpha-glucosidase inhibitors.

The subject invention also concerns a packaged dosage formulation comprising in one or more packages, packets, or containers at least one alpha-glucosidase inhibitor and/or composition of the subject invention formulated in a pharmaceutically acceptable dosage. The package can contain discrete quantities of the dosage formulation, such as tablet, capsules, lozenge, and powders. The quantity of alpha-glucosidase inhibitor in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg. In some embodiments, the amount is in the range of 100 mg to 600 mg, to be administered 1, 2, 3, or 4 times per day, for 2, 3, 4, 5, 6, 7 or more days.

The subject invention also concerns kits comprising in one or more containers an alpha-glucosidase inhibitor of the present invention. A kit of the invention can also comprise one or more compounds, biological molecules, or drugs. In one embodiment, a kit of the invention comprises an alpha-glucosidase inhibitor, and optionally comprises one or more of a drug or composition used in treating a viral infection (e.g., human coronavirus, such as SARS-CoV-2).

Optionally, the methods further comprise, prior to administering the alpha-glucosidase inhibitor to the subject, identifying the subject as having a human coronavirus infection (human coronavirus, generally, or a specific strain of coronavirus, such as SARS-CoV-2), or not having a human coronavirus infection. If the subject is identified as having a human coronavirus infection, the alpha-glucosidase inhibitor can be administered to the human subject as therapy. If the human subject is identified as not having a human coronavirus infection, the alpha-glucosidase inhibitor can be withheld, or the alpha-glucosidase inhibitor can be administered as prophylaxis, or an alternative agent can be given. The identifying step may comprise assaying a biological sample (e.g., blood, saliva, or urine) obtained from the subject for the presence of human coronavirus nucleic acids or human coronavirus proteins, such as SARS-CoV-2 nucleic acids or proteins. In some embodiments, assaying includes the use of reverse transcriptase-polymerase chain reaction (RT-PCR), immunological assay (e.g., ELISA), or Plaque-reduction neutralization testing (PRNT).

Thus, optionally, the methods include, prior to administration of the alpha-glucosidase inhibitor, or re-administration of the alpha-glucosidase inhibitor, determining whether the subject has a human coronavirus infection or one or more symptoms consistent with a human coronavirus infection. Some individuals infected with coronavirus will not know they have the infection because they will not have symptoms (i.e., are asymptomatic).

In some embodiments of the methods of the invention, the human coronavirus is SARS-CoV-2, or a variant of SARS-CoV-2, such as the B.1.1.7 variant, B.1.351 variant, and P.1 variant. SARS-CoV-2 is a novel human coronavirus that causes coronavirus disease 2019, also known as COVID-19 and COVID19.

SARS-CoV-2 has multiple variants currently circulating globally. Such SARS-CoV-2 variants include at least B.1.1.7 identified in the United Kingdom, B.1.351 identified in South Africa, and P.1 identified in travelers from Brazil. For example, SARS-CoV-2 variants may include mutations, such as the following: E484K, which was first discovered in the United Kingdom; L452R, which was detected in Denmark; and D614G discovered in China in January 2020.

In some embodiments, of the methods of the invention, the human coronavirus is selected from among SARS-CoV and MERS-CoV. MERS-CoV is the beta coronavirus that causes Middle East Respiratory Syndrome, or MERS. SARS-CoV is the beta coronavirus that causes severe acute respiratory syndrome, or SARS.

In some embodiments of the methods of the invention, the human coronavirus is a common human coronavirus, such as type 229E (an alpha coronavirus), NL63 (an alpha coronavirus), OC43 (a beta coronavirus), and HKU1 (a beta coronavirus).

The symptoms of a coronavirus infection depend on the type of coronavirus and severity of the infection. If a subject has a mild to moderate upper-respiratory infection, such as the common cold, symptoms may include: runny nose, headache, cough, sore throat, fever, and general feeling of being unwell. Some coronaviruses can cause severe symptoms. These infections may turn into bronchitis and pneumonia, which can cause symptoms such as fever (which can be quite high with pneumonia), cough with mucus, shortness of breath, and chest pain or tightness when the subject breaths or coughs.

The clinical spectrum of SARS-CoV-2 may range from mild disease with non-specific signs and symptoms of acute respiratory illness, to severe pneumonia with respiratory failure and septic shock. Asymptomatic infections have also been reported.

To diagnose coronavirus infections, healthcare providers typically take the subject's medical history and ask the subject their symptoms, do a physical examination, and may conduct laboratory tests on a biological sample such as blood, or a respiratory specimen such as sputum or a throat swab.

In some embodiments, a molecular assay may be used to detect the presence or absence of human coronavirus in a biological sample from the subject. For example, several assays that detect SARS-CoV-2 have been under development. Some assays may detect only the novel virus and some may also detect other strains (e.g., SARS-CoV) that are genetically similar. Table 1 below is a summary of some available protocols and their gene targets.

TABLE 1

Assay Protocols

| Country | Institution | Gene targets |
|---|---|---|
| United States | US CDC | Three N primers, RdRP |
| China | China CDC | ORF1ab and N |
| Germany | Charite' | RdRP, E, N |
| Hong Kong | HKU | ORF1b-nsp14, N |
| Japan | National Institute of Infection Diseases, Department of Virology III | Pancorona and multiple targets, Spike protein |
| Thailand | National Institute of Health | N |

China CDC Primers and probes for detection 2019-nCoV (24 Jan. 2020)

Diagnostic detection of Wuhan coronavirus 2019 by real-time RT-PCR—Charité, Berlin Germany (17 Jan. 2020)

Detection of 2019 novel coronavirus (2019-nCoV) in suspected human cases by RT-PCR—Hong Kong University (23 Jan. 2020)

PCR and sequencing protocol for 2019-nCoV—Department of Medical Sciences, Ministry of Public Health, Thailand (Updated 28 Jan. 2020)

PCR and sequencing protocols for 2019-nCoV-National Institute of Infectious Diseases Japan (24 Jan. 2020)

US CDC Real-Time RT-PCR Panel for Detection 2019-Novel Coronavirus (28 Jan. 2020)

US CDC panel primer and probes—U.S. CDC, USA (28 Jan. 2020)

("WHO interim guidance for laboratory testing for 2019 novel coronavirus (2019-nCoV) in humans" from World Health Organization website).

SARS-CoV-2 RNA has been detected from upper and lower respiratory tract specimens, and the virus has been isolated from upper respiratory tract specimens and bronchoalveolar lavage fluid. SARS-CoV-2 RNA has been detected in blood and stool specimens. The duration of SARS-CoV-2 RNA detection in the upper and lower respiratory tracts and in extrapulmonary specimens has not been determined. It is possible that RNA could be detected for weeks, which has occurred in some cases of MERS-CoV or SARS-CoV infection. Viable SARS-CoV has been isolated from respiratory, blood, urine, and stool specimens, and viable MERS-CoV has been isolated from respiratory tract specimens.

Treatment methods optionally include steps of advising that the subject get plenty of rest and drink fluids for hydration and administration of agents that alleviate symptoms of coronavirus infection, such as those that reduce fever and pain (e.g., acetaminophen and/or paracetamol), particularly for common human coronavirus infections. The methods may include administration of the fluids to the subject for hydration.

The human subject may be any age or gender. In the various embodiments, the human subject can be an adult or child. In some cases, the subject may be an infant or older adult. In some embodiments, the subject is 40 years of age or older. In some embodiments, the subject is 55 years of age or older. In some embodiments, the subject is 60 years of age or older. In some embodiments, the subject is an infant.

As used herein, a "child" refers to a human subject who is between the ages of 1 day to <18 years of age. The term "adult" refers to a human subject who is 18 years of age or older. In particular embodiments, the human subject is an adult of advanced age, such as an adult of 55 years of age or greater, 56 years of age or greater, 57 years of age or greater, 58 years of age or greater, 59 years of age or greater, 60 years of age or great, 61 years of age or greater, 62 years of age or greater, 63 years of age or greater, 64 years of age or greater, 65 years of age or greater, 66 years of age or greater, 67 years of age or greater, 68 years of age or greater, 69 years of age or greater, 70 years of age or greater, 75 years of age or greater, or 80 years of age or greater. Further, the plurality of human subjects may include adults or children. In some embodiments, the plurality of human subjects may include only adults. In another embodiment, the plurality of human subjects may include only children. In yet another embodiment, the plurality of human subjects may include both adults and children.

In some embodiments, the subject (of any age or gender) has heart or lung disease, or a weakened immune system.

In some embodiments, the subject has cancer at the time of administration of the alpha-glucosidase inhibitor. In other embodiments, the subject does not have cancer at the time of administration of the alpha-glucosidase inhibitor.

The invention further provides kits, including alpha-glucosidase inhibitors and pharmaceutical formulations, packaged into suitable packaging material, optionally in combination with instructions for using the kit components, e.g., instructions for performing a method of the invention. In one embodiment, a kit includes an amount of an alpha-glucosidase inhibitor, and instructions for administering the inhibitor to a subject in need of treatment on a label or packaging insert. In further embodiments, a kit includes an article of manufacture, for delivering the inhibitor into a subject locally, regionally or systemically, for example.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating a human coronavirus infection, an assay for identifying a subject having a human coronavirus infection, etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a human coronavirus infection. Instructions may additionally include appropriate administration route, dosage information, indications of a satisfactory clinical endpoint or any adverse symptoms that may occur, storage information, expiration date, or any information required by regulatory agencies such as the Food and Drug Administration or European Medicines Agency for use in a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing the alpha-glucosidase inhibitor. The kit can also include control components for assaying for the presence of human coronavirus, e.g., a control sample or a standard. Each component of the kit can be enclosed within an individual container or in a mixture and all of the various containers can be within single or multiple packages.

Dosing Regimen

The present invention pertains to methods of treating or preventing human coronavirus infection, or a symptom or disease resulting from a human coronavirus infection in the human subject. The methods involve administering an effective amount of an alpha-glucosidase glycoprotein processing inhibitor to the human subject.

In some embodiments, the methods of preventing or treating a human coronavirus infection or a symptom or disease resulting from a coronavirus infection, in a human subject comprise administering to a human subject at least one initial (loading) dose of a compound having a structure of FIG. 1, FIG. 2, Formula (I), Formula (II), and/or Formula (III), or a pharmaceutically acceptable salt of any of the foregoing, or a pharmaceutical composition comprising a compound having a structure of FIG. 1, FIG. 2, Formula (I), Formula (II), and/or Formula (III), or a pharmaceutically acceptable salt thereof, followed by administration of a plurality of subsequent doses of a compound of Formula (I), (II), and/or (III), or a pharmaceutically acceptable salt thereof, or a pharmaceutical composition comprising a compound of FIG. 1, FIG. 2, Formula (I), Formula (II), and/or Formula (III), or a pharmaceutically acceptable salt thereof. In further embodiments, the method further comprising administering a second agent (e.g., a drug) to said human subject.

In certain embodiments, the method is for prevention of a symptom or disease resulting from a coronavirus infection, such as those caused by any strain of viruses such as human coronavirus OC43 ("HCoV-OC43") (β-CoV), human coronavirus HKU1 ("HCoV-HKU1") (β-CoV), human coronavirus 229E ("HCoV-229E") (α-CoV), human coronavirus NL63 ("HCoV-NL63") (α-CoV), Middle East respiratory syndrome-related coronavirus ("MERS-CoV") (β-CoV), severe acute respiratory syndrome coronavirus ("SARS-CoV") (β-CoV), and SARS-CoV-2 (β-CoV). In such embodiments, the human subject may be asymptomatic for the coronavirus infection at the time of the administration and/or has been diagnosed as coronavirus negative at the time of the administration. Any suitable method for diagnosis or testing of a coronavirus infection can be used, and such methods are well known in the art, including nucleic acid assays. In further embodiments, the method further comprises administering a second drug to said human subject.

In certain embodiments, the method is for prevention of a symptom or disease resulting from an infection of any variant of SARS-CoV-2. In such embodiments, the human subject may be asymptomatic for SARS-CoV-2 infection at the time of the administration and/or has been diagnosed as SARS-CoV-2 infection negative at the time of the administration. Any suitable method for diagnosis or testing of SARS-CoV-2 infection can be used, and such methods are well known in the art, including nucleic acid assays.

In other embodiments, the method is for treatment of a coronavirus infection and/or treatment of a symptom or disease resulting from a coronavirus infection, such as those caused by any strain of viruses such as human coronavirus OC43 ("HCoV-OC43") (β-CoV), human coronavirus HKU1 ("HCoV-HKU1") (β-CoV), human coronavirus 229E ("HCoV-229E") (α-CoV), human coronavirus NL63 ("HCoV-NL63") (α-CoV), Middle East respiratory syndrome-related coronavirus ("MERS-CoV") (β-CoV), severe acute respiratory syndrome coronavirus ("SARS-CoV") (β-CoV), and SARS-CoV-2 (β-CoV). In such embodiments, the human subject may be symptomatic for a coronavirus infection at the time of the administration and/or the human subject may have been determined to be currently infected with a coronavirus at the time of the administration. In other embodiments, the human subject may be asymptomatic for a coronavirus infection and has been determined to be currently infected with a coronavirus at the time of the administration. In particular embodiments, the method further comprises detecting presence of a coronavirus infection prior to or concurrently with administration of the dosages of a compound of Formula (I), (II), and/or (III). In further embodiments, the method further comprises administering a second drug to said human subject.

In other embodiments, the method is for treatment of SARS-CoV-2 infection and/or treatment of COVID-19. In such embodiments, the human subject may be symptomatic for COVID-19 (e.g., SARS-CoV-2 infection) at the time of the administration and/or the human subject may have been determined to be currently infected with SARS-CoV-2 at the time of the administration. In certain embodiments, the human subject may be asymptomatic for SARS-CoV-2 infection and has been determined to be currently infected with SARS-CoV-2 at the time of the administration. In particular embodiments, the method further comprises detecting presence of SARS-CoV-2 infection prior to or concurrently with administration of the dosages of a compound of Formula (I), (II), and/or (III).

For both methods of treatment and method of prevention, in certain embodiments the method further comprises administering a second agent, such as a drug, to the human subject. In particular embodiments, the second agent is an antiviral drug, a monoclonal antibody treatment, a steroid, COVID-19 convalescent plasma, or a combination thereof. In further embodiments, the monoclonal antibody treatment is casirivimab, imdevimab, and/or bamlanivimab. In yet another embodiment, the antiviral drug is remdesivir, chloroquine, hydroxychloroquine, and/or favipiravir. In particular embodiments, the second agent is at least one selected from the group consisting of amikacin, amphotericin formulations, atovaquone, any azole-containing anti-fungal drug, Bactrim, clindamycin, corticosteroids, echinocandin, fluconazole, flucytosine, itraconazole, posaconazole, quinine, sulfa drugs, trimethoprimsulfamethoxazole, voriconazole, baricitinib, interleukin-6 inhibitors, kinase inhibitors, tyrosine kinsase inhibitors, Tocilizumab, ivermectin, any FDA approved drug for use in any coronavirus infection, and any combination thereof.

For both methods of treatment and methods of prevention, in certain embodiments the at least one initial (loading) dose comprises about 40 to 600 mg of a compound having the structure of FIG. 1, FIG. 2, Formula (I), Formula (II), and/or Formula (III), or a pharmaceutically acceptable salt thereof. In additional embodiments, each of the plurality of subsequent doses comprises about 25 to about 400 mg of a compound of Formula (I), (II), and/or (III), or a pharmaceutically acceptable salt thereof.

In certain embodiments, the total amount of alpha-glucosidase glycoprotein processing inhibitor, such as a compound of FIG. 1, FIG. 2, Formula (I), (II), and/or (III), or pharmaceutically acceptable salt thereof, does not exceed 600 mg per day. In other embodiments the total amount of a single administration of alpha-glucosidase glycoprotein processing inhibitor, such as a compound of FIG. 1, FIG. 2, Formula (I), (II), and/or (III), or pharmaceutically acceptable salt thereof, is 400 mg or less.

In further embodiments, the subsequent doses are administered at intervals of from about 6 to about 12 hours. In other embodiments, the subsequent doses are administered about every 6 hours, about every 8 hours, about every 12 hours, or about every 24 hours. In further embodiments, the subsequent doses are administered once, twice, three, four, or five times per day. In additional embodiments, the subsequent doses are administered for about 1-10 days, about 1-15 days, about 1-20 days, about 1-25 days, about 30 days, about four weeks, about six weeks, about eight weeks, about three months, about four months, about five months, about six months, about seven months, about eight months, about nine months, about ten months, about eleven months, or about one year. In other embodiments, the subsequent doses are administered for about 3-10 days, 3-15 days, 5-20 days, 5-30 days, 10-40 days, or 10-50 days.

In one embodiment, the compound of the invention is a compound of Formula (I):

(I)

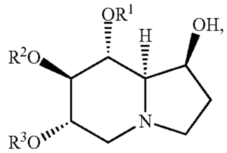

or a pharmaceutically acceptable salt there of;

wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

In another embodiment, R1 and R2 are H and R3 is a (C1-C14) acyl. In another embodiment, R1 is CH3-CH2CH2-C(O)—. In yet another embodiment, R2 is CH3-CH2CH2-C(O)—. In a further embodiment, R3 is CH3-CH2CH2-C(O)—. In another embodiment, at least one but not more than two R1, R2, and R3 is a hydrogen.

In yet another embodiment, the compound of the invention is a compound of
Formula (II):

(II)

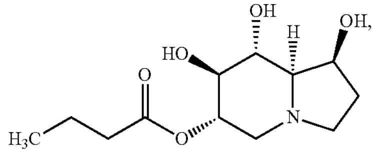

or a pharmaceutically acceptable salt thereof.

The compound of Formula (II), or pharmaceutical composition comprising a compound of Formula (II), can be used in any of the embodiments provided herein for Formula (I).

In further embodiment, the compound of the invention is a compound of Formula (III):

(III)

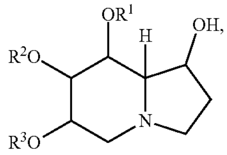

or a pharmaceutically acceptable salt there of;

wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

The compound of Formula (III), or pharmaceutical composition comprising a compound of Formula (III), can be used in any of the embodiments provided herein for Formula (I).

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention.

The compounds of the present invention can be administered as the free base or as a pharmaceutically acceptable salt. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estotate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. In one embodiment, the compound of Formula (I) is a hydrochloride salt. In another embodiment, the compound of Formula (II) is a hydrochloride salt.

The invention is also directed to methods of the invention using a pharmaceutical composition comprising a compound of FIG. 1, FIG. 2, Formula (I), Formula (II), and/or Formula (III), or a pharmaceutically acceptable salt of any of the foregoing. The disclosed compounds of FIG. 1, FIG. 2, Formula (I), Formula (II), and Formula (III), or a pharmaceutically acceptable salt of any of the foregoing, can be administered to the subject in conjunction with an acceptable pharmaceutical carrier or diluent as part of a pharmaceutical composition for prevention or treatment of a coronavirus infection, such as an infection from SARS-CoV-2 or any variant thereof, and/or a disease resulting from a coronavirus infection, such as COVID-19, and according to any of the dosing regimens described herein. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, PA Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In one embodiment, the pharmaceutical composition comprises a pharmaceutically acceptable carrier or diluent and an alpha-glucosidase glycoprotein processing inhibitor, such as a compound having the structure of FIG. 1, FIG. 2, Formula (I), Formula (II), and/or Formula (III), or a pharmaceutically acceptable salt of any of the foregoing.

In preferred embodiments, the compound is prodrug of castanospermine, a natural product derived from the seeds of Castanospermum australe. In another embodiment, the compound of Formula (I), (II), or (III) is converted to castanospermine after administration to a human subject. In yet another embodiment, a steady state Cmin serum or plasma concentration of between about 0.05 and about 2.0 microgram/mL of castanospermine in an adult or child human subject is attained. Compounds of Formula (I), (II), or (III) (e.g., celgosivir) are more rapidly and efficiently absorbed into cells than castanospermine. As a result, the claimed compounds may have higher EC50 values and in vivo efficacy than castanospermine against a coronavirus, such as SARS-CoV-2.

The human subject can be administered an alpha-glucosidase glycoprotein processing inhibitor of the present invention for a period of about between about 1 day to about one year. In one embodiment, the subsequent doses are administered for about 3 to about 180 days. In further embodiment, the subsequent doses are administered for about 30 to about 120 days. In another embodiment, the subsequent doses are administered for about 60 to about 90 days. In yet another embodiment, the subsequent doses are administered for about 90 to about 120 days. In another embodiment, the subsequent doses are administered for about 120 days to about six months.

In certain embodiments, the at least one initial dose comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 27, at least 28, at least 29, or at least 30 doses. In other embodiments, the at least one initial dose comprising one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, at most 24, at most 25, at most 27, at most 28, at most 29, or at most 30 doses. In some embodiments, two or more initial doses are administered at intervals of from about 6 to about 12 hours. In other embodiments, two or more initial doses are administered about every 6 hours, about every 8 hours, about every 12 hours, or about every 24 hours. In further embodiments, two or more initial doses are administered once, twice, three, four, or five times per day.

In certain embodiments, the beginning of the administration of the subsequent doses is within a day of administration of the at least one initial dose. In further embodiments, the beginning of the administration of the subsequent doses is about 20 hours, about 15 hours, about 12 hours, about 8 hours, or about 6 hours after administration of the at last one initial dose.

In certain embodiments, at least one initial dose is the same as the subsequent doses, while in other embodiments the at least one initial dose differs from the subsequent doses. In particular embodiments, the at least one initial dose is higher than the subsequent doses. In further embodiments, the at least one initial dose is the same dosage amount throughout the method. In other embodiments, the at least one initial dose varies dosage amounts throughout the method. In further embodiments, the plurality of subsequent doses is the same dosage amount throughout the method. In other embodiments, the plurality of subsequent doses varies dosage amounts throughout the method.

In certain embodiments, for an adult subject, the initial dose can be between about 40 to about 600 mg. In other embodiments, the initial dose in an adult subject can be about 75-600 mg, 100-600 mg, 150-600 mg, about 200-500 mg, or about 250-400 mg. In further embodiments, the initial dose in an adult subject can be about 40 mg, about 60 mg, about 80 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, or about 600 mg. In a further embodiment, the initial dose in an adult subject is between about 550 to about 600 mg. In another embodiment, the initial dose in an adult subject is between about 500 to about 550 mg. In yet another embodiment, the initial dose in an adult subject is between about 450 to about 500 mg. In a further embodiment, the initial dose in an adult subject is between about 400 to about 450 mg. In another embodiment, the initial dose in an adult subject is between about 350 to about 400 mg. In further embodiment, the initial dose in an adult subject is between about 300 to about 350 mg. In yet another embodiment, the initial dose in an adult subject is between about 250 to about 300 mg. In further embodiment, the initial dose in an adult subject is between about 200 to about 250 mg. In another embodiment, the initial dose in an adult subject is between about 150 to about 200 mg. In another embodiment, the initial dose in an adult subject is between about 100 to about 150 mg. In further embodiments, the initial dose in an adult subject is between about 50 to about 100 mg.

The subsequent doses in an adult subject can be between about 40 to about 400 mg. In one embodiment, the subsequent dose in an adult subject is between about 250 to about 300 mg. In another embodiment the subsequent dose in an adult subject is between about 200 to about 250 mg. In yet another embodiment, the subsequent dose in an adult subject is between about 150 to about 200 mg. In a further embodiment, the subsequent dose in an adult subject is between about 100 to about 200 mg. In other embodiments, the subsequent dose in an adult subject is between about 40 to about 80 mg. In even further embodiments, the subsequent dose in an adult subject is between about 80 to about 100 mg. In an additional embodiment, the subsequent dose in an adult subject is between about 125 to about 175 mg. In yet another embodiment, the subsequent dose in an adult subject is about 150 mg. In yet an additional embodiment, the subsequent dose in an adult subject is about 100 mg.

For a child subject, the initial dose in a child subject can be between about 15 to about 450 mg. In one embodiment, the initial dose in a child subject is between about 15 to about 25 mg. In another embodiment, the initial dose in a child subject is between about 25 to about 50 mg. In yet another embodiment, the initial dose in a child subject is between about 50 to about 75 mg. In still another embodiment, the initial dose in a child subject is between about 75 to about 100 mg. In further embodiment, the initial dose in a child subject is between about 100 to about 150 mg. In another embodiment, the initial dose in a child subject is between about 150 to about 200 mg. In yet another embodiment, the initial dose in a child subject is between about 200 to about 250 mg. In a further embodiment, the initial dose in a child subject is between about 250 to about 300 mg. In another embodiment, the initial dose in a child subject is between about 300 to about 350 mg. In yet another embodiment, the initial dose in a child subject is between about 350 to about 400 mg. In each instance, the dose can be administered as a single or split dose.

The subsequent doses in a child subject can be between about 25 to about 200 mg. In one embodiment, the subsequent dose in a child subject is between about 25 to about 50 mg. In another embodiment, the subsequent dose in a child subject is between about 50 to about 75 mg. In yet another embodiment, the subsequent dose in a child subject is between about 75 to about 100 mg. In further embodiment, the subsequent dose in a child subject is between about 100 to about 125 mg. In another embodiment, the subsequent dose in a child subject is between about 125 to about 150 mg. In yet another embodiment, the subsequent dose in a child subject is between about 150 to about 200 mg.

In certain particular embodiments, the child subject is less than one month of age. In particular embodiments, that <1-month old child subject receives an initial dose between about 15 to about 450 mg, or between about 15 to about 250 mg, as a single or split dose. In other embodiments, that <1-month old child receives subsequent doses between about 15 to about 250 mg, or between about 15 to about 250 mg, as single or split doses.

In certain embodiments of the invention, the initial dose(s) and/or the subsequent doses are administered three times per day, wherein each dose is about 167 mg to about 200 mg. In other embodiments, initial dose(s) and/or the subsequent doses are administered four times per day, wherein each dose is about 125 mg to about 150 mg. In one embodiment, the initial dose(s) and/or the subsequent doses are administered as two divided doses, wherein the total daily dose is about 225 mg to about 600 mg. In another embodiment, the initial dose(s) and/or the subsequent doses are administered as two divided doses, wherein the total daily dose is about 75 mg to about 600 mg. In other embodiments, the initial dose(s) and/or the subsequent doses are administered as two divided doses, wherein each dose is about 250 mg to about 300 mg. In yet another embodiment, the initial dose(s) and/or the subsequent doses are administered as one dose per day, wherein the total daily dose is about 40 mg to about 400 mg. In further embodiments, the initial dose(s) and/or the subsequent doses are administered as one dose per day, wherein each dose is about 225 mg to about 400 mg.

In another embodiment, the initial dose(s) and and/or subsequent doses are about 100 mg, about 120 mg, about 145 mg, about 150, about 170 mg, about 200, about 225 mg, about 240 mg, about 260 mg, about 280 mg, about 320 mg, about 340 mg, about 360 mg, about 380 mg, or about 400 mg and are administered to the human subject once a day. In other embodiments, the initial dose(s) and/or the subsequent doses are about 50 mg, about 60 mg, about 72 mg, about 75 mg, about 85 mg, about 100 mg, about 110 mg, about 225 mg, about 260 mg, about 280 mg, or about 300 mg and administered to the human subject twice a day. In further embodiments, the initial dose(s) and/or the subsequent doses are about 33 mg, about 40 mg, about 48 mg, about 50 mg, about 57 mg, about 67 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg and are administered to the human subject three times per day. In yet other embodiments, the initial dose(s) and/or the subsequent doses are about 25 mg, about 30 mg, about 36 mg, about 40 mg, about 50 mg, about 60 mg, about 70 mg, about 80 mg, about 90 mg, about 100 mg, about 110 mg, about 120 mg, about 130 mg, about 140 mg, about 150 mg and are administered to the human subject four times per day.

In one embodiment of the invention, the human subject is administered the initial dose(s) and/or the subsequent doses once per day, wherein each dose is about 3.8 mg/kg to about 6.7 mg/kg. In other embodiments, the human subject is administered the initial dose(s) and/or the subsequent doses twice per day, wherein each dose is about 4.2 mg/kg to about 5 mg/kg. In further embodiments, the human subject is administered the initial dose(s) and/or the subsequent doses three times per day, wherein each dose is about 2.8 mg/kg to about 3.33 mg/kg. In yet other embodiments, the human subject is administered the initial dose(s) and/or the subsequent doses four times per day, wherein each dose is about 2.1 mg/kg to about 2.5 mg/kg.

In one embodiment of the invention, the human subject is administered an initial dose of about 150 mg is administered a subsequent dose of about 100 mg every 6 hours for about 3 to about 30 days. In another embodiment, the human subject is administered an initial dose of about 150 mg and is administered a subsequent dose of about 100 mg every 6 hours for about 30 to about 90 days. In yet another embodiment, the human subject is administered an initial dose of about 150 mg and is administered a subsequent dose of about 100 mg every 6 hours for about 90 days to about six months. In further embodiment, the human subject is administered an initial dose of about 150 mg and is administered a subsequent dose of about 100 mg every 8 hours for about 3 to about 30 days. In certain embodiment, the human subject is administered an initial dose of about 150 mg and is administered a subsequent dose of about 100 mg every 8 hours for about 30 to about 90 days. In another embodiment, the human subject is administered an initial dose of about 150 mg and is administered a subsequent dose of about 100 mg every 8 hours for about 90 days to about six months. In yet another embodiment, the human subject is administered an initial dose of about 150 mg and is administered a subsequent dose of about 100 mg every 12 hours for about 3 to about 30 days. In another embodiment, the human subject is administered an initial dose of about 150 mg and is administered a subsequent dose of about 100 mg every 12 hours for about 30 to about 90 days. In further embodiment, the human subject is administered an initial dose of about 150 mg and is administered a subsequent dose of about 100 mg every 12 hours for about 90 days to about six months. In yet another embodiment, the human subject is administered an initial dose of about 150 mg and is administered a subsequent dose of about 100 mg once a day for about 3 to about 30 days. In another embodiment, the human subject is administered an initial dose of about 150 mg and is administered a subsequent dose of about 100 mg once a day for about 30 to about 90 days. In further embodiment, the human subject is administered an initial dose of about 150 mg and is administered a subsequent dose of about 100 mg once a day for about 90 days to about six months. In yet another embodiment, the human subject is administered an initial dose of about 150 mg and is administered a subsequent dose of about 150 mg every 6 hours for about 3 to about 30 days. In another embodiment, the human subject is administered an initial dose of about 150 mg and is administered a subsequent dose of about 150 mg every 6 hours for about 30 to about 90 days. In yet another embodiment, the human subject is administered an initial dose of about 150 mg and is administered a subsequent dose of about 150 mg every 6 hours for about 90 days to about six months. In another embodiment, the human subject is administered an initial dose of about 150 mg and is administered a subsequent dose of about 150 mg every 8 hours for about 3 to about 30 days. In certain embodiment, the human subject is administered an initial dose of about 150 mg and is administered a subsequent dose of about 150 mg every 8 hours for about 30 to about 90 days. In yet another embodiment, the human subject is administered an initial dose of about 150 mg and is administered a subsequent dose of about 150 mg every 8 hours for about 90 days to about six months. In one embodiment, the human subject is administered an initial dose of about 150 mg and is administered a subsequent dose of about 150 mg every 12 hours for about 3 to about 30 days. In further embodiment, the human subject is administered an initial dose of about 150 mg and is administered a subsequent dose of about 150 mg every 12 hours for about 30 to about 90 days. In yet another embodiment, the human subject is administered an initial dose of about 150 mg and is administered a subsequent dose of about 150 mg every 12 hours for about 90 days to about six months. In one embodiment, the human subject is administered an initial dose of about 150 mg and is administered a subsequent dose of about 150 mg once a day for about 3 to about 30 days. In further embodiment, the human subject is administered an initial dose of about 150 mg and is administered a subsequent dose of about 150 mg once a day for about 30 to about 90 days. In yet another embodiment, the human subject is administered an initial dose of about 150 mg and is administered a subsequent dose of about 150 mg once a day for about 90 days to about six months. In another embodiment, the human subject is administered an initial dose of about 150 mg and is administered a subsequent dose of about 200 mg every 6 hours for about 3 to about 30 days. In one embodiment, the human subject is administered an initial dose of about 150 mg and is administered a subsequent dose of about 200 mg every 6 hours for about 30 to about 90 days. In another embodiment, the human subject is administered an initial dose of about 150 mg and is administered a subsequent dose of about 200 mg every 6 hours for about 90 days to about six months. In further embodiment, wherein the human subject is administered an initial dose of about 150 mg and is administered a subsequent dose of about 200 mg every 8 hours for about 3 to about 30 days. In yet another embodiment, the human subject is administered an initial dose of about 150 mg and is administered a subsequent dose of about 200 mg every 8 hours for about 30 to about 90 days. In one embodiment, the human subject is administered an initial dose of about 150 mg and is administered a subsequent dose of about 200 mg every 8 hours for about 90 days to about six months. In another embodiment, the human subject is administered an initial dose of about 150 mg and is administered a subsequent dose of about 200 mg every 12 hours for about 3 to about 30 days. In further embodiment, the human subject is administered an initial dose of about 150 mg and is administered a subsequent dose of about 200 mg every 12 hours for about 30 to about 90 days. In another embodiment, the human subject is administered an initial dose of about 150 mg and is administered a subsequent dose of about 200 mg every 12 hours for about 90 days to about six months. In another embodiment, the human subject is administered an initial dose of about 150 mg and is administered a subsequent dose of about 200 mg once a day for about 3 to about 30 days. In further embodiment, the human subject is administered an initial dose of about 150 mg and is administered a subsequent dose of about 200 mg once a day for about 30 to about 90 days. In another embodiment, the human subject is administered an initial dose of about 150 mg and is administered a subsequent dose of about 200 mg once a day for about 90 days to about six months. In certain embodiment, the human subject is administered an initial dose of about 200 mg and is administered a subsequent dose of about 100 mg every 6 hours for about 3 to about 30 days. In yet another embodiment, the human subject is administered an initial dose of about 200 mg and is administered a subsequent dose of about 100 mg every 6 hours for about 30 to about 90 days. In another embodiment, the human subject is administered an initial dose of about 200 mg and is administered a subsequent dose of about 100 mg every 6 hours for about 90 days to about six months. In one embodiment, the human subject is administered an initial dose of about 200 mg and is administered a subsequent dose of about 100 mg every 8 hours for about 3 to about 30 days. In further embodiment, the human subject is administered an initial dose of about 200 mg and is administered a subsequent dose of about 100 mg every 8 hours for about 30 to about 90 days. In yet another embodiment, the human subject is administered an initial dose of about 200 mg and is administered a subsequent dose of about 100 mg every 8 hours for about 90 days to about six months. In another embodiment, the human subject is administered an initial dose of about 200 mg and is administered a subsequent dose of about 100 mg every 12 hours for about 3 to about 30 days. In one embodiment, the human subject is administered an initial dose of about 200 mg and is administered a subsequent dose of about 100 mg every 12 hours for about 30 to about 90 days. In another embodiment, the human subject is administered an initial dose of about 200 mg and is administered a subsequent dose of about 100 mg every 12 hours for about 90 days to about six months. In another embodiment, the human subject is administered an initial dose of about 200 mg and is administered a subsequent dose of about 100 mg once a day for about 3 to about 30 days. In one embodiment, the human subject is administered an initial dose of about 200 mg and is administered a subsequent dose of about 100 mg once a day for about 30 to about 90 days. In another embodiment, the human subject is administered an initial dose of about 200 mg and is administered a subsequent dose of about 100 mg once a day for about 90 days to about six months. In further embodiment, the human subject is administered an initial dose of about 200 mg and is administered a subsequent dose of about 150 mg every 6 hours for about 3 to about 30 days. In another embodiment of the invention, the human subject is administered an initial dose of about 200 mg and is administered a subsequent dose of about 150 mg every 6 hours for about 30 to about 90 days. In yet another embodiment, the human subject is administered an initial dose of about 200 mg and is administered a subsequent dose of about 150 mg every 6 hours for about 90 days to about six months. In another embodiment, the human subject is administered an initial dose of about 200 mg and is administered a subsequent dose of about 150 mg every 8 hours for about 3 to about 30 days. In one embodiment, the human subject is administered an initial dose of about 200 mg and is administered a subsequent dose of about 150 mg every 8 hours for about 30 to about 90 days. In yet another embodiment, the human subject is administered an initial dose of about 200 mg and is administered a subsequent dose of about 150 mg every 8 hours for about 90 days to about six months. In another embodiment, the human subject is administered an initial dose of about 200 mg and is administered a subsequent dose of about 150 mg every 12 hours for about 3 to about 30 days. In another embodiment, the human subject is administered an initial dose of about 200 mg is administered a subsequent dose of about 150 mg every 12 hours for about 30 to about 90 days. In an embodiment of the invention, the human subject is administered an initial dose of about 200 mg and is administered a subsequent dose of about 150 mg every 12 hours for about 90 days to about six months. In another embodiment, the human subject is administered an initial dose of about 200 mg and is administered a subsequent dose of about 150 mg once a day for about 3 to about 30 days. In another embodiment, the human subject is administered an initial dose of about 200 mg is administered a subsequent dose of about 150 mg once a day for about 30 to about 90 days. In an embodiment of the invention, the human subject is administered an initial dose of about 200 mg and is administered a subsequent dose of about 150 mg once a day for about 90 days to about six months. In further embodiment, the human subject is administered an initial dose of about 200 mg and is administered a subsequent dose of about 200 mg every 6 hours for about 3 to about 30 days. In yet another embodiment, the human subject is administered an initial dose of about 200 mg and is administered a subsequent dose of about 200 mg every 6 hours for about 30 to about 90 days. In another embodiment, the human subject is administered an initial dose of about 200 mg is administered a subsequent dose of about 200 mg every 6 hours for about 90 days to about six months. In an embodiment of the invention, the human subject is administered an initial dose of about 200 mg and is administered a subsequent dose of about 200 mg every 8 hours for about 3 to about 30 days. In further embodiment, the human subject is administered an initial dose of about 200 mg and is administered a subsequent dose of about 200 mg every 8 hours for about 30 to about 90 days. In yet another embodiment, the human subject is administered an initial dose of about 200 mg and is administered a subsequent dose of about 200 mg every 8 hours for about 90 days to about six months. In another embodiment, the human subject is administered an initial dose of about 200 mg and is administered a subsequent dose of about 200 mg every 12 hours for about 3 to about 30 days. In an embodiment of the invention, the human subject is administered an initial dose of about 200 mg and is administered a subsequent dose of about 200 mg every 12 hours for about 30 to about 90 days. In one embodiment, the human subject is administered an initial dose of about 200 mg and is administered a subsequent dose of about 200 mg every 12 hours for about 90 days to about six months. In another embodiment, the human subject is administered an initial dose of about 200 mg and is administered a subsequent dose of about 200 mg once a day for about 3 to about 30 days. In an embodiment of the invention, the human subject is administered an initial dose of about 200 mg and is administered a subsequent dose of about 200 mg once a day for about 30 to about 90 days. In one embodiment, the human subject is administered an initial dose of about 200 mg and is administered a subsequent dose of about 200 mg once a day for about 90 days to about six months. In another embodiment, the human subject is administered a single or a divided dose of about 25 to about 400 mg of the compound or the pharmaceutical composition, for about between about 3 days to about one year. In yet another embodiment, the human subject is administered a divided dose of about 25 to about 400 mg of the compound, or the pharmaceutical composition, for about between about 3 days to about one year.

Example embodiments of initial and subsequent doses in an adult are shown in Table 2. In certain such embodiments, subsequent doses can be administered from about every 8 hours to about every 96 hours, such as every 6 hours (four times a day), every 8 hours (three times a day), every 12 hours (twice a day), every 24 hours (once a day), every 48 hours (every other day), every 72 hours (every third day), or every 96 hours (every fourth day). In preferred embodiments, the total daily administered dose of the initial dose and the subsequent dose(s) does not exceed about 600 mg.

TABLE 2

Example Dosing Regimen for an Adult

| Embodiment | Initial dose (mg) | Subsequent dose (mg) |
|---|---|---|
| 1 | 100 | 100 |
| 2 | 150 | 100 |
| 3 | 200 | 100 |
| 4 | 250 | 100 |
| 5 | 300 | 100 |
| 6 | 350 | 100 |
| 7 | 400 | 100 |
| 8 | 450 | 100 |
| 9 | 500 | 100 |
| 10 | 550 | 100 |
| 11 | 600 | 100 |
| 12 | 100 | 150 |
| 13 | 150 | 150 |
| 14 | 200 | 150 |
| 15 | 250 | 150 |
| 16 | 300 | 150 |
| 17 | 350 | 150 |
| 18 | 400 | 150 |
| 19 | 450 | 150 |
| 20 | 500 | 150 |
| 21 | 550 | 150 |
| 22 | 600 | 150 |
| 23 | 600 | 175 |
| 24 | 100 | 200 |
| 25 | 150 | 200 |
| 26 | 200 | 200 |
| 27 | 250 | 200 |
| 28 | 300 | 200 |
| 29 | 350 | 200 |
| 30 | 400 | 200 |
| 31 | 450 | 200 |
| 32 | 500 | 200 |
| 33 | 550 | 200 |
| 34 | 600 | 200 |
| 35 | 100 | 250 |
| 36 | 150 | 250 |
| 37 | 200 | 250 |
| 38 | 250 | 250 |
| 39 | 300 | 250 |
| 40 | 350 | 250 |
| 41 | 400 | 250 |
| 42 | 450 | 250 |
| 43 | 500 | 250 |
| 44 | 500 | 250 |
| 45 | 550 | 250 |
| 46 | 600 | 250 |
| 47 | 100 | 300 |
| 48 | 150 | 300 |
| 49 | 200 | 300 |
| 50 | 250 | 300 |
| 51 | 300 | 300 |
| 52 | 350 | 300 |
| 53 | 400 | 300 |
| 54 | 450 | 300 |
| 55 | 450 | 300 |
| 56 | 500 | 300 |
| 57 | 500 | 300 |
| 58 | 550 | 300 |
| 59 | 600 | 300 |
| 60 | 100 | 350 |
| 61 | 150 | 350 |
| 62 | 200 | 350 |
| 63 | 250 | 350 |
| 64 | 300 | 350 |
| 65 | 350 | 350 |
| 66 | 400 | 350 |
| 67 | 450 | 350 |
| 68 | 450 | 350 |
| 69 | 500 | 350 |
| 70 | 500 | 350 |
| 71 | 550 | 350 |
| 72 | 600 | 350 |
| 73 | 100 | 400 |
| 74 | 150 | 400 |
| 75 | 200 | 400 |

TABLE 2-continued

Example Dosing Regimen for an Adult

| Embodiment | Initial dose (mg) | Subsequent dose (mg) |
|---|---|---|
| 76 | 250 | 400 |
| 77 | 300 | 400 |
| 78 | 350 | 400 |
| 79 | 400 | 400 |
| 80 | 450 | 400 |
| 81 | 450 | 400 |
| 82 | 500 | 400 |
| 83 | 500 | 400 |
| 84 | 550 | 400 |
| 85 | 600 | 400 |
| 60 | 40 | 25 |

Example embodiments of initial and subsequent doses combinations in a child are shown in Table 3. In certain such embodiments, subsequent doses can be administered from about every 6 hours to about every 96 hours, such as every 6 hours (four times a day), every 8 hours (three times a day), every 12 hours (twice a day), every 24 hours (once a day), every 48 hours (every other day), every 72 hours (every third day), or every 96 hours (every fourth day). In preferred embodiments, the total daily administered dose of the initial dose and the subsequent dose(s) does not exceed about 600 mg.

TABLE 3

Example Dosing Regimen for a Child

| Embodiment | Initial dose (mg) | Subsequent dose (mg) |
|---|---|---|
| 1 | 15 | 15 |
| 2 | 15 | 25 |
| 3 | 25 | 25 |
| 4 | 50 | 25 |
| 5 | 75 | 25 |
| 6 | 100 | 25 |
| 7 | 150 | 25 |
| 8 | 200 | 25 |
| 9 | 250 | 25 |
| 10 | 300 | 25 |
| 11 | 25 | 50 |
| 12 | 50 | 50 |
| 13 | 75 | 50 |
| 14 | 100 | 50 |
| 15 | 150 | 50 |
| 16 | 200 | 50 |
| 17 | 250 | 50 |
| 18 | 300 | 50 |
| 19 | 25 | 75 |
| 20 | 50 | 75 |
| 21 | 75 | 75 |
| 22 | 100 | 75 |
| 23 | 150 | 75 |
| 24 | 200 | 75 |
| 25 | 250 | 75 |
| 26 | 20 | 20 |
| 27 | 20 | 40 |
| 28 | 25 | 100 |
| 29 | 50 | 100 |
| 30 | 75 | 100 |
| 31 | 100 | 100 |
| 32 | 150 | 100 |
| 33 | 200 | 100 |
| 34 | 250 | 100 |
| 35 | 300 | 100 |
| 36 | 25 | 150 |
| 37 | 50 | 150 |
| 38 | 75 | 150 |
| 39 | 100 | 150 |
| 40 | 150 | 150 |

TABLE 3-continued

Example Dosing Regimen for a Child

| Embodiment | Initial dose (mg) | Subsequent dose (mg) |
|---|---|---|
| 41 | 200 | 150 |
| 42 | 250 | 150 |
| 43 | 300 | 150 |
| 44 | 25 | 200 |
| 45 | 50 | 200 |
| 46 | 75 | 200 |
| 47 | 100 | 200 |
| 48 | 150 | 200 |
| 49 | 200 | 200 |
| 50 | 250 | 200 |

The alpha-glucosidase glycoprotein processing inhibitors or pharmaceutical compositions of the present invention can be administered intravenously, orally, rectally, or sublingually. In one embodiment, the route of administration is intravenous. In another embodiment, the route of administration is oral. In another embodiment, the route of administration is rectal. In yet another embodiment, the route of administration is sublingual.

The alpha-glucosidase glycoprotein processing inhibitors or pharmaceutical compositions of the present invention can be administered as a single or as a divided dose. In some embodiments, the at least one initial dose can be single, divided, or a combination thereof. In some embodiments, the subsequent doses can be single, divided, or a combination thereof. For the subsequent doses in one embodiment, the human subject is administered a divided dose of from about 25 to about 400 mg for between about 3 to about 30 days. In another embodiment, the human subject is administered the subsequent doses as a single dose of from about 25 to about 400 mg for between about 3 to about 40 days. In yet another embodiment, the human subject is administered the subsequent doses as a single dose of from about 25 to about 400 for between about 3 day to about 60 days. In a further embodiment, the human subject is administered the subsequent doses as a single dose of from about 25 to about 400 mg for between about 3 days to about 60 days. In other versions, the subsequent doses are administered no longer than about 10 days; in yet other versions no longer than about 20 days; in further versions no longer than about 50 days; other versions no longer than about 100 days; and in other versions no longer than about one year.

It is known that a steady state minimum castanospermine concentration of 400 nanograms/ml is associated with a 50 mg/kg BID dose in mice and that the antiviral effect of celgosivir in vivo seems to be correlated with the minimum steady state concentration of castanospermine. Literature also shows that the pharmacokinetics of celgosivir is linear with dose over the tolerated dose range. International Publication No. WO 2014/143907 discloses pharmacokinetic parameters for castanospermine for the CELADEN study. Pharmacokinetic simulations using those pharmacokinetic parameters suggest that a 4× daily dose of 150 mg should produce a steady state minimum concentration of 1469 nanograms/ml, that a 3× daily dose of 200 mg results in an 799 nanograms/ml steady state minimum concentration of castanospermine, and that 300 mg twice daily results in a steady state minimum concentrations of castanospermine of 532 ng/ml. Extrapolating linearly, therefore, the minimum protective dose (achieving 400 nanograms/ml steady state minimum) is approximately 40 mg every 6 h, 75 mg every 8 h and 225 mg every 12 h. Further, WO 2014/143907 discloses that the CELADEN study regimen produce a steady state maximum castanospermine concentration of 5100 nanograms/ml. The adverse event profile in that study showed a higher incidence of GI effects, but not increased severity at that dose. That study also showed that in theory the maximum daily dose can be as high as 600 mg as a total dose, or 400 mg as a single dose, confirming literature to this effect. The FDA has published generic scaling factors to adjust mg/kg dosing in animals to mg/kg dosing in humans. Generically for mice, that scaling factor is 12. Therefore, 50 mg/kg BID is equivalent to a dose of 4.2 mg/kg BID in humans, which for a 60 kg human is equivalent to 250 mg. The same dose administered three or four times daily is equivalent to 167 mg and 125 mg and 2.8 and 2.1 mg/kg respectively. In a 60 kg human, the maximum single dose is 6.7 mg/kg, and the maximum daily dose is 10 mg/kg.

The invention also relates to methods of treating or preventing a coronavirus infection, such as an infection from SARS-CoV-2 or any variant thereof, and/or a symptom or disease resulting from the coronavirus infection, such as COVID-19, by achieving a steady state Cmin serum or plasma concentration of between about 0.05 and about 2.0 microgram/mL of castanospermine in an adult or child subject. In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In one embodiment, the minimum steady state concentration of castanospermine achieved exceeds 0.4 microgram/mL during administration of the initial dose(s) and/or subsequent doses to the human subject. In further embodiments, the minimum steady state concentration of castanospermine achieved exceeds 0.5 microgram/mL during administration of the initial dose(s) and/or subsequent doses to the human subject. In yet other embodiments, the minimum steady state concentration of castanospermine achieved exceeds 0.6 microgram/mL during administration of the initial dose(s) and/or subsequent doses to the human subject. In another embodiment, the minimum steady state concentration of castanospermine achieved exceeds 0.7 microgram/mL during administration of the initial dose(s) and/or subsequent doses to the human subject. In still other embodiments, the minimum steady state concentration of castanospermine achieved exceeds 0.8 microgram/mL during administration of the initial dose(s) and/or subsequent doses to the human subject. In other embodiments, the minimum steady state concentration of castanospermine achieved exceeds 0.9 microgram/mL during administration of the initial dose(s) and/or subsequent doses to the human subject. In yet another embodiment, the minimum steady state concentration of castanospermine achieved exceeds 1.0 microgram/mL during administration of the initial dose(s) and/or subsequent doses to the human subject. In some embodiments, the minimum steady state concentration of castanospermine achieved exceeds 1.1 microgram/mL during administration of the initial dose(s) and/or subsequent doses to the human subject. In another embodiment, the minimum steady state concentration of castanospermine achieved exceeds 1.2 microgram/mL during administration of the initial dose(s) and/or subsequent doses to the human subject. In yet another embodiment, the minimum steady state concentration of castanospermine achieved exceeds 1.3 microgram/mL during administration of the initial dose(s) and/or subsequent doses to the human subject. In still other embodiments, the minimum steady state concentration of castanospermine achieved exceeds 1.4 microgram/mL during administration of the initial dose(s) and/or subsequent doses to the human subject. In yet other embodiments, the minimum steady state concentration of castanospermine achieved does not exceed 2.0 microgram/mL during administration of the initial dose(s) and/or subsequent doses to the human subject.

In one embodiment, the average steady state Cmin serum or plasma concentration achieved in the plurality of human subjects is between about 0.08 and about 0.5 microgram/mL of castanospermine. In another embodiment, the average steady state Cmin serum or plasma concentration achieved in the plurality of human subjects is between about 0.05 and about 0.08 microgram/mL of castanospermine. In yet another embodiment, the average steady state Cmin serum or plasma concentration achieved in the plurality of human subjects is between about 0.08 and about 0.11 microgram/mL of castanospermine. In a further embodiment, the average steady state Cmin serum or plasma concentration achieved in the plurality of human subjects is between about 0.11 and about 0.4 microgram/mL of castanospermine. In another embodiment, the average steady state Cmin serum or plasma concentration achieved in the plurality of human subjects is between about 0.4 and about 0.75 microgram/mL of castanospermine. In further embodiment, the average steady state Cmin serum or plasma concentration achieved in the plurality of human subjects is between about 0.75 and about 1.0 microgram/mL of castanospermine. In yet another embodiment, the average steady state Cmin serum or plasma concentration achieved in the plurality of human subjects is between about 1.0 and about 2.0 microgram/mL of castanospermine. In another embodiment, the average steady state Cmin serum or plasma concentration achieved in the plurality of human subjects is between about 1.0 and about 1.5 microgram/mL of castanospermine. In further embodiment, the average steady state Cmin serum or plasma concentration achieved in the plurality of human subjects is between about 1.5 and about 2.0 microgram/mL of castanospermine. In yet another embodiment, the average steady state Cmin serum or plasma concentration achieved in the plurality of human subjects is between about 1.25 and about 1.75 microgram/mL of castanospermine.

In another aspect of the invention, viral load reduction of human subjects receiving the method of treatment is at least 50% greater than in persons not administered the compound or in placebo-administered groups. In one embodiment, the virological log reduction in human subjects receiving the method of treatment is at least 50% greater than in persons not administered the compound or in placebo-administered groups. In another embodiment, the virological log reduction in human subjects receiving the method of treatment is between about 60% to about 70% greater than in persons not administered the compound or in placebo-administered groups. In another embodiment, the virological log reduction in human subjects receiving the method of treatment is between about 70% to about 80% greater than in persons not administered the compound or in placebo-administered groups. In yet another embodiment, the virological log reduction in human subjects receiving the method of treatment is between about 80 to about 90% greater than in persons not administered the compound or in placebo-administered groups.

Exemplified Embodiments

Embodiment 1. A method for treating or preventing human coronavirus infection in a human subject, said method comprising administering an effective amount of an alpha-glucosidase glycoprotein processing inhibitor (also referred to as a alpha-glucosidase inhibitor) to a subject in need thereof.

Embodiment 2. The method of embodiment 1, wherein the human coronavirus is selected from among SARS-CoV-2 or variant thereof, SARS-CoV, and MERS-CoV.

Embodiment 3. The method of embodiment 1, wherein the human coronavirus I as common human coronavirus selected from among 229E, NL63, OC43, and HKU1.

Embodiment 4. The method of any preceding embodiment, wherein the alpha-glucosidase inhibitor comprises an alpha-glucosidase I inhibitor (also referred to as a glucosidase I inhibitor).

Embodiment 5. The method according to any preceding embodiment, wherein the subject has the coronavirus infection at the time of said administering.

Embodiment 6. The method according to any preceding embodiment, further comprises, prior to said administering, identifying the subject as having the coronavirus infection.

Embodiment 7. The method according to embodiment 6, wherein said identifying comprises assaying a biological sample (e.g., blood, saliva, urine) obtained from the subject for the presence of coronavirus nucleic acids or coronavirus proteins.

Embodiment 8. The method according to embodiment 7, wherein said assaying comprises use of reverse transcriptase-polymerase chain reaction (RT-PCR), immunological assay (e.g., ELISA), or Plaque-reduction neutralization testing (PRNT).

Embodiment 9. The method according to any one of embodiments 1 to 4, wherein the subject does not have the coronavirus infection at the time of said administering, and wherein the alpha-glucosidase inhibitor is administered as prophylaxis.

Embodiment 10. The method according to any one of embodiments 1 to 9, wherein the alpha-glucosidase inhibitor is administered orally, intravascularly (e.g., intravenously), nasally, rectally, parenterally, subcutaneously, or intramuscularly.

Embodiment 11. The method according to any one of embodiments 1 to 10, wherein the alpha-glucosidase inhibitor is one or more selected from among castanospermine, acarbose, miglitol voglibose, emiglitate, kotalanol, or a derivative or prodrug of any of the foregoing.

Embodiment 12. The method according to any one of embodiments 1 to 10, wherein the alpha-glucosidase inhibitor is castanospermine, a pharmaceutically acceptable salt thereof, or a derivative or prodrug thereof.

Embodiment 13. The method according to any one embodiments 1 to 10, wherein the alpha-glucosidase inhibitor is an alpha-glucosidase I inhibitor comprising castanospermine or celgosivir (6-O-butanoyl castanospermine).

Embodiment 14. The method according to embodiment 12 or 13, wherein the alpha-glucosidase inhibitor is administered orally or intravascularly (e.g., intravenously).

Embodiment 15. The method according to any one of embodiments 1 to 10, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 16. The method according to any one of embodiments 1 to 10, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 17. The method according to any one of embodiments 1 to 10, wherein the alpha-glucosidase inhibitor is a biologic (e.g., polypeptide, nucleic acid molecule, antibody), or small molecule drug.

Embodiment 18. The method according to any one of embodiments 1 to 10, wherein the alpha-glucosidase inhibitor comprises an antisense molecule, small interfering RNA (siRNA), or ribozyme targeting alpha-glucosidase in the subject and inhibits alpha-glucosidase production.

Embodiment 19. The method according to any preceding embodiment, further comprising administering another agent for treating or preventing coronavirus, or a symptom thereof, in the same formulation as the alpha-glucosidase inhibitor, or in a separate formulation before, during, or after administration of the alpha-glucosidase inhibitor.

Embodiment 20. The method according to any one of embodiments 1 to 10, wherein the alpha-glucosidase inhibitor includes an attached group that enhances cellular uptake of alpha-glucosidase inhibitor.

Embodiment 21. The method according to any preceding embodiment, wherein the alpha-glucosidase inhibitor is encapsulated in a liposome.

Embodiment 22. The method according to any preceding embodiment, wherein the alpha-glucosidase inhibitor further includes an attached polyethylene glycol group.

Embodiment 23. The method according to any preceding embodiment, wherein the alpha-glucosidase inhibitor includes an attached lipophilic moiety that provides for improved cell membrane permeability.

Embodiment 24. The method according to any preceding embodiment, wherein the alpha-glucosidase inhibitor includes a permeability enhancer that decreases the alpha-glucosidase inhibitor's polarity to facilitate absorption.

Embodiment 25. The method of any one of embodiments 1 to 4, further comprising determining that the human subject is infected with a coronavirus prior to or contemporaneously with initiating said administering.

Embodiment 26. The method of any one of embodiments 1 to 4, wherein the coronavirus is SARS-CoV-2 or a variant thereof, and the symptom thereof is a symptom of COVID-19.

Embodiment 27. The method of any one of embodiments 1 to 4, wherein the method is for treating a human coronavirus infection or a symptom thereof, and wherein said administering comprises:

(a) administering to the human subject at least one initial dose of about 15 mg to about 600 mg of the alpha-glucosidase glycoprotein processing inhibitor; and (b) administering to the human subject a plurality of subsequent doses of about 15 mg to about 400 mg of the alpha-glucosidase glycoprotein processing inhibitor, wherein not more than 600 mg of is administered per day, and wherein the subsequent doses are administered once, twice, three, or four times per day.

Embodiment 28. The method of embodiment 27, further comprising determining that the human subject is infected with a coronavirus prior to or contemporaneously with said administering of (a).

Embodiment 29. The method of any one of embodiments 1 to 4, wherein the method is for treating a human coronavirus infection or a symptom thereof, and wherein said administering comprises:

(a) determining that the human subject is infected with a coronavirus;

(b) administering to the human subject at least one initial dose of about 15 mg to about 600 mg of a compound of Formula (I) or a pharmaceutically acceptable salt thereof, or a pharmaceutical composition comprising about 15 mg to about 600 mg of a compound of Formula (I) or a pharmaceutically acceptable salt thereof; and (c) administering to the human subject a plurality of subsequent doses of about 15 mg to about 400 mg of a compound of Formula (I) or a pharmaceutically acceptable salt thereof, or a pharmaceutical composition comprising about 15 mg to about 400 mg of a compound of Formula (I) or a pharmaceutically acceptable salt thereof, wherein not more than 600 mg of a compound of Formula (I) is administered per day, wherein said subsequent doses are administered once, twice, three, or four times per day, and wherein Formula (I) has the following structure:

(I)

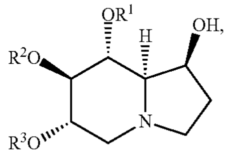

wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

Embodiment 30. The method of embodiment 29, wherein the compound of Formula (I) is a compound of Formula (II), or a pharmaceutically acceptable salt thereof:

(II)

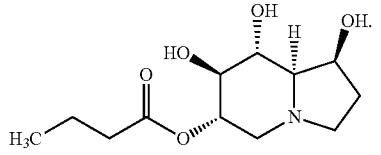

Embodiment 31. The method of any preceding embodiment, wherein the human subject is an adult.

Embodiment 32. The method of any preceding embodiment, wherein the human subject is at least 60 years of age.

Embodiment 33. The method of any one of embodiments 1-30, wherein the human subject is a child.

Embodiment 34. The method of any one of embodiments 29-33, wherein the compound of Formula (I) is converted to castanospermine after administration to the human subject, and wherein a steady state Cmin serum or plasma concentration of between about 0.4 and about 2.0 microgram/mL of castanospermine is attained in the human subject after administrations of initial and subsequent doses.

Embodiment 35. The method of embodiment 34, wherein a steady state Cmin serum or plasma concentration of between about 1.0 and about 2.0 microgram/mL of castanospermine is attained in the human subject after administrations of initial and subsequent doses; or wherein a steady state Cmin serum or plasma concentration of between about 1.0 and about 1.5 microgram/mL of castanospermine is attained in the human subject after administrations of initial and subsequent doses; or wherein a steady state Cmin serum or plasma concentration of between about 1.5 and about 2.0 microgram/mL of castanospermine is attained in the human subject after administrations of initial and subsequent doses; or wherein a steady state Cmin serum or plasma concentration of between about 1.25 and about 1.75 microgram/mL of castanospermine is attained in the human subject after administrations of initial and subsequent doses.

Embodiment 36. The method of any one of embodiments 27-35, wherein the compound, or the pharmaceutical composition, is administered orally or sublingually.

Embodiment 37. The method of any one of any one of embodiments 27-35, wherein the human subject is administered a subsequent dose of about 100 mg every 24 hours for between about 3 days to about 30 days; or wherein the human subject is administered a subsequent dose of about 150 mg every 24 hours for between about 3 days to about 30 days; or wherein the human subject is administered a subsequent dose of about 200 mg every 24 hours for between about 3 days to about 30 days; or wherein the human subject is administered a subsequent dose of about 250 mg every 24 hours for between about 3 days to about 30 days; or wherein the human subject is administered a subsequent dose of about 300 mg every 24 hours for between about 3 days to about 30 days; or wherein the human subject is administered a subsequent dose of about 350 mg every 24 hours for between about 3 days to about 30 days; or wherein the human subject is administered a subsequent dose of about 400 mg every 24 hours for between about 3 days to about 30 days; or wherein the human subject is administered an initial dose of about 150 mg and is administered a subsequent dose of about 100 mg every 6 hours, 8 hours, 12 hours, 24 hours for between about 3 days to about 30 days; or wherein the human subject is administered an initial dose of about 150 mg and is administered a subsequent dose of about 150 mg every 6 hours for between about 3 days to about 30 days; or wherein the human subject is administered an initial dose of about 150 mg and is administered a subsequent dose of about 150 mg every 8 hours for between about 3 days to about 30 days; or wherein the human subject is administered an initial dose of about 150 mg and is administered a subsequent dose of about 150 mg every 12 hours for between about 3 days to about 30 days; or wherein the human subject is administered an initial dose of about 150 mg and is administered a subsequent dose of about 150 mg every 24 hours for between about 3 days to about 30 days; or wherein the human subject is administered an initial dose of about 150 mg and is administered a subsequent dose of about 200 mg every 6 hours, 8 hours, 12 hours, or 24 hours for between about 3 days to about 30 days; or wherein the human subject is administered an initial dose of about 200 mg and is administered a subsequent dose of about 100 mg every 6 hours, 8 hours, 12 hours, or 24 hours for between about 3 days to about 30 days; or wherein the human subject is administered an initial dose of about 200 mg and is administered a subsequent dose of about 150 every 6 hours, 8 hours, 12 hours, or 24 hours for between about 3 days to about 30 days; or wherein the human subject is administered an initial dose of about 200 mg and is administered a subsequent dose of about 200 mg every 6 hours, 8 hours, 12 hours, or 24 hours for between about 3 days to about 30 days; or wherein the human subject is administered a single or a divided dose of about 25 to about 300 mg of the compound or the pharmaceutical composition, for between about 3 days to about 30 days.

Embodiment 36. The method of any preceding embodiment, wherein the method further comprises administering to the human subject a second agent (e.g., a drug).

Embodiment 37. The method of embodiment 36, wherein the second agent is an antiviral drug, a monoclonal antibody treatment, a steroid, and/or COVID-19 convalescent plasma.

Embodiment 38. The method of embodiment 37, wherein the monoclonal antibody treatment is casirivimab, imdevimab, and/or bamlanivimab, Embodiment 39. The method of embodiment 37, wherein the antiviral drug is remdesivir, chloroquine, hydroxychloroquine, and/or favipiravir.

Embodiment 40. The method of embodiment 37, wherein the second agent is selected from the group consisting of amikacin, amphotericin formulations, atovaquone, any azole-containing anti-fungal drug, Bactrim, clindamycin, corticosteroids, echinocandin, fluconazole, flucytosine, itraconazole, posaconazole, quinine, sulfa drugs, trimethoprim-sulfamethoxazole, voriconazole, baricitinib, interleukin-6 inhibitors, kinase inhibitors, tyrosine kinsase inhibitors, Tocilizumab, ivermectin, and any combination thereof.

Embodiment 41. The method of any one of embodiment 1 to 4, wherein the subject is asymptomatic at the time of initiating said administering.

Embodiment 42. The method of any one of embodiments 1 to 4, wherein the method is for preventing a human coronavirus infection or a symptom thereof, and wherein said administering comprises:

(a) administering to the human subject at least one initial dose of about 15 mg to about 600 mg of the alpha-glucosidase glycoprotein processing inhibitor; and (b) administering to the human subject a plurality of subsequent doses of about 15 mg to about 400 mg of the alpha-glucosidase glycoprotein processing inhibitor, wherein not more than 600 mg of is administered per day, wherein the human subject is asymptomatic at the time of administration of the at least one initial dose, and wherein the subsequent doses are administered once, twice, three, or four times per day.

Embodiment 43. The method of any one of embodiments 1 to 4, wherein the method is for preventing a human coronavirus infection or a symptom thereof, and wherein said administering comprises:

(a) administering to the human subject at least one initial dose of about 15 to about 600 mg of a compound of Formula (I) or a pharmaceutically acceptable salt thereof, or a pharmaceutical composition comprising about 15 to about 600 mg of a compound of Formula (I) or a pharmaceutically acceptable salt thereof and (b) administering to the human subject a plurality of subsequent doses of about 15 to about 400 mg of a compound of Formula (I) or a pharmaceutically acceptable salt thereof, or a pharmaceutical composition comprising about 15 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, wherein the subsequent doses are administered once, twice, three, or four times per day, and wherein Formula (I) has the following structure:

(I)

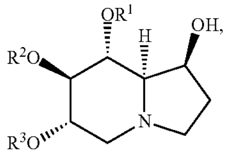

wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

Embodiment 44. The method of embodiment 43, wherein the compound of Formula (I), is a compound of Formula (II):

(II)

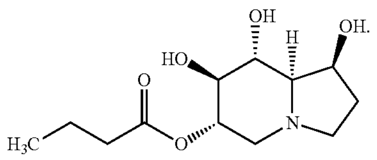

Embodiment 45. The method of embodiment 43 or 44, wherein the coronavirus is SARS-CoV-2 or a variant thereof, and/or the symptom is a symptom of COVID-19.

Embodiment 46. The method of embodiment 43, wherein the compound of Formula (I) is converted to castanospermine after administration to said human subject, and wherein a steady state Cmin serum or plasma concentration of between about 0.4 and about 2.0 microgram/mL of castanospermine is attained in the human subject after administrations of initial and subsequent doses.

Embodiment 47. The method of embodiment 43, wherein a steady state Cmin serum or plasma concentration of between about 1.0 and about 2.0 microgram/mL of castanospermine is attained in the human subject after administrations of initial and subsequent doses.

Embodiment 48. The method of embodiment 43, wherein a steady state Cmin serum or plasma concentration of between about 1.0 and about 1.5 microgram/mL of castanospermine is attained in the human subject after administrations of initial and subsequent doses; or wherein a steady state Cmin serum or plasma concentration of between about 1.5 and about 2.0 microgram/mL of castanospermine is attained in the human subject after administrations of initial and subsequent doses; or wherein a steady state Cmin serum or plasma concentration of between about 1.25 and about 1.75 microgram/mL of castanospermine is attained in the human subject after administrations of initial and subsequent doses.

Embodiment 49. The method of any one of embodiments 42 to 48, wherein the compound, or the pharmaceutical composition, is administered orally or sublingually.

Embodiment 50. The method of any one of embodiments 42 to 49, wherein the human subject is administered a subsequent dose of about 100 mg every 24 hours for between about 3 days to about 30 days; or wherein the human subject is administered a subsequent dose of about 150 mg every 24 hours for between about 3 days to about 30 days; or wherein the human subject is administered a subsequent dose of about 200 mg every 24 hours for between about 3 days to about 30 days; or wherein the human subject is administered a subsequent dose of about 250 mg every 24 hours for between about 3 days to about 30 days; or wherein the human subject is administered a subsequent dose of about 300 mg every 24 hours for between about 3 days to about 30 days; or wherein the human subject is administered a subsequent dose of about 350 mg every 24 hours for between about 3 days to about 30 days; or wherein the human subject is administered a subsequent dose of about 400 mg every 24 hours for between about 3 days to about 30 days; or wherein the human subject is administered an initial dose of about 150 mg and is administered a subsequent dose of about 100 mg every 6 hours, 8 hours, 12 hours, or 24 hours for between about 3 days to about 30 days; or wherein the human subject is administered an initial dose of about 150 mg and is administered a subsequent dose of about 150 mg every 6 hours for between about 3 days to about 30 days; or wherein the human subject is administered an initial dose of about 150 mg and is administered a subsequent dose of about 150 mg every 8 hours for between about 3 days to about 30 days; or wherein the human subject is administered an initial dose of about 150 mg and is administered a subsequent dose of about 150 mg every 12 hours for between about 3 days to about 30 days; or wherein the human subject is administered an initial dose of about 150 mg and is administered a subsequent dose of about 150 mg every 24 hours for between about 3 days to about 30 days; or wherein the human subject is administered an initial dose of about 150 mg and is administered a subsequent dose of about 200 mg every 6 hours, 8 hours, 12 hours, or 24 hours for between about 3 days to about 30 days; or wherein the human subject is administered an initial dose of about 200 mg and is administered a subsequent dose of about 100 mg every 6 hours, 8 hours, 12 hours, or 24 hours for between about 3 days to about 30 days; or wherein the human subject is administered an initial dose of about 200 mg and is administered a subsequent dose of about 150 every 6 hours, 8 hours, 12 hours, or 24 hours for between about 3 days to about 30 days; or wherein the human subject is administered an initial dose of about 200 mg and is administered a subsequent dose of about 200 mg every 6 hours, 8 hours, 12 hours, or 24 hours for between about 3 days to about 30 days; or wherein the human subject is administered a single or a divided dose of about 25 to about 300 mg of the compound or the pharmaceutical composition, for between about 3 days to about 30 days.

Embodiment 51. The method of any one of embodiments 42 to 50, wherein the method further comprises administering to the human subject a second agent (e.g., a drug).

Embodiment 52. The method of any one of embodiments 42 to 50, wherein the second drug is an antiviral drug, a monoclonal antibody treatment, a steroid, and/or COVID-19 convalescent plasma.

Embodiment 53. The method of embodiment 52, wherein the monoclonal antibody treatment is casirivimab, imdevimab, and/or bamlanivimab, Embodiment 54. The method of embodiment 52, wherein the antiviral drug is remdesivir, chloroquine, hydroxychloroquine, and/or favipiravir.

Embodiment 55. The method of embodiment 51, wherein the second agent is selected from the group consisting of amikacin, amphotericin formulations, atovaquone, any azole-containing anti-fungal drug, Bactrim, clindamycin, corticosteroids, echinocandin, fluconazole, flucytosine, itraconazole, posaconazole, quinine, sulfa drugs, trimethoprim-sulfamethoxazole, voriconazole, baricitinib, interleukin-6 inhibitors, kinase inhibitors, tyrosine kinsase inhibitors, Tocilizumab, ivermectin, and any combination thereof.

Embodiment 56. The method of any one of embodiments 42 to 51, wherein the method further comprises determining that the human subject has been exposed to a coronavirus or has had close contact with someone infected with a coronavirus.

Embodiment 57. The method of embodiment 56, wherein the determining step is performed prior to administering said initial dose.

Embodiment 58. A method for inhibiting a human coronavirus infection in a human cell, comprising contacting the infected human cell with alpha-glucosidase glycoprotein processing inhibitor in vitro or in vivo.

Embodiment 59. The method of embodiment 58, wherein the human coronavirus is SARS-CoV-2.

Embodiment 60. The method of embodiment 58, wherein the human coronavirus is a variant of SARS-CoV-2.

Embodiment 61. The method of embodiment 58, wherein the human coronavirus is selected from among SARS-CoV, MERS-CoV, 229E, NL63, OC43, and HKU1.

Embodiment 62. The method of any one of embodiments 58 to 61, wherein the alpha-glucosidase glycoprotein processing inhibitor comprises castanospermine, or a pharmaceutically acceptable salt, derivative, or prodrug thereof.

Embodiment 63. The method of embodiment 62, wherein the derivative or prodrug is administered, and the derivative or prodrug comprises celgosivir (6-O-butanoyl castanospermine) or a pharmaceutically acceptable salt thereof.

Embodiment 64. The method of any one of embodiments 58 to 61, wherein the alpha-glucosidase glycoprotein processing inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 65. The method of any one of embodiments 58 to 64, wherein the cell is contacted with the alpha-glucosidase glycoprotein processing inhibitor in vitro or in vivo prior to infection.

Embodiment 66. The method of any one of embodiments 58 to 64, wherein the cell is contacted with the alpha-glucosidase glycoprotein processing inhibitor in vitro or in vivo after infection.

Embodiment 67. A composition comprising an alpha-glucosidase inhibitor; and pharmaceutically acceptable buffer, carrier, or diluent.

Embodiment 68. The composition of embodiment 67, wherein the alpha-glucosidase inhibitor comprises an alpha-glucosidase I inhibitor (also referred to as a glucosidase I inhibitor).

Embodiment 69. The composition of embodiment 68, wherein the alpha-glucosidase inhibitor is one or more selected from among castanospermine, acarbose, miglitol voglibose, emiglitate, kotalanol, or a derivative or prodrug of any of the foregoing.

Embodiment 70. The composition of embodiment 68, wherein the alpha-glucosidase inhibitor is castanospermine, or a derivative or prodrug thereof.

Embodiment 71. The composition of embodiment 68, wherein the alpha-glucosidase inhibitor is an alpha-glucosidase I inhibitor comprising castanospermine or celgosivir (6-O-butanoyl castanospermine).

Embodiment 72. The composition of embodiment 68, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 73. The composition of embodiment 68, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 74. The composition of embodiment 68, wherein the alpha-glucosidase inhibitor is a biologic (e.g., polypeptide, nucleic acid molecule, antibody), or small molecule drug.

Embodiment 75. The composition of embodiment 68, wherein the alpha-glucosidase inhibitor comprises an antisense molecule, small interfering RNA (siRNA), or ribozyme targeting alpha-glucosidase in the subject and inhibits alpha-glucosidase production.

Embodiment 76. The composition of any one of embodiments 68 to 75, further comprising an additional agent effective for the treatment or prevention of coronavirus infection.

Embodiment 77. The composition of any one of embodiments 68 to 76, further comprising an additional agent effective for the treatment of one or more symptoms of coronavirus infection.

Embodiment 78. The composition of any one of embodiments 68 to 77, wherein the alpha-glucosidase inhibitor includes an attached group that enhances cellular uptake of alpha-glucosidase inhibitor.

Embodiment 79. The composition of any one of embodiments 68 to 78, wherein the alpha-glucosidase inhibitor is encapsulated in a liposome.

Embodiment 80. The composition of any one of embodiments 68 to 79, wherein the alpha-glucosidase inhibitor further includes an attached polyethylene glycol group.

Embodiment 81. The composition of any one of embodiments 68 to 80, wherein the alpha-glucosidase inhibitor includes an attached lipophilic moiety that provides for improved cell membrane permeability.

Embodiment 82. The composition of any one of embodiments 68 to 81, wherein the alpha-glucosidase inhibitor includes a permeability enhancer that decreases the alpha-glucosidase inhibitor's polarity to facilitate absorption.

Embodiment 83. A packaged dosage formulation comprising at least one alpha-glucosidase inhibitor in a pharmaceutically acceptable dosage in one or more packages, packets, or containers.

Embodiment 84. The packaged dosage formulation of embodiment 83, wherein the alpha-glucosidase inhibitor comprises an alpha-glucosidase I inhibitor (also referred to as a glucosidase I inhibitor).

Embodiment 85. The packaged dosage formulation of embodiment 84, wherein the alpha-glucosidase inhibitor is one or more selected from among castanospermine, acarbose, miglitol voglibose, emiglitate, kotalanol, or a derivative or prodrug of any of the foregoing.

Embodiment 86. The packaged dosage formulation of embodiment 84, wherein the alpha-glucosidase inhibitor is castanospermine, or a derivative or prodrug thereof.

Embodiment 87. The packaged dosage formulation of embodiment 84, wherein the alpha-glucosidase inhibitor comprises castanospermine or celgosivir (6-O-butanoyl castanospermine).

Embodiment 88. The packaged dosage formulation of embodiment 83, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 89. The packaged dosage formulation of embodiment 83, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 90. The packaged dosage formulation of embodiment 83, wherein the alpha-glucosidase inhibitor is a biologic (e.g., polypeptide, nucleic acid molecule, antibody), or small molecule drug.

Embodiment 91. The packaged dosage formulation of embodiment 83, wherein the alpha-glucosidase inhibitor comprises an antisense molecule, small interfering RNA (siRNA), or ribozyme targeting alpha-glucosidase in the subject and inhibits alpha-glucosidase production.

Embodiment 92. The packaged dosage formulation of embodiment 83, wherein said at least one alpha-glucosidase is provided as a tablet, capsule, lozenge, liquid, or powder.

Embodiment 93. The packaged dosage formulation of embodiment 83, further comprising an additional agent effective for the treatment or prevention of coronavirus infection.

Embodiment 94. The packaged dosage formulation of any one of embodiments 83 to 92, further comprising an additional agent effective for the treatment of one or more symptoms of coronavirus infection.

Embodiment 95. The packaged dosage formulation of any one of embodiments 83 to 93, wherein the alpha-glucosidase inhibitor includes an attached group that enhances cellular uptake of alpha-glucosidase inhibitor.

Embodiment 96. The packaged dosage formulation of any one of embodiments 83 to 95, wherein the alpha-glucosidase inhibitor is encapsulated in a liposome.

Embodiment 97. The packaged dosage formulation of any one of embodiments 83 to 96, wherein the alpha-glucosidase inhibitor further includes an attached polyethylene glycol group.

Embodiment 98. The packaged dosage formulation of any one of embodiments 83 to 97, wherein the alpha-glucosidase inhibitor includes an attached lipophilic moiety that provides for improved cell membrane permeability.

Embodiment 99. The packaged dosage formulation of any one of embodiments 83 to 97, wherein the alpha-glucosidase inhibitor includes a permeability enhancer that decreases the alpha-glucosidase inhibitor's polarity to facilitate absorption.

Embodiment 100. A kit comprising, in one or more containers, an alpha-glucosidase inhibitor.

Embodiment 101, wherein the alpha-glucosidase inhibitor comprises an alpha-glucosidase I inhibitor (also referred to as a glucosidase I inhibitor).

Embodiment 102. The kit of embodiment 100 or 101, further comprising instructions for administration of the alpha-glucosidase inhibitor for the treatment or prevention of human coronavirus infection.

Embodiment 103. The kit of one of embodiments 100 to 102, wherein the alpha-glucosidase inhibitor is one or more selected from among castanospermine, acarbose, miglitol voglibose, emiglitate, kotalanol, or a derivative or prodrug of any of the foregoing.

Embodiment 104. The kit of any one of embodiments 100 to 102, wherein the alpha-glucosidase inhibitor is castanospermine, or a derivative or prodrug thereof.

Embodiment 105. The kit of any one of embodiments 100 to 102, wherein the alpha-glucosidase inhibitor comprises castanospermine or celgosivir (6-O-butanoyl castanospermine).

Embodiment 106. The kit of embodiment 100, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 107. The kit of embodiment 100 to 102, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 108. The kit of any one of embodiments 100 to 102, wherein the alpha-glucosidase inhibitor is a biologic (e.g., polypeptide, nucleic acid molecule, antibody), or small molecule drug.

Embodiment 109. The kit of embodiment 100 to 108, wherein the alpha-glucosidase inhibitor comprises an antisense molecule, small interfering RNA (siRNA), or ribozyme targeting alpha-glucosidase in the subject and inhibits alpha-glucosidase production.

Embodiment 110. The kit of any one of embodiments 100 to 109, further comprising an additional agent effective for the treatment or prevention of human coronavirus infection.

Embodiment 111. The kit of any one of embodiments 100 to 110, further comprising an additional agent effective for the treatment of one or more symptoms of human coronaviruvirus infection.

Embodiment 112. The kit of any one of embodiments 100 to 111, wherein the alpha-glucosidase inhibitor includes an attached group that enhances cellular uptake of alpha-glucosidase inhibitor.

Embodiment 113. The kit of any one of embodiments 100 to 112, wherein the alpha-glucosidase inhibitor is encapsulated in a liposome.

Embodiment 114. The kit of any one of embodiments 100 to 113, wherein the alpha-glucosidase inhibitor further includes an attached polyethylene glycol group.

Embodiment 115. The kit of any one of embodiments 100 to 114, wherein the alpha-glucosidase inhibitor includes an attached lipophilic moiety that provides for improved cell membrane permeability.

Embodiment 116. The kit of any one of embodiments 100 to 115, wherein the alpha-glucosidase inhibitor includes a permeability enhancer that decreases the alpha-glucosidase inhibitor's polarity to facilitate absorption.

Definitions

As used herein, a subject is "in need of" a treatment if such human subject would benefit biologically, medically or in quality of life from such treatment (preferably, a human). In some embodiments, the subject has a coronavirus infection and is in need of therapy. In other embodiments, the subject does not have a coronavirus infection and is in need of prophylaxis. In some embodiments, the subject in need of prophylaxis is at risk of becoming infected with the coronavirus. In some embodiments, the subject is at increased risk of becoming infected with the coronavirus relative to others in the population.

As used herein, the terms "subject", "patient", and "individual" refer to a human of any age or gender.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

As used herein, the meaning of the phrase "close contact" in the context of a human having been exposed to someone infected with a coronavirus (e.g., SARS-CoV-2 or variant) is contact sufficient to transmit the coronavirus and will depend upon the exposure setting. The meaning may be the definition adopted by the government health agency having jurisdictional authority, and may be based on factors such as the presence of special populations. In some embodiments, close contact exists if the subject was within 6 feet of an infected person for a cumulative total of 15 minutes or more over a 24-hour period.

As used herein, the term "contacting" in the context of contacting a cell with at least one alpha-glucosidase inhibitor in vitro or in vivo means bringing at least one inhibitor into contact with the cell, or vice-versa, or any other manner of causing the inhibitor and the cell to come into contact.

The compounds of the present invention can be formulated into pharmaceutically-acceptable salt forms. Pharmaceutically-acceptable salts of the compounds of the invention can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, a "derivative" or "pharmaceutically active derivative" refers to any compound that upon administration to the recipient, is capable of providing directly or indirectly, the activity disclosed herein (e.g., anti-coronavirus activity and/or alpha-glucosidase inhibitory activity, such as inhibition of alpha-glucosidase I). The term "indirectly" also encompasses "prodrugs" which may be converted to the active form of the drug, e.g., via endogenous enzymes or metabolism (biotransformation). The prodrug is a derivative of the compounds according to the invention and presenting alpha-glucosidase inhibitory activity (e.g., alpha-glucosidase I inhibitory activity) that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g., by oxidation, reduction, hydrolysis or the like, each of which is carried out enzymatically. These compounds can be produced from compounds of the present invention according to well-known methods. The term "indirectly" also encompasses metabolites of compounds according to the invention. Chemical reactions, reactants, and reagents useful for making derivatives can be found, for example, in *March's Advanced Organic Chemistry,* $7^{th}$ edition, 2013, Michael B. Smith, which is incorporated herein by reference in its entirety.

More specifically, the term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, *Pharmaceuticals,* 2009, 2(3):77-81, which is incorporated by reference herein in its entirety).

The term "metabolite" refers to all molecules derived from any of the compounds according to the present invention in a cell or organism, preferably mammal. Pharmaceutically active metabolites of the compounds of the invention may be administered to a subject or contacted with a cell in vitro or in vivo.

The phrase "pharmaceutically acceptable" indicates that the substance or composition must be compatible chemically and/or toxicologically, with the other ingredients comprising a formulation, and/or the mammal being treated therewith.

Pharmaceutical formulations include "pharmaceutically acceptable" and "physiologically acceptable" carriers, diluents or excipients. In this context, the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions.

The phrase "effective amount" means an amount of an agent, such as an alpha-glucosidase inhibitor, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a subject is "in need of" a treatment if such human or non-human animal subject would benefit biologically, medically or in quality of life from such treatment (preferably, a human).

As used herein, the term "inhibit", "inhibition" or "inhibiting" refers to the reduction or suppression of a given condition, symptom, or disorder, or disease (e.g., coronavirus infection, or coronavirus viral load or titer), or a significant decrease in the baseline activity of a biological activity or process (e.g., alpha-glucosidase production, inhibitors of glycoprotein processing, and inhibitors of alpha-glucosidase activity such as alpha-glucosidase I activity).

The terms "compounds of the present invention" or "agents of the invention" (unless specifically identified otherwise) refer to alpha-glucosidase inhibitors including salts thereof, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

The term "a," "an," "the" and similar terms used in the context of the present invention (especially in the context of the claims) are to be construed to cover both the singular and plural unless otherwise indicated herein or clearly contradicted by the context. For example, the term "cell" includes a singular cell and a plurality of cells unless specified to the contrary; and the term "inhibitor" includes a singular inhibitor and a plurality of inhibitors.

"Alkyl" as used alone or as part of a larger moiety as in "arylalkyl" or "aryloxyalkyl" means a saturated aliphatic branched or straight-chain monovalent hydrocarbon radicals, typically C1-C16, preferably C1-C12. For example, "(C1-C6) alkyl" means a radical having from 1-6 carbon atoms in a linear or branched arrangement. "(C1-C6) alkyl" includes methyl, ethyl, propyl, butyl, tert-butyl, pentyl and hexyl.

"Alkylene" means a saturated aliphatic straight-chain divalent hydrocarbon radical. Thus, "(C1-C6) alkylene" means a divalent saturated aliphatic radical having from 1-6 carbon atoms in a linear arrangement. "(C1-C6) alkylene" includes methylene, ethylene, propylene, butylene, pentylene and hexylene.

"Cycloalkyl" means saturated aliphatic cyclic hydrocarbon ring. Thus, "C3-C8 cycloalkyl" means (3-8 membered) saturated aliphatic cyclic hydrocarbon ring. C3-C8 cycloalkyl includes, but is not limited to cyclopropyl, cyclobutyl, cyclopentyl, cyclohexyl, cycloheptyl, and cyclooctyl. Preferably, cycloalkyl is C3-C6 cycloalkyl.

The term "alkoxy" means —O-alkyl; "arylalkoxy" means an alkoxy group substituted at any carbon by an aryl group; "hydroxyalkyl" means alkyl substituted with hydroxy; "arylalkyl" means alkyl substituted with an aryl group; "alkoxyalkyl" mean alkyl substituted with an alkoxy group; "cycloalkylalkyl" means alkyl substituted with cycloalkyl; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O(C1-C6) alkyl and includes methoxy, ethoxy, propoxy, butoxy, pentoxy and hexoxy.

"Cycloalkoxy" means a cycloalkyl-O— group wherein the cycloalkyl is as defined above. Exemplary (C3-C7) cycloalkyloxy groups include cyclopropoxy, cyclobutoxy, cyclopentoxy, cyclohexoxy and cycloheptoxy.

"Halogen" and "halo" are interchangeably used herein and each refers to fluorine, chlorine, bromine, or iodine.

The terms "haloalkyl", "halocycloalkyl" and "haloalkoxy" mean alkyl, cycloalkyl, or alkoxy, as the case may be, substituted with one or more halogen atoms. The term "halogen" or "halo" means F, Cl, Br or I.

"Acyl" refers to R"—C(O)—, where R" is H, alkyl, substituted alkyl, heteroalkyl, substituted heteroalkyl, alkenyl, substituted alkenyl, aryl, alkylaryl, or substituted alkylaryl, and is indicated in the general formula of a particular embodiment as "Ac".

An "alkylene group" is represented by —[CH2]z-, wherein z is a positive integer, preferably from one to eight, more preferably from one to four.

An "alkenylene group" is an alkylene in which at least a pair of adjacent methylenes are replaced with —CH═CH—.

The term "(C6-C10) aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-10 ring atoms. A "substituted aryl group" is substituted at any one or more substitutable ring atom. The term "C6-C16 aryl" as used herein means a monocyclic, bicyclic or tricyclic carbocyclic ring system containing from 6 to 16 carbon atoms and includes phenyl (Ph), naphthyl, anthracenyl, 1,2-dihydronaphthyl, 1,2,3,4-tetrahydronaphthyl, fluorenyl, indanyl, indenyl and the like. The (C6-C10) aryl (C1-C6) alkyl group connects to the rest of the molecule through the (C1-C6) alkyl portion of the (C6-C10) aryl (C1-C6) alkyl group.

The term "Alkenyl" as used alone or as part of a larger moiety as in "Alkenylacyl" or "haloalkylacyl" means a straight or branched hydrocarbon radical having a specified number of carbon atoms and includes at least one double bond. An alkenyl group generally has between 2 and 6 carbon atoms. The (C6-C10) aryl (C2-C6) alkenyl group connects to the remainder of the molecule through the (C2-C6) alkenyl portion of (C6-C10) aryl (C2-C6) alkenyl.

"Alkenylacyl" refers to an acyl group, R"—C(O)–, where R" is an alkenyl or a substituted alkenyl (e.g., CH3-CH═CH—C(O)—).

"Pharmaceutically acceptable carrier" means non-therapeutic components that are of sufficient purity and quality for use in the formulation of a composition of the invention that, when appropriately administered to typically do not produce an adverse reaction, and that are used as a vehicle for a drug substance (e.g., a compound of Formula (I)).

"Three times a day dosing" or "three times per day," as used herein, refers to three administrations of a composition per every 24-hour period.

"Four times a day dosing" (QDS) or "four times per day," as used herein, refers to four administrations of a composition per every 24-hour period.

As used herein, "Cmin" refers to the minimum concentration that a drug achieves after the drug has been administered and prior to the administration of a second or additional dose. Further, "Cmax", as used herein, refers to the maximum concentration. Similarly, "Tmax", as used herein, refers to the time of maximum concentration. Additionally, "AUC", used herein, is the area under the concentration-time curve. Additionally, "50% effective concentration" (EC50), as used herein, refers to the concentration of an anti-viral that produces 50% of the maximal possible antiviral effect.

As used herein, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

As used herein, "viral load" refers to the amount of virus in the blood or other tissues, such as lung and respiratory tract, of a human subject.

As used herein, "initial dose" refers to the dose(s) which is administered to a human subject first in a dosing regimen. Further, "loading dose" and "initial dose" have the same meaning and are used interchangeably herein.

As used herein, "asymptomatic" refers to a human subject that may or may not have been exposed to a coronavirus, such as a variant of SARS-CoV-2, and does not present symptoms related to a coronavirus infection, such as a SARS-CoV-2 infection. An asymptomatic human subject may or may not be infected with a coronavirus, such as SARS-CoV-2. For example, an asymptomatic human subject includes a human subject that has no symptoms related to a SARS-CoV-2 infection and has been in close contact with someone that is infected with SARS-CoV-2. In another example, an asymptomatic human subject includes a human subject that has no symptoms related to a SARS-CoV-2 infection and has tested positive for infection of SARS-CoV-2.

As used herein, the terms "preventing" or "prevention" refers to achieving, partially, substantially, or completely, one or more of the following results: avoiding the disease, disorder, or syndrome resulting from a coronavirus infection, such as an infection from SARS-CoV-2 or a variant, such disease as COVID-19; avoiding clinical symptom or indicator associated with a disease, disorder, or syndrome resulting from a coronavirus infection, such as infection from SARS-CoV-2 or a variant; reducing the severity of the disease, disorder, or syndrome resulting from a coronavirus infection, such as from an infection of SARS-CoV-2 or a variant; or avoiding a coronavirus infection, such as an infection from SARS-CoV-2 or a variant.

The terms "strain" and "variant" in the context of viruses are used interchangeably herein to refer to subtypes of a virus that are genetically distinct from each other. For example, SARS-CoV-2 has multiple variants currently circulating globally. Such SARS-CoV-2 variants include at least B.1.1.7 identified in the United Kingdom, B.1.351 identified in South Africa, and P.1 identified in travelers from Brazil. For example, SARS-CoV-2 variants may include mutations, such as the following: E484K, which was first discovered in the United Kingdom; L452R, which was detected in Denmark; and D614G discovered in China in January 2020. Other mutations identified in SARS-CoV-2 variants include, for example, the 69/70 deletion, 144Y deletion, N501Y, A570D, P681H, E484K, and K417N/T.

EXAMPLES

Example 1: Celgosivir and Castanospermine are not Active Against a Number of Respiratory Viruses Celgosivir and castanospermine were evaluated for antiviral activity against a number of respiratory viruses using visual and neutral red cytopathic effect (CPE) assays as described below. EC50 was >300 microM for both compounds against the following viruses [see Table 4]: Human rhinovirus 14/1059, Influenza A H1N1/California/07/2009, Influenza H5 N1/Duck/MN/1525/81, Influenza B/Brisbane/60/2008, Influenza B/Florida/4/2006 and Parainfluenza virus 3/14702. Such EC50s are consistent with celgosivir and/or castanospermine not exhibiting useful in vivo or clinical efficacy.

Embryonic African green monkey kidney cells (MA-104), MDCK, or other cell lines were grown in minimal essential medium (MEM) supplemented with or without 0.1% NaHCO3 and 5-10% fetal bovine serum. When performing antiviral assays, serum was reduced to 2% and 50 mg/ml gentamicin was added to the medium with or without 10 U/mL trypsin and with or without 1 μg/mL of EDTA as required.

CPE inhibition assays with visual quantification of antiviral activity and cytotoxicity were performed as described by Sidwell, R. W. and Huffman, J. H. (1971) *Use of disposable micro-tissue culture plates for antiviral and interferon induction studies*. Appl. Microbiol. 22, 7979-7801, with slight modifications. Celgosivir and castanospermine at concentrations of 0.3, 3, 30 and 300 microM varying and virus at a multiplicity of infection (MOI)=0.001 were added to near confluent cell monolayers and incubated at 37° C. until the cells in the control wells showed complete viral CPE as observed by light microscopy. All compounds were assayed for virus inhibition in quadruplicate and for cytotoxicity in duplicate. For each compound, two wells were set aside as uninfected, untreated cell controls per test and four wells per test received virus only and represented controls for virus replication. Changes due to viral cytopathic effect were graded on a scale of 1-4, grade 4 representing a scenario in which the entire (100%) monolayer in a well showed viral cytopathic effect. For all CPE-based assays, the 50% effective concentration (EC50) was calculated by regression analysis using the means of the CPE ratings at each concentration of compound. Morphological changes due to compound cytotoxicity were graded on a scale of 0-5; grade 5 was defined as 100% cytotoxicity. The 50% cytotoxic dose (IC50) was calculated by regression analysis. A selective index (S.I.) was calculated for each compound (S.I.=(IC50)/(EC50)).

Neutral red assay of CPE inhibition and cytotoxicity was performed by a modified method as described by Cavenaugh, P. R., et al. *A semi-automated neutral red based chemosensitivity assay for drug screening*. (1990) Invest. New Drugs 8, 347-354. Briefly, medium was removed from each well of a plate scored for CPE from the visual CPE inhibition assay, 0.2 ml of neutral red (0.034% in PSS) was added to each of the wells of that plate and the plate incubated for 2 h at 37° C. in the dark. The neutral red solution was removed from the wells and the wells rinsed twice with PBS (pH 7.4). Equal volumes (0.1 ml) of absolute ethanol and Sorenson citrate buffer (0.1 M sodium citrate, 0.1 M HCl, pH 4.2) were mixed together and added to each well. Plates were incubated in the dark for 30 min at room temperature to solubilize the dye. The plates were then gently mixed on a 96-well plate adapted vortexer for 1 min. Absorbances at 540 and 450 nm were read with a microplate reader (Bio-Tek EL 1309; Bio-Tek Instruments). All concentrations were assayed at least in triplicate. Absorbance values were expressed as percentages of untreated controls and EC50 and IC50 values were calculated by regression analysis.

Ribavirin, used as a positive control, exhibited expected activity against all the virus lines [EC50<10 microM].

TABLE 4

Antiviral, cytotoxicity and selectivity data for celgosivir, castanospermine and ribavirin against respiratory viruses in vitro

| Compound | Virus | Cell Line | Assay Method | Concentration Range | EC50 | CC50 | SI |
|---|---|---|---|---|---|---|---|
| Celgosivir and castanospermine | Human rhinovirus 14/1059, Influenza A H1N1/California/07/2009, Influenza H5 N1/Duck/MN/1525/81, Influenza B/Brisbane/60/2008, Influenza B/Florida/4/2006, Parainfluenza virus 3/14702 | MA-104 or MDCK | Visual or Neutral Red | 0.3-300 | Not active | | |

Figure 4:
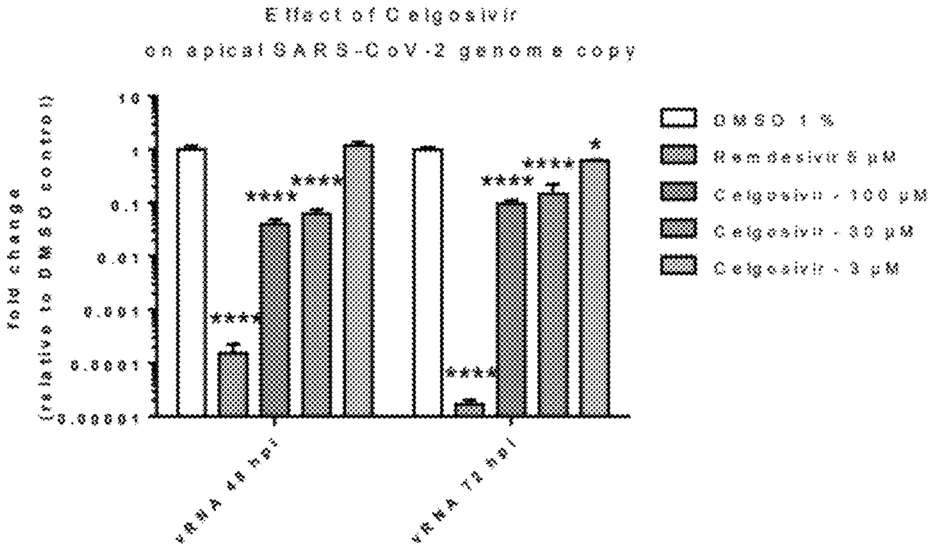
FIG. 4 shows effects of repeated (3 days) basolateral exposure to Celgosivir once a day on SARS-CoV-2 apical replication in MUCILAIR™-Pool (n=3 cultures). Data are expressed as fold change relative to DMSO 1% cultures. Statistical comparison was performed using two-way ANOVA with Dunnett's multiple comparison post-tests. The reference antiviral remdesivir reduced SARS-CoV-2 genome copies (ORF1b-nsp14) at apical side on MUCILAIR™ by a mean of 3.9 and 4.8 log 10 at 48 and 72 hours post-infection relative to vehicle control. Celgosivir showed a dose dependent inhibition of SARS-CoV-2 replication. Significant reductions of viruses, 1.2 and 1.4 log 10 were observed for 30 and 100 mM, respectively, at 48 hours. At the later time point, Celgosivir induced a reduction of 0.9 and 1 log 10 at 30 and 100 mM, respectively.
Figure 5A:
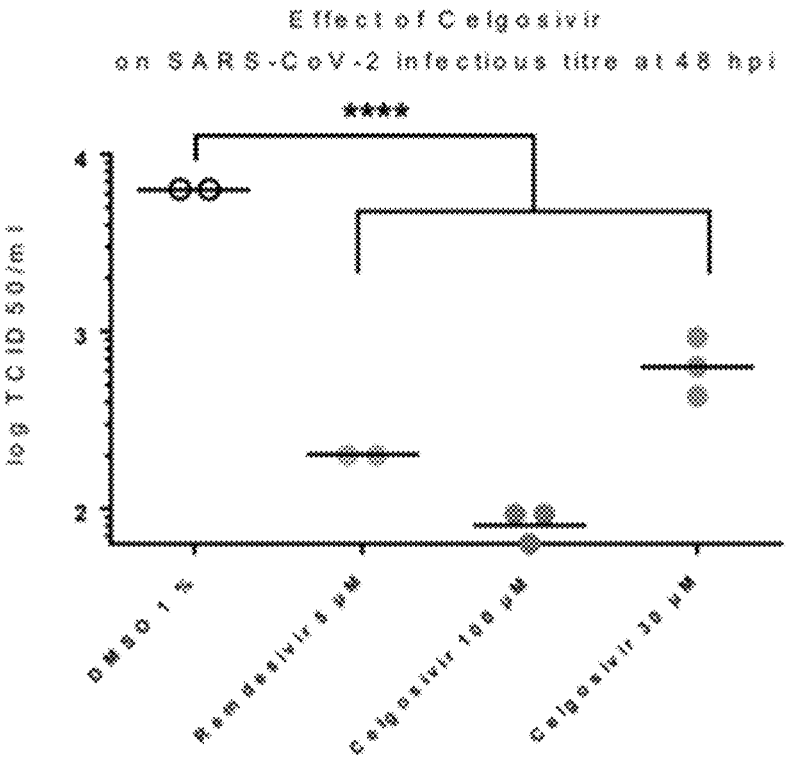
FIGS. 5A and 5B show effects of repeated (3 days) basolateral exposure to Celgosivir once a day on SARS-CoV-2 apical infectious titre in MUCILAIR™-Pool (n=3 cultures). Statistical comparison was performed daily using one-way ANOVA with Dunnett's multiple comparison post-tests. The reference antiviral remdesivir reduced SARS- CoV-2 titre at apical side on MUCILAIR™ by 1.5 and 0.9 log 10 at 48 and 72 hours post-infection relative to vehicle control. Celgosivir reduced SARS-CoV-2 titre at apical side on MUCILAIR™ at 48 hours by 1.9 and 1 log 10 at 100 and 30 mM. On the increased SARS-CoV-2 titre at 72 hours, the reducing effect of remdesivir and celgosivir was the same, 1.1 log.
Figure 5B:
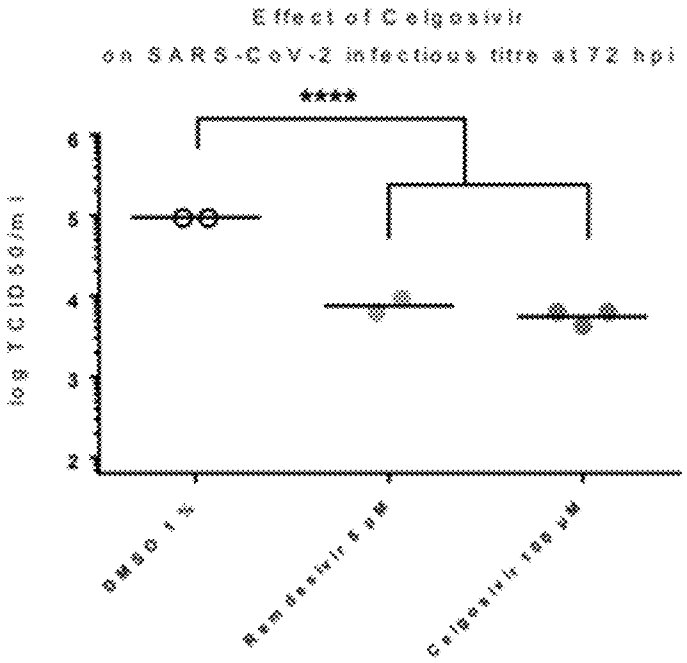
Figure 6A:
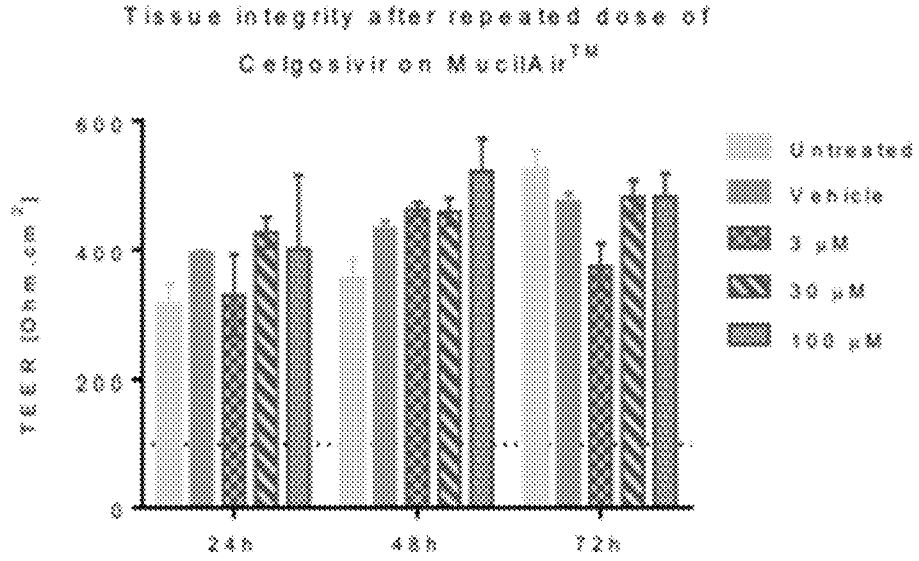
FIGS. 6A-6C show effect of repeated (3 days) basolateral exposure to Celgosivir on MUCILAIR™-Pool (n=3 cultures). Vehicle is culture medium completed with 0.2% of DMSO and 2% of FBS. Transepithelial electrical resistance (TEER) was measured each day. Threshold limit value is 100 $\Omega \cdot cm^2$. LDH release indicating cytotoxicity was measured at Day 2 and 3. Threshold limit value is 5% cytotoxicity, which corresponds to a daily physiological LDH release in MUCILAIR™. Cilia beating frequency was measured only at Day 3. Statistical comparison was performed using one-way ANOVA with Dunnett's multiple comparison post-tests (Prism 6 GraphPad). Epithelial barrier function was maintained (>100 $\Omega \cdot cm^2$) at all three tested concentrations of Celgosivir up to three days. No cytotoxicity (≥5%) was observed for Celgosivir at Day 2 and 3. The 10% Triton X-100 solution induced toxicity was 100%. The vehicle treated cultures showed cilia beating frequency of 5.5 Hz at room temperature, which is in the normal range of MUCILAIR™ (4-8 Hz). Exposure to Celgosivir did not modify significantly cilia motion.
Figure 6B:
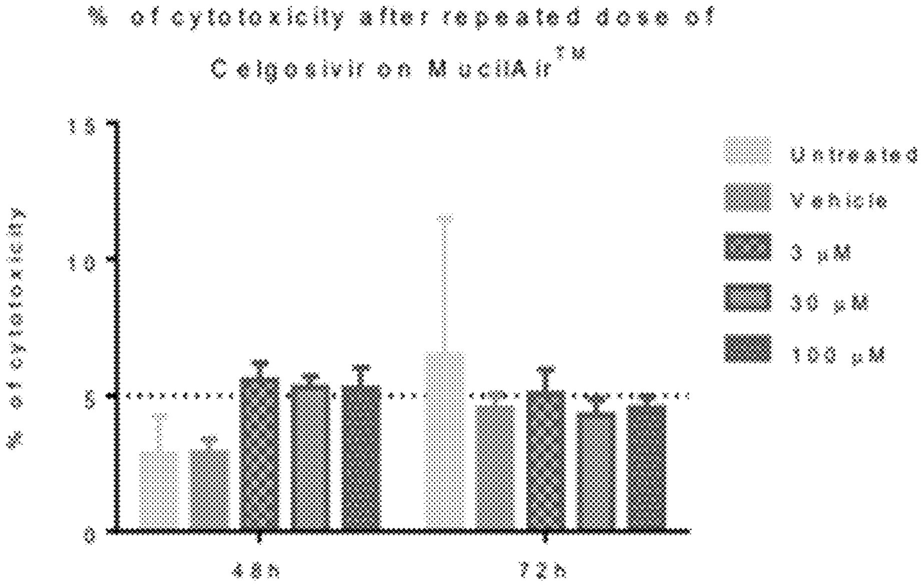
Figure 6C:
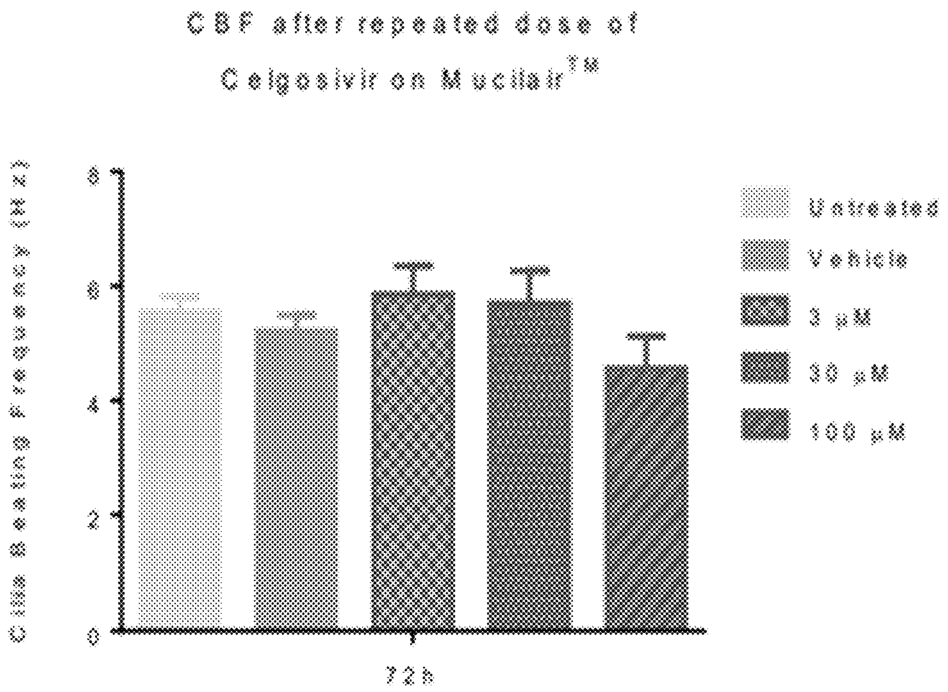

Example 2: Celgosivir is Active Against SARS-CoV-2 in Primary Human Respiratory Epithelia Celgosivir at concentrations of 30 and 100 microM decreased SARS-CoV-2 replication and yield of viral progeny, and provided a protective effective against virus-induced cytopathology in human primary respiratory epithelium [FIGS. 3, 4, and 5, respectively]. These effects were dose-related since they happened to a diminished extent at 3 microM. Earlier studies had shown that celgosivir concentrations at or below 100 microM did not exhibit evidence of cytoxicity as evidenced by similar TEER, cytotoxicity, and CBF values to appropriate controls [FIG. 6]. Remdesivir, 5 microM, included as a positive control exhibited more pronounced inhibition of viral replication, but similar inhibitory effects on viral yield reduction as celgosivir [FIGS. 4 and 5], consistent with its virus, rather than hosted cell directed, mode of action. The methodology utilized to generate these data is further described below.

Assay System:

The assay system used in this study is Epithelix' proprietary technology MucilAir™. MucilAir™ is a pseudostratified and ready-to-use 3D model of human airway epithelium, constituted with primary human epithelial cells freshly isolated from nasal, tracheal or bronchial biopsies. When switched at the air-liquid interface, the progenitor cells undergo a progressive differentiation and polarization to a fully ciliated epithelium. The mature MucilAir™ is composed of basal cells, ciliated cells and mucus cells. The proportion of these various cell types is preserved compared to what one observes in vivo (Huang S, CaulFuty M "A novel in vitro cell model of the human airway epithelium" 3R-Info-Bulletin No. 41, October 2009). MucilAir™, a fully differentiated 3D in vitro cell model of the human airway epithelia. Epithelial cells were freshly isolated from the biopsies (nose, trachea and bronchi), then seeded onto a semi-porous membrane (Costar Transwell, pore size 0.4 μm). After culture at air-liquid interface, the epithelia were fully differentiated, both morphologically and functionally.

Moreover, MucilAir™ is functionally differentiated, secretes mucus and are electrically tight (TEER>200

Ω·$cm^2$). The activity of the main epithelial ionic channels, such as CFTR, EnaC, Na/K ATPase, is preserved and the epithelia is shown to respond in a regulated and vectorial manner to the pro-inflammatory stimulus, TNF-α (Huang et al., 2011). A large panel of cytokines, chemokines and metalloproteinases has been detected in MucilAir™ (e.g. IL-8, IL-6, GM-CSF, MMP-9, GRO-a). Most importantly, MucilAir™ replicates the main function of the airway epithelial cells, the mucociliary clearance driven by synchronized cilia-beating.

MucilAir™ is used for the following acute, long-term and chronic in vitro studies (Boda B., et al., "Antiviral drug screening by assessing epithelial functions and innate immune responses in human 3D airway epithelium model" Antiviral Res. 2018 156:72-79; Balogh Sivars et al., "A 3D human airway model enables prediction of respiratory toxicity of inhaled drugs in vitro" Toxicol Sci. 2018 162(1): 301-308; Essaidi-Laziosi et al., "Propagation of respiratory viruses in human airway epithelia reveals persistent virus-specific signatures" J Allergy Clin Immunol. 2018141(6): 2074-2084; Hoffmann et al. "Establishment of a Human 3D Tissue-Based Assay for Upper Respiratory Tract Absorption" Applied In Vitro Toxicology 20184(2): 139-148; Constant et al., "The Use of in vitro 3D Cell Models of Human Airway Epithelia (MucilAir™) in Inhalation Toxicity". Cellular InVitro Testing: Methods and Protocols 2014 15; Reus et al. "Feasibility of a 3D human airway epithelial model to study respiratory absorption" Toxicology In Vitro 2013; Tapparel et al. "Growth and characterization of different human rhinovirus C types in three-dimensional human airway epithelia reconstituted in vitro" Virology 2013, 446(1): 1-8).

The epithelium source is shown below in Table 5. Nasal epithelia were all fully differentiated at the start of the experiment (air-liquid interface culture: ALI; week number denotes the seeding date of year).

TABLE 5

| Epithelium Source | | | | |
|---|---|---|---|---|
| Batch number | Age of the patient | Sex of the patient | Age of cultures | Special comments |
| MP0009 week 28 | — | — | 36 days (ALI) | Pool of donors No pathology Phase 1 |
| MP0009 week 34 | — | — | 41 days | Pool of donors No pathology Phase 2 |

Nasal epithelum source for MP0009 batch is shown in Table 6.

TABLE 6

| Batch number | Age | Gender |
|---|---|---|
| AB081301 | 52 | M |
| AB080901 | 24 | M |
| AB080801 | 36 | M |
| AB080601 | 32 | M |
| AB080301 | 58 | M |
| AB079801 | 44 | F |
| AB079701 | 55 | M |
| AB078001 | 55 | M |
| AB076201 | ND | ND |
| AB075502 | 54 | F |
| AB074501 | 53 | M |

TABLE 6-continued

| Batch number | Age | Gender |
|---|---|---|
| AB073801 | 32 | F |
| AB073501 | 57 | M |
| AB073101 | 58 | M |

Methods:

Phase 1:

The testing strategies includes basolateral exposure of test compounds on MucilAir™-Pool. Endpoint measurements were performed at 24, 48 and 72 hours from apical side and basolateral medium.

Global markers of Toxicity included (1) Tissue integrity monitoring: Trans-epithelial electrical resistance (TEER) measurement and (2) Cytotoxicity: Lactate dehydrogenase (LDH) assay.

Effect on cilia included cilia motion: Cilia Beating Frequency (CBF).

Figure 7:
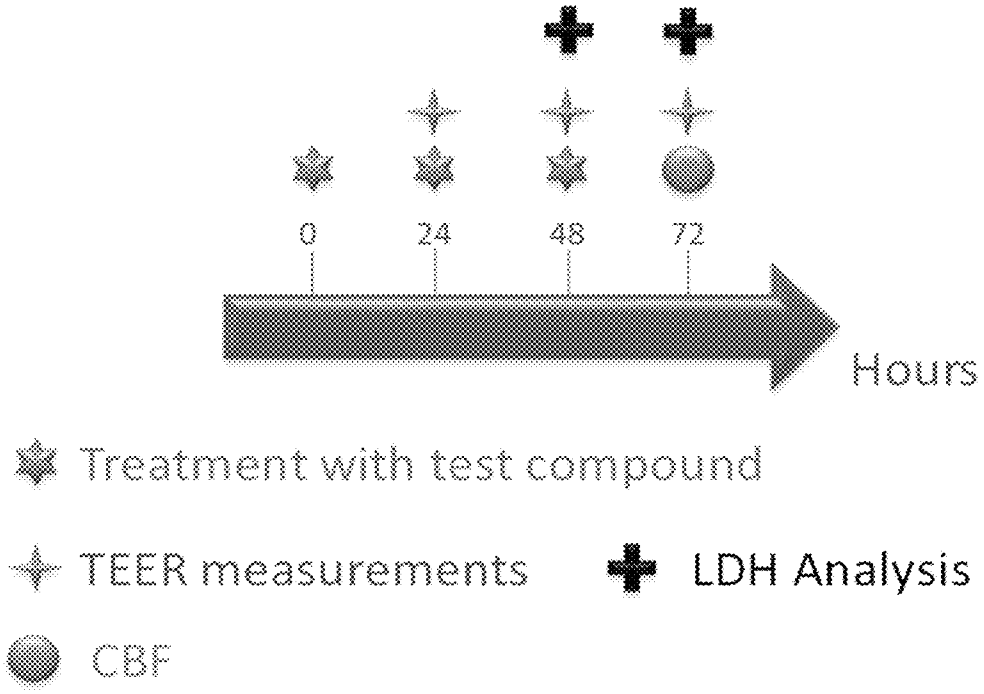
FIG. 7 shows the testing strategy for Example 2, phase 1. Repeated basolateral exposure once a day of test compounds on MUCILAIR™-Pool. Transepithelial electrical resistance (TEER) was assessed each day. LDH release indicating cytotoxicity, was measured at Day 2 and 3 (24 hours accumulation). Cilia beating frequency (CBF) was measured once, at the end of the experiment, at Day 3.

Repeated basolateral exposure once a day of test compounds on MucilAir™-Pool. Transepithelial electrical resistance (TEER) was assessed each day. LDH release indicating cytotoxicity, was measured at Day 2 and 3 (24 hours accumulation). Cilia beating frequency (CBF) was measured once, at the end of the experiment, at Day 3. (FIG. 7)

Number of repeats: 3

Compound: Celgosivir N=18

Number of concentrations: 3 doses

Celgosivir=100, 30 and 3 mM on basolateral side in 0.2% DMSO and 2% fetal bovine serum Controls:

Negative controls (N=6):

1. Untreated cultures N=3
2. Basolateral vector (0.2% DMSO and 2% fetal bovine serum in culture medium) (N=3

Positive controls (N=3)

1. Triton X-100 (for cytotoxicity; apical 100 ml of 10% for 24 h) N=3

Type of epithelia used: MucilAir™-Nasal-Pool

Number of MucilAir™: 27 inserts

Phase 2:

Basolateral exposure of compounds on MucilAir™-Pool. Endpoint measurements were performed at 24, 48, and 72 hours from apical side.

Effect on virus replication included (1)Virus genome copy number: Taqman RT-PCR and (2) Infectious titer quantification: $TCID_{50}$ analysis (for relevant conditions only).

Global markers of Toxicity included Tissue integrity monitoring: Trans-epithelial electrical resistance (TEER) measurement.

Figure 8:
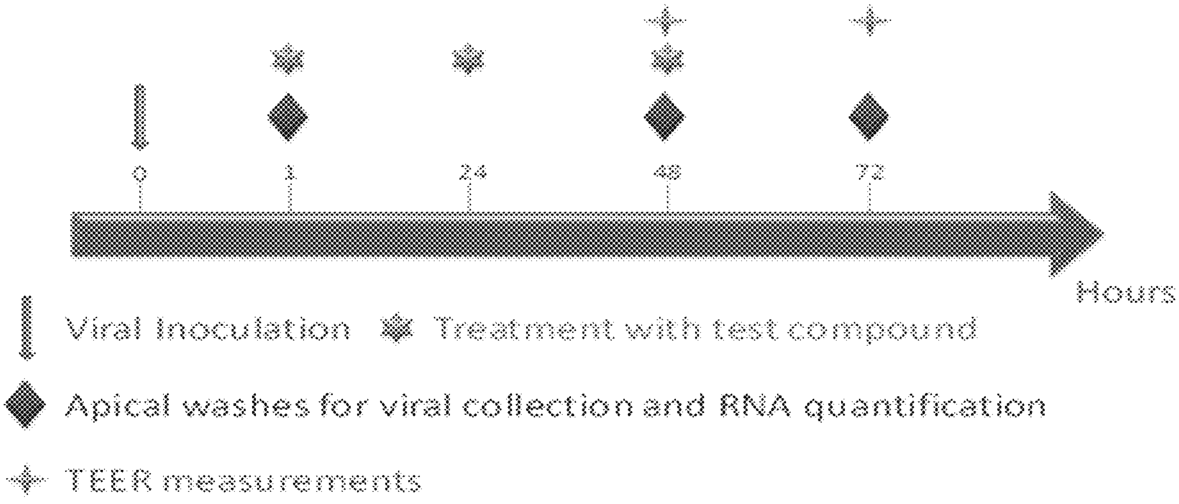
FIG. 8 shows the testing strategy for Example 2, phase 2. Repeated basolateral exposure once a day of test compounds on MUCILAIR™-Pool. Viral RNA was quantified from apical wash at 48 and 72 hours. Transepithelial electrical resistance (TEER) was assessed at 48 and 72 hours.

Repeated basolateral exposure once a day of test compounds on MucilAir™-Pool. Viral RNA was quantified from apical wash at 48 and 72 hours. Transepithelial electrical resistance (TEER) was assessed at 48 and 72 hours (FIG. 8).

Number of repeats: 3

Inoculum input: 1 (MOI of 0.1)

Number of concentrations: 3 doses

Compound: Celgosivir, N=18

Controls:

Negative controls (N=6):

1. Vehicle control (1% DMSO)—Basal treatment with virus N=3
2. Vehicle control (1% DMSO)—Basal treatment without virus N=3

Positive controls (N=3)

1. Inhibition of replication (5 mM remdesivir) N=3

Type of epithelia used: MucilAir™-Nasal-Pool

Number of MucilAir™: 21 inserts

The vehicle of Phase 2 was 1% DMSO, n=4 cultures, and remdesivir treatment was also performed with 4 cultures. The total number of MucilAir™ in Phase 2 was 21.

Protocols

−3 Days Quality Control and Washing the Apical Surface

The airway epithelium is a layer of pseudo-stratified epithelium. When reconstituted on the semi-porous membrane, the appearance of the epithelia is homogenous and uniform. Since the Transwell membrane is clear and transparent, the morphological changes could easily be monitored. Each insert was inspected under a conventional inverted microscope to insure the quality of the epithelia. The movement of cilia was clearly visible for all the selected inserts and the presence of mucus was detected by the refractive aspect of the apical surface.

Each insert used was selected and washed apically with culture medium three days before the experiments. This washing step allowed removing accumulated mucus and cell debris to minimize the risk of interference with the tests. Trans-Epithelial Electrical Resistance (TEER) was also measured to verify that all the selected inserts satisfy the internal quality control standards (>200 $\Omega\cdot cm^2$).

Phase 1:

TABLE 7

Protocol of the Phase 1. Buffered saline solution contains 0.9% NaCl, 10 mM HEPES and 1.25 mM $CaCl_2$.

| Time point | Schedule of actions |
|---|---|
| D 0 | 1. Transfer the inserts into a new culture plate with 500 ml of test compound-containing culture medium per well |
| | 2. Incubation (37° C.; 5% $CO_2$; 100% humidity) for 24 hours |
| D 1 | 1. Addition of 200 ml of buffered saline to the apical side |
| | 2. TEER measurement |
| | 3. Removal of apical liquid |
| | 4. Transfer the inserts into a new culture plate with 500 ml of test compound-containing culture medium per well |
| | 5. Incubate at 37° C., 100% humidity; 5% $CO_2$ for 24 hours |
| D 2 | 1. Addition of 200 ml of buffered saline to the apical side |
| | 2. TEER measurement |
| | 3. Removal of apical liquid |
| | 4. Transfer the inserts into a new culture plate with 500 ml of test compound-containing culture medium per well |
| | 5. Old culture medium being used for LDH assay |
| | 6. Incubate at 37° C., 100% humidity; 5% $CO_2$ for 24 hours |
| D 3 | 1. Cilia Beating Frequency measurement |
| | 2. Mucociliary clearance measurement |
| | 3. Addition of 200 ml of buffered saline to the apical side |
| | 4. TEER measurement |
| | 1. Culture medium being used for LDH assay |

Phase 2:

TABLE 8

Protocol of the Phase 2. Note: Samples collected from apical washes at different time-points were separated into 2 tubes: one for $TCID_{50}$ viral titration and one for RT-qPCR. While RT-qPCR analysis was performed for all conditions, $TCID_{50}$ was performed only for selected compounds and time-points chosen after RT-qPCR analysis.

| Time point | Schedule of actions |
|---|---|
| T0 | 1. Transfer the inserts into a new culture plate with 700 ml of culture medium per well |
| | 2. Two Apical washes with 200 ml of OptiMEM ™ culture media for 10 min at 37° C. |
| | 3. Virus inoculation in 150 ml OptiMEM ™ culture media (MOI 0.1) |
| | 4. Incubation (37° C.; 5% $CO_2$; 100% humidity) for 1 hour |
| T1 h | 1. Inoculum removal |
| | 2. Transfer the inserts into a new culture plate with 700 ml of test compound-containing culture medium per well |
| | 3. Incubation (37° C.; 5% $CO_2$; 100% humidity) for 23 hours |
| T24 h | 1. Transfer the inserts into a new culture plate with 700 ml of test compound-containing culture medium per well |
| | 2. Incubation (37° C.; 5% $CO_2$; 100% humidity) for 24 hours |
| T48 h | 1. Addition of 200 µL of OptiMEM ™ culture media for 10 min at 37° C. |
| | 2. TEER measurement |
| | 3. Removal of apical liquid (140 µL for inactivation and quantification of viral copy numbers, remaining liquid (around 60 µL) will be stored at −80° C. for further quantification if needed) |
| | 4. Transfer the inserts into a new culture plate with 700 ml of test compound-containing culture medium per well |
| | 5. Incubation (37° C.; 5% $CO_2$; 100% humidity) for 24 hours |

TABLE 8-continued

Protocol of the Phase 2. Note: Samples collected from apical washes at different time-points were separated into 2 tubes: one for $TCID_{50}$ viral titration and one for RT-qPCR. While RT-qPCR analysis was performed for all conditions, $TCID_{50}$ was performed only for selected compounds and time-points chosen after RT-qPCR analysis.

| Time point | Schedule of actions |
|---|---|
| T72 h | 1. Addition of 200 μL of OptiMEM ™ culture media for 10 min at 37° C.<br>2. TEER measurement<br>3. Removal of apical liquid (100 μL for quantification of viral copy numbers, remaining liquid will be stored at −80° C. for further quantification if needed) |

Tissue Integrity (TEER)

TEER is a dynamic parameter that reflects the state of epithelia and is typically between 200 to 600 $\Omega \cdot cm^2$. An increase of the TEER value reflects a blockage of the ion channel activities. A notable decrease of the TEER values (but >100 $\Omega \cdot cm^2$) could be observed in certain cases, reflecting an activation of the ion channels. Disruption of cellular junction or holes in the epithelia result in TEER values below 100 $\Omega \cdot cm^2$. When an epithelium is damaged, a decrease of TEER would be associated with an increase of LDH release or a decrease of the cell viability.

After addition of 200 μl of 0.9% saline solution to the apical compartment of MucilAir™ cultures, resistance was measured with an EVOMX volt-ohm-meter (World Precision Instruments UK, Stevenage) for each condition. Resistance values (Ω) were converted to TEER ($\Omega \cdot cm^2$) using the following formula: TEER ($\Omega \cdot cm^2$)=(resistance value (Ω)−100(Ω))×0.33 ($cm^2$), where 100Ω is the resistance of the membrane and 0.33 $cm^2$ is the total surface of the epithelium.

Lactate Dehydrogenase (LDH) Assay

Lactate dehydrogenase is a stable cytoplasmic enzyme that is rapidly released into the culture medium upon rupture of the plasma membrane. 100 μL basolateral medium collected at each time-point was incubated with the reaction mixture of the Cytotoxicity Detection Kit$^{PLUS}$, following manufacturer's instructions (Sigma, Roche, 11644793001). The amount of the released LDH was then quantified by measuring the absorbance of each sample at 490 nm with a microplate reader. To determine the percentage of cytotoxicity, the following equation was used (A=absorbance values):

$$\text{Cytotoxicity}(\%)=(A(\text{exp value})-A(\text{low control})/A(\text{high control})-A(\text{low control}))*100$$

The high control value was obtained by 10% Triton X-100 treatment 24 hours prior to the assay. Triton X-100 causes a massive LDH release and corresponds to 100% cytotoxicity.

Cilia Beating Frequency (CBF)

Cilia beating frequency was monitored using a MAKO G030B camera connected to a ZEISS Primovert microscope with a 5× objective.

CBF measurement is based on the capture of 256 frames at high frequency rate (125 frames per second) at room temperature via the specific package of software. The frequency is expressed as Hertz and was calculated using an Epithelix software.

It should be pointed out that CBF values may be subject to fluctuations due to parameters such as temperature, mucus viscosity or liquid applied on the apical surface of MucilAir™.

Virus Inoculation

The SARS-CoV-2 strain used in the study was isolated by directly inoculating VeroE6 cell monolayers with a nasal swab sample collected from Bichat Claude Bernard Hospital, Paris. Once characteristic cytopathic effect was observable in more than 50% of the cell monolayer, supernatants were collected and immediately stored at −80° C. The complete viral genome sequence was obtained using Illumina MiSeq sequencing technology and was deposited under the name BetaCoV/France/IDF0571/2020. Viral stocks were titrated by tissue culture infectious dose 50% ($TCID_{50}$/ml) in VeroE6 cells, using the Reed & Muench statistical method.

Prior to infection, the apical side of the MucilAir™ cultures were washed twice for 10 min. Inoculations were performed with 150 μl at a theoretical multiplicity of infection (MOI) of 0.1 (50 000 TCID50 for an average of 500 000 cells in MucilAir™), applied to the apical side of the cultures for 1 hour at 37° C., 5% $CO_2$. Non-infected control, Mock, was exposed also to 150 μl of culture medium on the apical side for 1 hour. Unbound viruses were removed after one hour of incubation period. New viral particles were collected by 10 min apical washes (200 ml) 48 and 72 hours post-inoculation and quantified by RT-qPCR.

Reference antiviral drug remdesivir was purchased from MedChemExpress, (HY-104077) and was diluted in DMSO and used at 5 μM (final concentration of DMSO was 0.05%).

Reference and test antiviral compounds were added after one hour of viral inoculation in the basal medium and basal medium was changed every day.

Real-Time Taqman Probe RT-PCR

From the 200 μl apical washes, 140 μl was used for viral RNA extraction with the QIAamp® Viral RNA kit (Qiagen), obtaining 60 μl of eluted RNA. Viral RNA was quantified by quantitative RT-PCR (EXPRESS One-Step Superscript™ qRT-PCR Kit, Invitrogen, 1178101K) using 2 μl of viral RNA with Mastermix and two ORF1b-nsp14 specific primers (5'-TGGGGYTTTACRGGTAACCT-3' (SEQ ID NO:1); 5'-AACRCGCTTAACAAAGCACTC-3' (SEQ ID NO:2)) and probe (5'-FAM-TAGTTGTGATGCWATCATGACTAG-TAMRA-3' (SEQ ID NO:3)) of SARS-CoV-2 designed by the School of Public Health/University of Hong Kong (Leo Poon, Daniel Chu and Malik Peiris). All samples were divided into 4 PCR plates (series 1: plate 3 and 4; series 2: plate 1 and 2) and were run on StepOnePlus™ Real-Time PCR System (Applied Biosystems). Ct data were determined and relative changes in gene expression were calculated using the $2^{-\Delta Ct}$ method and reported as the fold reduction relative to the mean of untreated infected inserts.

Infectious Titre

The appearance of clearly observable cytopathic effect of SARS-CoV-2 from 48 hours post-inoculation permitted the classic infectious titre determination in cell culture, the Median Tissue Culture Infectious Dose (TCID50) using African green monkey VeroE6 cell line. The assay enabled the validation of a large interval, range 1-8 log 10 (TCID50) and showed high correlation (R-squared 0.94) with molecular viral quantification (RT-qPCR) (Pizzorno et al., 2020).

Statistical Analysis

Data were expressed as mean±standard error of mean, and assumed to have normal distribution. Differences between three or more groups were tested by one-way or two-way ANOVA with Dunnett's multiple comparison post-tests using Prism 6 GraphPad software (La Jolla, USA). Differences between two groups were tested by Student's t test. The values $P<0.05$ were considered statistically significant (*$p<0.05$, $p<0.01$, *$p<0.001$, ****$p<0.0001$).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for treating human coronavirus infection or a symptom, in a human subject, wherein the coronavirus is SARS-COV-2 or a variant thereof, said method comprising administering an effective amount of an alpha-glucosidase glycoprotein processing inhibitor to the human subject, wherein said alpha-glucosidase glycoprotein processing inhibitor comprises castanospermine or a pharmaceutically acceptable salt or prodrug thereof, and wherein the prodrug of castanospermine has the following structure of Formula (I):

(I)

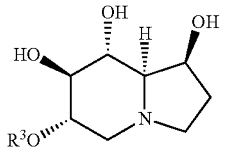

wherein $R^3$ is $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

2. The method of claim 1, further comprising, prior to said administering, identifying the subject as having the coronavirus infection, wherein said identifying comprises assaying a biological sample obtained from the subject for the presence of coronavirus nucleic acid or coronavirus protein.

3. The method of claim 1, wherein the prodrug comprises celgosivir (6-O-butanoyl castanospermine) or a pharmaceutically acceptable salt thereof.

```
                    SEQUENCE LISTING

<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1

tggggyttta crggtaacct                                        20


<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2

aacrcgctta acaaagcact c                                      21


<210> SEQ ID NO 3
<211> LENGTH: 24
<212> TYPE: DNA
<213> ORGANISM: Artificial sequence
<220> FEATURE:
<223> OTHER INFORMATION: probe

<400> SEQUENCE: 3

tagttgtgat gcwatcatga ctag                                   24
```

4. The method of 1, wherein said method comprises:

(a) determining that the human subject is infected with a coronavirus;

(b) administering to the human subject at least one initial dose of about 15 mg to about 600 mg of a compound of Formula (I); and (c) administering to the human subject a plurality of subsequent doses of about 15 mg to about 400 mg of a compound of Formula (I) or a pharmaceutically acceptable salt thereof, wherein not more than 600 mg of a compound of Formula (I) is administered per day.

5. The method of claim 4, wherein the compound of Formula (I) is a compound of Formula (II), or a pharmaceutically acceptable salt thereof:

(II)

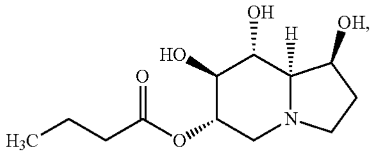

6. The method of claim 4, wherein the compound of Formula (I) is converted to castanospermine after administration to the human subject, and wherein a steady state Cmin serum or plasma concentration of between about 0.4 and about 2.0 microgram/ml of castanospermine is attained in the human subject after administrations of initial and subsequent doses.

7. The method of claim 1, wherein the prodrug of castanospermine has the following structure:

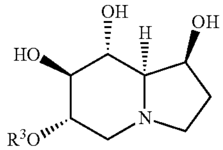

wherein $R^3$ is ($C_1$-$C_{14}$) acyl.

8. The method of claim 1, wherein the subject has a viral load reduction after receiving the alpha-glucosidase glycoprotein processing inhibitor of at least 50% greater than said subject not administered the alpha-glucosidase glycoprotein processing inhibitor or in a placebo-administered group.

9. The method of claim 1, wherein the SARS-COV-2 infection is from a SARS-COV-2 variant selected from the group consisting of B.1.1.7, B.1.351, and P.1.

10. The method of claim 1, wherein the alpha-glucosidase inhibitor is administered with a permeability enhancer.

11. The method of claim 1, wherein the human subject is further administered an antiviral drug, a monoclonal antibody treatment, a steroid, or COVID-19 convalescent plasma.

12. The method of claim 11, wherein the monoclonal antibody treatment is casirivimab, imdevimab, or bamlanivimab.

13. The method of claim 11, wherein the antiviral drug is remdesivir, chloroquine, hydroxychloroquine, or favipiravir.

14. The method of claim 1, wherein the human subject is further administered a second agent is selected from the group consisting of amikacin, amphotericin, atovaquone, Bactrim, clindamycin, corticosteroids, echinocandin, fluconazole, flucytosine, itraconazole, posaconazole, quinine, sulfa drugs, trimethoprimsulfamethoxazole, voriconazole, baricitinib, interleukin-6 inhibitors, tyrosine kinase inhibitors, Tocilizumab, ivermectin, and any combination thereof.

* * * * *